United States Patent
Michels et al.

(10) Patent No.: US 8,759,341 B2
(45) Date of Patent: Jun. 24, 2014

(54) BI- AND TRICYCLIC INDAZOLE-SUBSTITUTED 1,4-DIHYDROPYRIDINE DERIVATIVES AND USES THEREOF

(75) Inventors: Martin Michels, Köln (DE); Markus Follmann, Wülfrath (DE); Alexandros Vakalopoulos, Hilden (DE); Katja Zimmermann, Düsseldorf (DE); Mario Lobell, Wuppertal (DE); Nicole Teusch, Wülfrath (DE); Shendong Yuan, San Ramon, CA (US)

(73) Assignee: Bayer Intellectual Property GmbH, Monheim (DE)

( * ) Notice: Subject to any disclaimer, the term of this patent is extended or adjusted under 35 U.S.C. 154(b) by 34 days.

(21) Appl. No.: 13/201,482

(22) PCT Filed: Feb. 5, 2010

(86) PCT No.: PCT/EP2010/000718
§ 371 (c)(1),
(2), (4) Date: Oct. 26, 2011

(87) PCT Pub. No.: WO2010/094405
PCT Pub. Date: Aug. 26, 2010

(65) Prior Publication Data
US 2012/0035409 A1    Feb. 9, 2012

Related U.S. Application Data

(60) Provisional application No. 61/207,931, filed on Feb. 18, 2009.

(51) Int. Cl.
*C07D 401/04* (2006.01)
*C07D 471/04* (2006.01)
*C07D 491/048* (2006.01)
*C07D 491/147* (2006.01)
*C07D 491/153* (2006.01)
*C07D 495/04* (2006.01)
*C07D 498/14* (2006.01)

(52) U.S. Cl.
USPC ........ 514/230.2; 514/291; 514/299; 514/300; 514/301; 514/314; 544/101; 546/113; 546/114; 546/116; 546/165; 546/183

(58) Field of Classification Search
None
See application file for complete search history.

(56) References Cited

U.S. PATENT DOCUMENTS

2008/0176833 A1* 7/2008 Adler et al. .............. 514/217.04

* cited by examiner

*Primary Examiner* — Kamal Saeed

(57) ABSTRACT

This invention relates to novel bi- and tricyclic indazole-substituted 1,4-dihydropyridine derivatives having protein tyrosine kinase inhibitory activity, to a process for the manufacture thereof and to the use thereof for the treatment of c-Met-mediated diseases or c-Met-mediated conditions, particularly cancer and other proliferative disorders.

12 Claims, No Drawings

BI- AND TRICYCLIC INDAZOLE-SUBSTITUTED 1,4-DIHYDROPYRIDINE DERIVATIVES AND USES THEREOF

This invention relates to novel bi- and tricyclic indazole-substituted 1,4-dihydropyridine derivatives having protein tyrosine kinase inhibitory activity, to a process for the manufacture thereof and to the use thereof for the treatment of c-Met-mediated diseases or c-Met-mediated conditions, particularly cancer and other proliferative disorders.

Cancer is one of the most common widespread diseases. Over 4.4 million people worldwide were diagnosed with breast, colon, ovarian, lung or prostate cancer in 2002, and over 2.5 million people died of these devastating diseases (Globocan 2002 Report, http://www-dep.iarc.fr/globocan/downloads.htm). In the United States alone, over 1.25 million new cases and over 500 000 deaths from cancer were predicted in 2005. The majority of these new cases were expected to be cancers of the colon (~100 000), lung (~470 000), breast (~210 000) and prostate (~230 000). Both the incidence and prevalence of cancer is predicted to increase by approximately 15% over the next ten years, reflecting an average growth rate of 1.4% (American Cancer Society, Cancer Facts and Figures 2005; http://www.cancer.org/docroot/STT/content/STT_1x_Cancer_Facts_Figures_2007.asp).

There are many ways how cancers can arise, which is one of the reasons why their therapy is difficult. One way is the transformation of cells by oncoproteins, which arise from normal cellular proteins by genetic mutations, which results in a non-physiological activation of these proteins. One family of proteins from which a number of oncoproteins derive are tyrosine kinases (e.g. src kinase) and in particular receptor tyrosine kinases (RTKs). In the past two decades, numerous avenues of research have demonstrated the importance of receptor tyrosine kinase (RTK)-mediated signalling in the regulation of mammalian cell growth. Recently, results have been achieved in the clinic with selective small-molecule inhibitors of tyrosine kinases as anti-tumourigenic agents.

The c-Met receptor also is a receptor tyrosine kinase. Its oncogenic potential was identified in the early 1980s, when a mutated Met was isolated from a chemically induced human osteosarcoma cell line which contained the kinase domain of the Met gene fused to a dimerization domain at its N-terminus [C. S. Cooper et al., *Nature* 311: 29-33 (1984)].

The cellular Met protein is a heterodimeric transmembrane protein synthesized as a single chain 190 kd precursor [G. A. Rodrigues et al., *Mol. Cell. Biol.* 11: 2962-70 (1991)]. The precursor is cleaved intracellularly after amino acid residue 307 to form the 50 kd α-chain and the 145 kd β-chain, which are connected by disulfide bridges. The α-chain is entirely extracellular, whereas the β-chain spans the plasma membrane. The β-chain is composed of an N-terminal sema domain, which together with the α-chain mediates ligand binding. The remainder of the ectodomain of the β-chain is composed of a cysteine-rich domain and four immunoglobulin domains and is followed by the transmembrane region and the intracellular domain. The intracellular domain contains a juxtamembrane domain, the kinase domain and a C-terminal domain, which mediates the downstream signalling. Upon ligand binding, a dimerization of the receptor is induced, and the kinase domain is activated by a cascade of tyrosine autophosphorylation steps in the juxtamembrane region (Y1003), the activation loop of the kinase (Y1234 and Y1235) and the carboxy-terminal domain (Y1349 and Y1356). Phosphorylated Y1349 and Y1356 comprise the multi-substrate docking site for binding adapter proteins necessary for downstream c-Met signalling [C. Ponzetto et al., *Cell* 77: 261-71 (1994)].

One of the most crucial substrates for c-Met signalling is the scaffolding adaptor protein Gab1, which binds to either Y1349 or Y1356 via an unusual phosphotyrosine binding site (termed mbs: met binding site) which causes a unique prolonged intracellular signal. Another important substrate is the adaptor protein Grb2. Depending on the cellular context, these adaptors mediate the activation of various intracellular signal pathways like the ones signalling via ERK/MAPK, PI3K/Akt, Ras, INK, STAT, NFκB and β-catenin.

c-Met is uniquely activated by hepatocyte growth factor (HGF), also known as scatter factor, and its splice variants, which is its only known biologically active ligand [L. Naldini et al., *Oncogene* 6: 501-4 (1991)]. HGF has a distinct structure which reveals similarities to proteinases of the plasminogen family. It is composed of an amino-terminal domain followed by four kringle domains and a serine protease homology domain, which is not enzymatically active. Similar to c-Met, HGF is synthesized as an inactive single chain precursor (pro-HGF), which is extracellularly cleaved by serine proteases (e.g. plasminogen activators and coagulation factors) and converted into a disulfide-linked active α- and β-chain heterodimer. HGF binds heparan sulfate proteoglycans with high affinity, which keeps it mainly associated with the extracellular matrix and limits its diffusion. Crystal structure analyses indicate that HGF forms a dimer, which upon binding to c-Met induces dimerization of the receptor.

HGF is expressed by mesenchymal cells, and its binding to c-Met, which is widely expressed in particular in epithelial cells, results in pleiotropic effects in a variety of tissues including epithelial, endothelial, neuronal and hematopoetic cells. The effects generally include one or all of the following phenomena: i) stimulation of mitogenesis; HGF was identified by its mitogenic activity on hepatocytes; ii) stimulation of invasion and migration; in an independent experimental approach, HGF was identified as scatter factor based on its induction of cell motility ("scattering"); and iii) stimulation of morphogenesis (tubulogenesis). HGF induces the formation of branched tubules from canine kidney cells in a collagen matrix. Furthermore, evidence from genetically modified mice and from cell culture experiments indicate that c-Met acts as a survival receptor and protects cells from apoptosis [N. Tomita et al., *Circulation* 107: 1411-1417 (2003); S. Ding et al., *Blood* 101: 4816-4822 (2003); Q. Zeng et al., *J. Biol. Chem.* 277: 25203-25208 (2002); N. Horiguchi et al., *Oncogene* 21: 1791-1799 (2002); A. Bardelli et al., *Embo J.* 15: 6205-6212 (1996); P. Longati et al., *Cell Death Differ.* 3: 23-28 (1996); E. M. Rosen, *Symp. Soc. Exp. Biol.* 47: 227-234 (1993)]. The coordinated execution of these biological processes by HGF results in a specific genetic program which is termed as "invasive growth".

Under normal conditions, c-Met and HGF are essential for embryonic development in mice, in particular for the development of the placenta and the liver and for the directional migration of myoblasts from the somites of the limbs. Genetic disruption of the c-Met or HGF genes results in identical phenotypes which shows their unique interaction. The physiological role of c-Met/HGF in the adult organism is less well understood, but experimental evidence suggests that they are involved in wound healing, tissue regeneration, hemopoiesis and tissue homeostasis.

The identification of the oncoprotein TPR-MET was a first hint that c-Met may play a role in tumourigenesis. Additional substantial evidence is derived from a number of different experimental approaches. Overexpression of c-Met or HGF in human and murine cell lines induces tumourigenicity and a metastatic phenotype when expressed in nude mice. Transgenic overexpression of c-Met or HGF induces tumourigenesis in mice.

Most intriguingly, missense mutations of c-Met or mutations which activate the receptor have been identified in sporadic and hereditary papillary kidney carcinomas (HPRC) as well as in other cancer types like lung, gastric, liver, head and neck, ovarian and brain cancers. Significantly, specific c-Met mutations in HPRC families segregate with disease, forming a causal link between c-Met activation and human cancer [L. Schmidt et al., *Nat. Genet.* 16: 68-73 (1997); B. Thar et al., *Adv. Cancer Res.* 75: 163-201 (1998)]. Activation mutations with the strongest transforming activities are located in the activation loop (D1228N/H and Y1230H/D/C) and in the adjacent P+1 loop (M1250T). Additional weaker mutations have been found near the catalytic loop and within the A lobe of the kinase domain. Furthermore, some mutations in the juxtamembrane domain of c-Met have been observed in lung tumours which do not directly activate the kinase, but rather stabilize the protein by rendering it resistant to ubiquitination and subsequent degradation [M. Kong-Beltran et al., *Cancer Res.* 66: 283-9 (2006); T. E. Taher et al., *J. Immunol.* 169: 3793-800 (2002); P. Peschard et al., *Mol. Cell.* 8: 995-1004 (2001)]. Interestingly, somatic mutations of c-Met are associated with increased aggressiveness and extensive metastases in various cancers. While the frequency of germ line and somatic mutations is low (below 5%), other major mechanisms have been observed leading to a deregulation of the c-Met signalling, in the absence of mutations, by paracrine or autocrine mechanisms. Paracrine activation has been observed in tumours which are derived from mesenchymal cells, like osteosarcomas or rhabdomyosarcomas, which physiologically produce HGF, and in glioblastomas and mamma carcinomas which are of ectodermal origin.

However, the most frequent cases are carcinomas where c-Met is overexpressed as observed in carcinomas of the colon, pancreas, stomach, breast, prostate, ovary and liver. Overexpression may arise, for example, by gene amplification as observed in gastric and lung tumour cell lines. Very recently, overexpression of c-Met was detected in lung tumour cell lines which acquired resistance to EGF receptor inhibition [J. A. Engelmann et al., *Science* 316: 1039-1043 (2007)]. Some epithelial tumours that overexpress c-Met also co-express HGF, resulting in an autocrine c-Met/HGF stimulatory loop and thereby circumventing the need for stromal cell-derived HGF.

In general, it has been found that aberrant activation of c-Met in human cancer is typically associated with a poor prognosis, regardless of the specific mechanism [J. G. Christensen et al., *Cancer Lett.* 225: 1-26 (2005)].

In summary, a great number of in vitro and in vivo studies have been performed that validate c-Met as an important cancer target, and a comprehensive list can be viewed at http://www.vai.org/met [C. Birchmeier et al., *Nat. Rev. Mol. Cell. Biol.* 4: 915-25 (2003)]. Several strategies have been followed to attenuate aberrant Met signalling in human tumours including HGF antagonists and small molecule inhibitors, amongst others. A number of small molecule inhibitors are currently in clinical development, such as ARQ-197 (Arqule), foretinib (XL-880, Exelixis/GSK), and PH-2341066 (Pfizer); they have recently been reviewed [J. J. Cui, *Expert Opin. Ther. Patents* 17: 1035-45 (2007)].

Lactone-, lactame- or cycloalkanone-annellated 4-heteroaryl-1,4-dihydropyridine derivatives that are useful for the treatment of cardiovascular diseases have been described in, inter al., EP 0 214 437-A2, EP 0 234 517-A1, EP 0 450 420-A2, EP 0 622 365-A1, EP 0 622 366-A1 and EP 0 630 895-A1. Further 4-heteroaryl-1,4-dihydropyridine derivatives containing a fused ring system in 2,3-position and use thereof for the treatment of various diseases have been disclosed in WO 00/51986-A1, WO 00/78768-A1, WO 02/10164-A2, WO 2005/025507-A2, WO 2006/047537-A1, WO 2006/066011-A2 and WO 2007/051062-A2. Recently, 1,4-dihydropyridine-type compounds having c-Met kinase inhibitory activity have been described in WO 2008/071451-A1.

The technical problem to be solved according to the present invention may therefore be seen in providing alternative compounds having an inhibitory activity on the c-Met kinase, thus offering new therapeutic options for the treatment of c-Met-mediated diseases, particularly cancer and other proliferative disorders.

In one aspect, the present invention relates to indazole-substituted 1,4-dihydropyridine derivatives of the general formula (I)

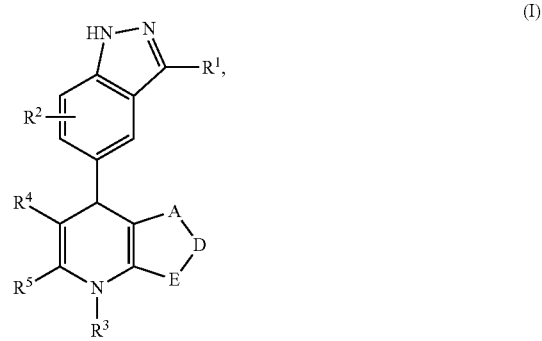

wherein
A is —C(=O)— or —S(=O)$_2$—,
D is —CR$^{6A}$R$^{6B}$—, —O— or —NR$^7$—, wherein
 R$^{6A}$, R$^{6B}$ and R$^7$ are independently hydrogen or (C$_1$-C$_4$)-alkyl optionally substituted with hydroxy or up to three fluoro atoms,
E is —CR$^{8A}$R$^{8B}$— or *—CR$^{8A}$R$^{8B}$—CR$^{8C}$R$^{8D}$—**,
 wherein
 * denotes the link to the dihydropyridine ring,
 ** denotes the link to the D group,
 and
 R$^{8A}$, R$^{8B}$, R$^{8C}$ and R$^{8D}$ are independently hydrogen, fluoro or (C$_1$-C$_4$)-alkyl optionally substituted with hydroxy, (C$_1$-C$_4$)-alkoxy, amino, mono-(C$_1$-C$_4$)-alkylamino or di-(C$_1$-C$_4$)-alkylamino or up to three fluoro atoms, or
 R$^{8A}$ and R$^{8B}$ are joined and, taken together with the carbon atom to which they are attached, form a cyclopropyl or cyclobutyl ring,
R$^1$ is selected from the group consisting of hydrogen, chloro, bromo, (C$_1$-C$_6$)-alkyl, (C$_3$-C$_7$)-cycloalkyl, phenyl, 4- to 7-membered heterocycloalkyl, 5- to 10-membered heteroaryl and benzo-1,4-dioxanyl, wherein
 (i) said (C$_3$-C$_7$)-cycloalkyl, phenyl, 4- to 7-membered heterocycloalkyl and 5- to 10-membered heteroaryl are optionally substituted with one or two substituents independently selected from the group consisting of fluoro, chloro, bromo, difluoromethyl, trifluoromethyl, (C$_1$-C$_4$)-alkyl, oxo, hydroxy, difluoromethoxy, trifluoromethoxy, (C$_1$-C$_4$)-alkoxy, amino, mono-(C$_1$-C$_4$)-alkylamino, di-(C$_1$-C$_4$)-alkylamino, (C$_3$-C$_6$)-cycloalkyl and 4- to 6-membered heterocycloalkyl, wherein the alkyl groups of said $(C_1-C_4)$-alkoxy, mono-$(C_1-C_4)$-alkylamino and di-$(C_1-C_4)$-alkylamino substituents in turn are optionally substituted with hydroxy or $(C_1-C_4)$-alkoxy, and (ii) said $(C_1-C_6)$-alkyl is optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, $(C_3-C_7)$-cycloalkyl, phenyl, 4- to 7-membered heterocycloalkyl and 5- to 10-membered heteroaryl, wherein said $(C_3-C_7)$-cycloalkyl, phenyl, 4- to 7-membered heterocycloalkyl and 5- to 10-membered heteroaryl substituents in turn are optionally substituted with one or two residues independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino and di-$(C_1-C_4)$-alkylamino, or $R^1$ is a group of the formula —$NR^{9A}R^{9B}$ or —$OR^{10}$, wherein $R^{9A}$ and $R^{9B}$ are independently selected from the group consisting of hydrogen, $(C_1-C_6)$-alkyl, $(C_3-C_7)$-cycloalkyl and 4- to 7-membered heterocycloalkyl, wherein (i) said $(C_3-C_7)$-cycloalkyl and 4- to 7-membered heterocycloalkyl are optionally substituted with one or two substituents independently selected from the group consisting of fluoro, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino and di-$(C_1-C_4)$-alkylamino, and (ii) said $(C_1-C_6)$-alkyl is optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, $(C_3-C_7)$-cycloalkyl, phenyl, 4- to 7-membered heterocycloalkyl and 5- to 10-membered heteroaryl, wherein said $(C_3-C_7)$-cycloalkyl, phenyl, 4- to 7-membered heterocycloalkyl and 5- to 10-membered heteroaryl substituents in turn are optionally substituted with one or two residues independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino and di-$(C_1-C_4)$-alkylamino, or $R^{9A}$ and $R^{9B}$ are joined and, taken together with the nitrogen atom to which they are attached, form a 4- to 7-membered heterocycloalkyl ring, which may contain a second ring heteroatom selected from N, O and S, and which is optionally substituted with one or two substituents independently selected from the group consisting of fluoro, $(C_1-C_4)$-alkyl, oxo, hydroxy, $(C_1-C_4)$-alkoxy, amino, mono-$(C_1-C_4)$-alkylamino, di-$(C_1-C_4)$-alkylamino and $(C_3-C_6)$-cycloalkyl, $R^{10}$ is selected from the group consisting of $(C_1-C_6)$-alkyl, $(C_3-C_7)$-cycloalkyl and 4- to 7-membered heterocycloalkyl, wherein (i) said $(C_3-C_7)$-cycloalkyl and 4- to 7-membered heterocycloalkyl are optionally substituted with one or two substituents independently selected from the group consisting of fluoro, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino and di-$(C_1-C_4)$-alkylamino, and (ii) said $(C_1-C_6)$-alkyl is optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, $(C_3-C_7)$-cycloalkyl, phenyl, 4- to 7-membered heterocycloalkyl and 5- to 10-membered heteroaryl, wherein said $(C_3-C_7)$-cycloalkyl, phenyl, 4- to 7-membered heterocycloalkyl and 5- to 10-membered heteroaryl substituents in turn are optionally substituted with one or two residues independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino and di-$(C_1-C_4)$-alkylamino, $R^2$ is hydrogen, fluoro, chloro or methyl, $R^3$ is hydrogen, $(C_1-C_4)$-alkyl or cyclopropyl, $R^4$ is cyano or aminocarbonyl, $R^5$ is selected from the group consisting of $(C_1-C_6)$-alkyl, $(C_3-C_7)$-cycloalkyl, phenyl and 5- or 6-membered heteroaryl, wherein (i) said $(C_3-C_7)$-cycloalkyl, phenyl and 5- or 6-membered heteroaryl are optionally substituted with one or two substituents independently selected from the group consisting of fluoro, chloro, bromo, cyano, difluoromethyl, trifluoromethyl, $(C_1-C_4)$-alkyl, hydroxy, difluoromethoxy, trifluoromethoxy, $(C_1-C_4)$-alkoxy, amino, mono-$(C_1-C_4)$-alkylamino and di-$(C_1-C_4)$-alkylamino, and (ii) said $(C_1-C_6)$-alkyl is optionally substituted with up to three fluoro atoms or with one or two substituents independently selected from the group consisting of trifluoromethyl, hydroxy, $(C_1-C_4)$-alkoxy, amino, mono-$(C_1-C_4)$-alkylamino, di-$(C_1-C_4)$-alkylamino, $(C_3-C_7)$-cycloalkyl, phenyl, 4- to 7-membered heterocycloalkyl and 5- or 6-membered heteroaryl, wherein the alkyl groups of said $(C_1-C_4)$-alkoxy, mono-$(C_1-C_4)$-alkylamino and di-$(C_1-C_4)$-alkylamino substituents in turn are optionally substituted with up to three fluoro atoms or with one or two residues independently selected from the group consisting of trifluoromethyl, hydroxy, $(C_1-C_4)$-alkoxy, amino, mono-$(C_1-C_4)$-alkylamino, di-$(C_1-C_4)$-alkylamino and 4- to 7-membered heterocycloalkyl, and wherein said $(C_3-C_7)$-cycloalkyl, phenyl, 4- to 7-membered heterocycloalkyl and 5- or 6-membered heteroaryl groups in turn are optionally substituted with one or two residues independently selected from the group consisting of fluoro, chloro, cyano, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino, or $R^5$ is $(C_1-C_4)$-alkoxycarbonyl, aminocarbonyl, mono-$(C_1-C_4)$-alkylaminocarbonyl or di-$(C_1-C_4)$-alcylaminocarbonyl, or $R^3$ and $R^5$ are joined and, taken together with the nitrogen and the carbon atom to which they are attached, form a fused ring of the formula

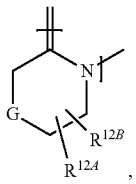

wherein

G is —$CH_2$—, —$C(CH_3)_2$—, —$CH(CF_3)$—, —O— or —$NR^{11}$—, wherein $R^{11}$ is hydrogen or $(C_1-C_4)$-alkyl, and $R^{12A}$ and $R^{12B}$ are independently hydrogen or fluoro, or $R^4$ and $R^5$ are joined and, taken together with the carbon atoms to which they are attached, form a fused lactone or lactame ring of the formula

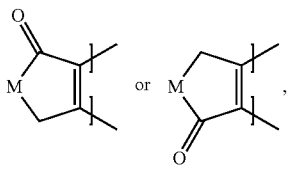

wherein

M is —O— or —$NR^{13}$—, wherein $R^{13}$ is hydrogen or $(C_1-C_4)$-alkyl.

The compounds according to this invention can also be present in the form of their salts, hydrates and/or solvates.

Salts for the purposes of the present invention are preferably pharmaceutically acceptable salts of the compounds according to the invention (for example, see S. M. Berge et al., "Pharmaceutical Salts", *J. Pharm. Sci.* 1977, 66, 1-19).

Pharmaceutically acceptable salts include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid.

Pharmaceutically acceptable salts also include salts of customary bases, such as for example and preferably alkali metal salts (for example sodium and potassium salts), alkaline earth metal salts (for example calcium and magnesium salts), and ammonium salts derived from ammonia or organic amines, such as illustratively and preferably ethylamine, diethylamine, triethylamine, ethyldiisopropylamine, monoethanolamine, diethanolamine, triethanolamine, dicyclohexylamine, dimethylaminoethanol, dibenzylamine, N-methylmorpholine, N-methylpiperidine, dihydroabietylamine, arginine, lysine, and ethylenediamine.

Hydrates of the compounds of the invention or their salts are stoichiometric compositions of the compounds with water, such as, for example, hemi-, mono-, or dihydrates.

Solvates of the compounds of the invention or their salts are stoichiometric compositions of the compounds with solvents.

The compounds of this invention may, either by nature of asymmetric centers or by restricted rotation, be present in the form of isomers (enantiomers, diastereomers). Any isomer may be present in which the asymmetric center is in the (R)-, (S)-, or (R,S) configuration.

It will also be appreciated that when two or more asymmetric centers are present in the compounds of the invention, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the invention.

Geometric isomers by nature of substituents about a double bond or a ring may be present in cis (=Z—) or trans (=E—) form, and both isomeric forms are encompassed within the scope of this invention.

All isomers, whether separated, pure, partially pure, or in racemic mixture, of the compounds of this invention are encompassed within the scope of this invention. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by resolution.

In addition, all possible tautomeric forms of the compounds described above are included according to the present invention.

Unless otherwise stated, the following definitions apply for the substituents and residues used throughout this specification and claims:

Alkyl in general represents a straight-chain or branched saturated hydrocarbon radical having 1 to 6, preferably 1 to 4, more preferably 1 to 3 carbon atoms. Non-limiting examples include methyl, ethyl, n-propyl, isopropyl, n-butyl, isobutyl, sec.-butyl, tert.-butyl, pentyl, isopentyl, neopentyl, hexyl, isohexyl. The same applies to radicals such as alkoxy, monoalkylamino, dialkylamino, and the like.

Alkoxy illustratively and preferably represents methoxy, ethoxy, n-propoxy, isopropoxy, n-butoxy and tert.-butoxy. The same applies to radicals such as alkoxycarbonyl.

Alkoxycarbonyl illustratively and preferably represents methoxycarbonyl, ethoxycarbonyl, n-propoxycarbonyl, isopropoxycarbonyl, n-butoxycarbonyl and tert.-butoxycarbonyl.

Monoalkylamino in general represents an amino radical having one alkyl residue attached to the nitrogen atom. Non-limiting examples include methylamino, ethylamino, n-propylamino, isopropylamino, n-butylamino, tert.-butylamino. The same applies to radicals such as monoalkylaminocarbonyl.

Dialkylamino in general represents an amino radical having two independently selected alkyl residues attached to the nitrogen atom. Non-limiting examples include N,N-dimethylamino, N,N-diethylamino, N,N-diisopropylamino, N-ethyl-N-methylamino, N-methyl-N-n-propylamino, N-isopropyl- N-n-propylamino, N-tert.-butyl-N-methylamino. The same applies to radicals such as dialkylaminocarbonyl.

Monoalkylaminocarbonyl illustratively and preferably represents methylaminocarbonyl, ethylaminocarbonyl, n-propylaminocarbonyl, isopropylaminocarbonyl, n-butylaminocarbonyl and tert.-butylaminocarbonyl.

Dialkylaminocarbonyl illustratively and preferably represents N,N-dimethylaminocarbonyl, N,N-diethylaminocarbonyl, N,N-diisopropylaminocarbonyl, N-ethyl-N-methylaminocarbonyl, N-methyl-N-n-propylaminocarbonyl, N-isopropyl-N-n-propylaminocarbonyl and N-tert.-butyl-N-methylaminocarbonyl.

Cycloalkyl in general represents a mono- or bicyclic saturated hydrocarbon radical having 3 to 7, preferably 3 to 6 carbon atoms. Preference is given to monocyclic cycloalkyl radicals. Non-limiting examples include cyclopropyl, cyclobutyl, cyclopentyl, cyclohexyl, cycloheptyl, bicyclo[2.2.1]heptyl.

Heterocycloalkyl in general represents a mono- or bicyclic, saturated heterocyclic radical having a total number of 4 to 7, preferably 4 to 6 ring atoms, including 3 to 6, preferably 3 to 5 carbon atoms and up to 2 heteroatoms and/or hetero-groups independently selected from the group consisting of N, O, S, SO and $SO_2$, which ring system can be bonded via a ring carbon atom or, if possible, via a ring nitrogen atom. Non-limiting examples include azetidinyl, oxetanyl, thietanyl, pyrrolidinyl, pyrazolidinyl, tetrahydrofuranyl, thiolanyl, sulfolanyl, 1,3-dioxolanyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, morpholinyl, thiomorpholinyl, 1,1-dioxidothiomorpholinyl, perhydroazepinyl, perhydro-1,4-diazepinyl, perhydro-1,4-oxazepinyl, 7-azabicyclo[2.2.1]heptyl, 3-azabicyclo-[3.2.0]heptyl, 7-azabicyclo[4.1.0]heptyl, 2,5-diazabicyclo[2.2.1]heptyl, 2-oxa-5-azabicyclo[2.2.1]-heptyl. Preference is given to 4- to 6-membered monocyclic heterocycloalkyl radicals having up to 2 heteroatoms selected from the group consisting of N and O, such as illustratively and preferably azetidinyl, oxetanyl, tetrahydrofuranyl, 1,3-dioxolanyl, pyrrolidinyl, tetrahydropyranyl, 1,4-dioxanyl, piperidinyl, piperazinyl and morpholinyl.

Azetidino, pyrrolidino, piperidino, piperazino or morpholino specifically refers to the respective heterocycloalkyl radical bonded to the rest of the molecule via a ring nitrogen atom.

Heteroaryl in general represents a mono- or bicyclic, aromatic heterocyclic radical having a total number of 5 to 10 ring atoms, including 2 to 9 carbon atoms and up to 3 heteroatoms independently selected from the group consisting of N, O and S, which ring system can be bonded via a ring carbon atom or, if possible, via a ring nitrogen atom. Non-limiting examples include furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, benzothiadiazolyl, indolyl, isoindolyl, indazolyl, quinolinyl, isoquinolinyl, naphthyridinyl, quinazolinyl, quinoxalinyl, phthalazinyl, imidazopyridinyl, pyrazolopyridinyl, pyrrolopyrimidinyl. Preference is given to 6-membered heteroaryl radicals having up to 2 nitrogen atoms, such as pyridyl, pyrimidyl, pyridazinyl and pyrazinyl, and to 5-membered heteroaryl radicals having up to 2 heteroatoms selected from the group consisting of N, O and S, such as illustratively and preferably thienyl, furyl, pyrrolyl, pyrazolyl, imidazolyl, thiazolyl, oxazolyl, isothiazolyl and isoxazolyl.

Halogen represents radicals of fluorine, chlorine, bromine and iodine. Preference is given to radicals of fluorine and chlorine.

Oxo represents a doubly bonded oxygen atom.

Throughout this document, for the sake of simplicity, the use of singular language is given preference over plural language, but is generally meant to include the plural language if not otherwise stated. E.g., the expression "A method of treating a disease in a patient, comprising administering to a patient an effective amount of a compound of formula (I)" is meant to include the simultaneous treatment of more than one disease as well as the administration of more than one compound of formula (I).

In a preferred embodiment, the present invention relates to compounds of general formula (I), wherein A is —S(=O)$_2$— and D is —CH$_2$—.

In another preferred embodiment, the present invention relates to compounds of general formula (I), wherein
A is —C(=O)—
and
D is —CH$_2$—, —O— or —NR$^7$—, wherein
R$^7$ is hydrogen or (C$_1$-C$_4$)-alkyl.

In a further preferred embodiment, the present invention relates to compounds of general formula (I), wherein
E is —CR$^{8A}$R$^{8B}$—, wherein
R$^{8A}$ and R$^{8B}$ are independently hydrogen or (C$_1$-C$_4$)-alkyl, or
R$^{8A}$ and R$^{8B}$ are joined and, taken together with the carbon atom to which they are attached, form a cyclopropyl ring.

In yet another preferred embodiment, the present invention relates to compounds of general formula (I), wherein R$^4$ is cyano.

In a more preferred embodiment, the present invention relates to compounds of general formula (I), wherein
A is —C(=O)—,
D is —CH$_2$—, —O—, —NH— or —N(CH$_3$)—,
E is —CR$^{8A}$R$^{8B}$— or *—CR$^{8A}$R$^{8B}$—CH$_2$—**, wherein
* denotes the link to the dihydropyridine ring,
** denotes the link to the D group,
and
R$^{8A}$ and R$^{8B}$ are independently hydrogen or methyl,
or
R$^{8A}$ and R$^{8B}$ are joined and, taken together with the carbon atom to which they are attached, form a cyclopropyl ring,
R$^1$ is selected from the group consisting of hydrogen, (C$_1$-C$_6$)-alkyl, (C$_3$-C$_6$)-cycloalkyl, phenyl, 4- to 6-membered heterocycloalkyl and 5- or 6-membered heteroaryl, wherein
(i) said (C$_3$-C$_6$)-cycloalkyl, phenyl, 4- to 6-membered heterocycloalkyl and 5- or 6-membered heteroaryl are optionally substituted with one or two substituents independently selected from the group consisting of fluoro, chloro, difluoromethyl, trifluoromethyl, (C$_1$-C$_4$)-alkyl, oxo, hydroxy, difluoromethoxy, trifluoromethoxy, (C$_1$-C$_4$)-alkoxy, amino, mono-(C$_1$-C$_4$)-alkylamino, di-(C$_1$-C$_4$)-alkylamino and 4- to 6-membered heterocycloalkyl, wherein the alkyl groups of said (C$_1$-C$_4$)-alkoxy, mono-(C$_1$-C$_4$)-alkylamino and di-(C$_1$-C$_4$)-alkylamino substituents in turn are optionally substituted with hydroxy, methoxy or ethoxy,
and
(ii) said (C$_1$-C$_6$)-alkyl is optionally substituted with one, two or three substituents independently selected from the group consisting of fluoro, trifluoromethyl, hydroxy, (C$_1$-C$_4$)-alkoxy, amino, mono-(C$_1$-C$_4$)-alkylamino, di- ($C_1$-$C_4$)-alkylamino, ($C_3$-$C_6$)-cycloalkyl, 4- to 6-membered heterocycloalkyl and 5- or 6-membered heteroaryl,
wherein said ($C_3$-$C_6$)-cycloalkyl, 4- to 6-membered heterocycloalkyl and 5- or 6-membered heteroaryl substituents in turn are optionally substituted with one or two residues independently selected from the group consisting of fluoro, chloro, difluoromethyl, trifluoromethyl, ($C_1$-$C_4$)-alkyl, oxo, hydroxy, ($C_1$-$C_4$)-alkoxy, amino, mono-($C_1$-$C_4$)-alkylamino and di-($C_1$-$C_4$)-alkylamino, or $R^1$ is a group of the formula —$NR^{9A}R^{9B}$ or —$OR^{10}$, wherein
$R^{9A}$ is hydrogen or ($C_1$-$C_4$)-alkyl optionally substituted with one or two substituents independently selected from the group consisting of hydroxy, ($C_1$-$C_4$)-alkoxy, amino, mono-($C_1$-$C_4$)-alkylamino and di-($C_1$-$C_4$)-alkylamino,
$R^{9B}$ is selected from the group consisting of hydrogen, ($C_1$-$C_6$)-alkyl, ($C_3$-$C_6$)-cycloalkyl and 4- to 6-membered heterocycloalkyl, wherein
(i) said ($C_3$-$C_6$)-cycloalkyl and 4- to 6-membered heterocycloalkyl are optionally substituted with one or two substituents independently selected from the group consisting of fluoro, difluoromethyl, trifluoromethyl, ($C_1$-$C_4$)-alkyl, oxo, hydroxy, ($C_1$-$C_4$)-alkoxy, amino, mono-($C_1$-$C_4$)-alkylamino and di-($C_1$-$C_4$)-alkylamino,
and
(ii) said ($C_1$-$C_6$)-alkyl is optionally substituted with one, two or three substituents independently selected from the group consisting of fluoro, trifluoromethyl, hydroxy, ($C_1$-$C_4$)-alkoxy, amino, mono-($C_1$-$C_4$)-alkylamino, di-($C_1$-$C_4$)-alkylamino, ($C_3$-$C_6$)-cycloalkyl, 4- to 6-membered heterocycloalkyl and 5- or 6-membered heteroaryl,
wherein said ($C_3$-$C_6$)-cycloalkyl, 4- to 6-membered heterocycloalkyl and 5- or 6-membered heteroaryl substituents in turn are optionally substituted with one or two residues independently selected from the group consisting of fluoro, chloro, difluoromethyl, trifluoromethyl, ($C_1$-$C_4$)-alkyl, oxo, hydroxy, ($C_1$-$C_4$)-alkoxy, amino, mono-($C_1$-$C_4$)-alkylamino and di-($C_1$-$C_4$)-alkylamino, or $R^{9A}$ and $R^{9B}$ are joined and, taken together with the nitrogen atom to which they are attached, form a 4- to 6-membered heterocycloalkyl ring, which may contain a second ring heteroatom selected from N and O, and which is optionally substituted with one or two substituents independently selected from the group consisting of fluoro, ($C_1$-$C_4$)-alkyl, oxo, hydroxy, ($C_1$-$C_4$)-alkoxy, amino, mono-($C_1$-$C_4$)-alkylamino and di-($C_1$-$C_4$)-alkylamino, $R^{10}$ is selected from the group consisting of ($C_1$-$C_6$)-alkyl, ($C_3$-$C_6$)-cycloalkyl and 4- to 6-membered heterocycloalkyl, wherein
(i) said ($C_3$-$C_6$)-cycloalkyl and 4- to 6-membered heterocycloalkyl are optionally substituted with one or two substituents independently selected from the group consisting of fluoro, difluoromethyl, trifluoromethyl, ($C_1$-$C_4$)-alkyl, oxo, hydroxy, ($C_1$-$C_4$)-alkoxy, amino, mono-($C_1$-$C_4$)-alkylamino and di-($C_1$-$C_4$)-alkylamino,
and
(ii) said ($C_1$-$C_6$)-alkyl is optionally substituted with one, two or three substituents independently selected from the group consisting of fluoro, trifluoromethyl, hydroxy, ($C_1$-$C_4$)-alkoxy, amino, mono-($C_1$-$C_4$)-alkylamino, di-($C_1$-$C_4$)-alkylamino, ($C_3$-$C_6$)-cycloalkyl, 4- to 6-membered heterocycloalkyl and 5- or 6-membered heteroaryl,
wherein said ($C_3$-$C_6$)-cycloalkyl, 4- to 6-membered heterocycloalkyl and 5- or 6-membered heteroaryl substituents in turn are optionally substituted with one or two residues independently selected from the group consisting of fluoro, chloro, difluoromethyl, trifluoromethyl, ($C_1$-$C_4$)-alkyl, oxo, hydroxy, ($C_1$-$C_4$)-alkoxy, amino, mono-($C_1$-$C_4$)-alkylamino and di-($C_1$-$C_4$)-alkylamino, $R^2$ is hydrogen or fluoro,
$R^3$ is hydrogen or ($C_1$-$C_4$)-alkyl,
$R^4$ is cyano,
$R^5$ is selected from the group consisting of ($C_1$-$C_4$)-alkyl, cyclopropyl, phenyl and 5- or 6-membered heteroaryl, wherein
(i) said cyclopropyl is optionally substituted with one or two substituents independently selected from the group consisting of fluoro, trifluoromethyl and methyl,
(ii) said phenyl and 5- or 6-membered heteroaryl are optionally substituted with one or two substituents independently selected from the group consisting of fluoro, chloro, cyano, difluoromethyl, trifluoromethyl, ($C_1$-$C_4$)-alkyl and ($C_1$-$C_4$)-alkoxy,
and
(iii) said ($C_1$-$C_4$)-alkyl is optionally substituted with up to three fluoro atoms or with one or two substituents independently selected from the group consisting of ($C_1$-$C_4$)-alkoxy, amino, mono-($C_1$-$C_4$)-alkylamino, di-($C_1$-$C_4$)-alkylamino, ($C_3$-$C_6$)-cycloalkyl, phenyl, 4- to 6-membered heterocycloalkyl and 5-membered heteroaryl,
wherein the alkyl groups of said ($C_1$-$C_4$)-alkoxy, mono-($C_1$-$C_4$)-alkylamino and di-($C_1$-$C_4$)-alkylamino substituents in turn are optionally substituted with up to three fluoro atoms or with one or two residues independently selected from the group consisting of ($C_1$-$C_4$)-alkoxy, amino, mono-($C_1$-$C_4$)-alkylamino, di-($C_1$-$C_4$)-alkylamino and 4- to 6-membered heterocycloalkyl,
and wherein
said ($C_3$-$C_6$)-cycloalkyl, phenyl, 4- to 6-membered heterocycloalkyl and 5-membered heteroaryl groups in turn are optionally substituted with one or two residues independently selected from the group consisting of fluoro, chloro, cyano, trifluoromethyl, ($C_1$-$C_4$)-alkyl, oxo, ($C_1$-$C_4$)-alkoxy, amino, mono-($C_1$-$C_4$)-alkylamino and di-($C_1$-$C_4$)-alkylamino, or $R^3$ and $R^5$ are joined and, taken together with the nitrogen and the carbon atom to which they are attached, form a fused ring of the formula

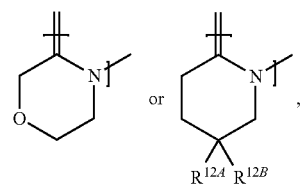

wherein
$R^{12A}$ and $R^{12B}$ are independently hydrogen or fluoro,
or
$R^4$ and $R^5$ are joined and, taken together with the carbon atoms to which they are attached, form a fused lactone ring of the formula

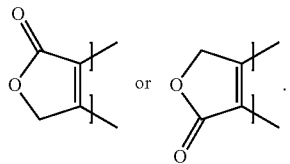

In a particularly preferred embodiment, the present invention relates to compounds of general formula (I), wherein
A is —C(=O)—,
D is —O—,
E is —CH$_2$—, —CH(CH$_3$)— or —C(CH$_3$)$_2$—,
$R^1$ is selected from the group consisting of hydrogen, (C$_1$-C$_4$)-alkyl, phenyl and 5- or 6-membered heteroaryl, wherein
(i) said phenyl and 5- or 6-membered heteroaryl are optionally substituted with one or two substituents independently selected from the group consisting of fluoro, chloro, difluoromethyl, trifluoromethyl, (C$_1$-C$_3$)-alkyl, (C$_1$-C$_3$)-alkoxy, amino, mono-(C$_1$-C$_3$)-alkylamino, di-(C$_1$-C$_3$)-alkylamino and 4- to 6-membered heterocycloalkyl,
wherein the alkyl groups of said (C$_1$-C$_3$)-alkoxy, mono-(C$_1$-C$_3$)-alkylamino and di-(C$_1$-C$_3$)-alkylamino substituents in turn are optionally substituted with methoxy or ethoxy,
and
(ii) said (C$_1$-C$_4$)-alkyl is optionally substituted with up to three fluoro atoms or with one or two substituents independently selected from the group consisting of (C$_1$-C$_3$)-alkoxy, amino, mono-(C$_1$-C$_3$)-alkylamino, di-(C$_1$-C$_3$)-alkylamino and 4- to 6-membered heterocycloalkyl,
wherein said 4- to 6-membered heterocycloalkyl substituent in turn is optionally substituted with one or two residues independently selected from the group consisting of fluoro, trifluoromethyl, methyl, ethyl, oxo, methoxy, ethoxy, amino, methylamino, ethylamino, dimethylamino and diethylamino,
or
$R^1$ is a group of the formula —NR$^{9A}$R$^{9B}$ or —OR$^{10}$, wherein
$R^{9A}$ is hydrogen or (C$_1$-C$_4$)-alkyl optionally substituted with hydroxy, methoxy, ethoxy, amino, methylamino, ethylamino, dimethylamino or diethylamino,
$R^{9B}$ is hydrogen or (C$_1$-C$_4$)-alkyl optionally substituted with up to three fluoro atoms or with one or two substituents independently selected from the group consisting of hydroxy, (C$_1$-C$_3$)-alkoxy, amino, mono-(C$_1$-C$_3$)-alkylamino, di-(C$_1$-C$_3$)-alkylamino and 4- to 6-membered heterocycloalkyl,
wherein said 4- to 6-membered heterocycloalkyl substituent in turn is optionally substituted with one or two residues independently selected from the group consisting of fluoro, trifluoromethyl, methyl, ethyl, oxo, methoxy, ethoxy, amino, methylamino, ethylamino, dimethylamino and diethylamino,
or
$R^{9A}$ and $R^{9B}$ are joined and, taken together with the nitrogen atom to which they are attached, form a 4- to 6-membered heterocycloalkyl ring, which may contain a second ring heteroatom selected from N and O, and which is optionally substituted with one or two substituents independently selected from the group consisting of fluoro, methyl, ethyl, oxo, methoxy, ethoxy, amino, methylamino, ethylamino, dimethylamino and diethylamino,
$R^{10}$ is (C$_1$-C$_4$)-alkyl optionally substituted with up to three fluoro atoms or with one or two substituents independently selected from the group consisting of hydroxy, (C$_1$-C$_3$)-alkoxy, amino, mono-(C$_1$-C$_3$)-alkylamino, di-(C$_1$-C$_3$)-alkylamino and 4- to 6-membered heterocycloalkyl,
wherein said 4- to 6-membered heterocycloalkyl substituent in turn is optionally substituted with one or two residues independently selected from the group consisting of fluoro, trifluoromethyl, methyl, ethyl, oxo, methoxy, ethoxy, amino, methylamino, ethylamino, dimethylamino and diethylamino,
$R^2$ is hydrogen or fluoro,
$R^3$ is hydrogen or methyl,
$R^4$ is cyano,
and
$R^5$ is selected from the group consisting of (C$_1$-C$_4$)-alkyl, phenyl, pyridyl, pyrimidinyl, oxazolyl and isoxazolyl, wherein
(i) said phenyl, pyridyl, pyrimidinyl, oxazolyl and isoxazolyl are optionally substituted with one or two substituents independently selected from the group consisting of fluoro, chloro, difluoromethyl, trifluoromethyl, methyl, ethyl, methoxy and ethoxy,
and
(ii) said (C$_1$-C$_4$)-alkyl is optionally substituted with up to three fluoro atoms or with a substituent selected from the group consisting of (C$_1$-C$_3$)-alkoxy, amino, mono-(C$_1$-C$_3$)-alkylamino, di-(C$_1$-C$_3$)-alkylamino, phenyl, 4- to 6-membered heterocycloalkyl and 5-membered heteroaryl,
wherein said phenyl and 5-membered heteroaryl substituents in turn are optionally substituted with one or two residues independently selected from the group consisting of fluoro, chloro, trifluoromethyl, methyl, ethyl and amino,
and wherein
the alkyl groups of said (C$_1$-C$_3$)-alkoxy, mono-(C$_1$-C$_3$)-alkylamino and di-(C$_1$-C$_3$)-alkylamino substituents in turn are optionally substituted with up to three fluoro atoms or with a residue selected from the group consisting of methoxy, ethoxy, amino, methylamino, ethylamino, dimethylamino, diethylamino, azetidino, pyrrolidino, piperidino, piperazino and morpholino,
and wherein
said 4- to 6-membered heterocycloalkyl substituent as well as said azetidino, pyrrolidino, piperidino, piperazino and morpholino groups in turn are optionally substituted with one or two residues independently selected from the group consisting of fluoro, methyl, ethyl and oxo.

In an especially preferred embodiment, the present invention relates to compounds of general formula (I), wherein
A is —C(=O)—,
D is —O—,
E is —CH$_2$—, $R^1$ is hydrogen, methyl or ethyl,
$R^2$ is hydrogen or fluoro,
$R^3$ is hydrogen or methyl,
$R^4$ is cyano,
and
$R^5$ is $(C_1-C_4)$-alkyl optionally substituted with methoxy, ethoxy or up to three fluoro atoms,
or
is phenyl optionally substituted with one or two substituents independently selected from the group consisting of fluoro, chloro, methyl and trifluoromethyl.

The definitions of residues indicated specifically in the respective combinations or preferred combinations of residues are also replaced as desired by definitions of residues of other combinations, irrespective of the particular combinations indicated for the residues. Combinations of two or more of the abovementioned preferred ranges are particularly preferred.

In another embodiment, the present invention relates to a process for preparing the compounds of general formula (I), wherein $R^3$ is hydrogen, characterized in that an indazolyl aldehyde of formula (II)

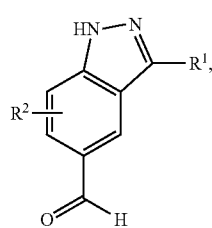

(II)

wherein $R^1$ and $R^2$ have the meanings described above,
is reacted either
[A] with a compound of formula (III)

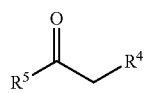

(III)

or a sodium enolate thereof, wherein $R^4$ and $R^5$ have the meanings described above,
in the presence of an acid, an acid/base combination and/or a dehydrating agent to give a compound of formula (IV)

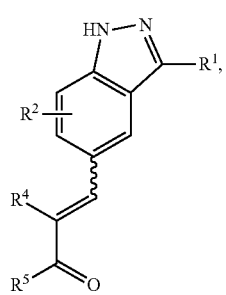

(IV)

wherein $R^1$, $R^2$, $R^4$ and $R^5$ have the meanings described above, and the latter is then condensed with a compound of formula (V)

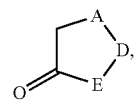

(V)

wherein A, D and E have the meanings described above,
in the presence of an ammonia source such as ammonium acetate to give the compound of formula (I-A)

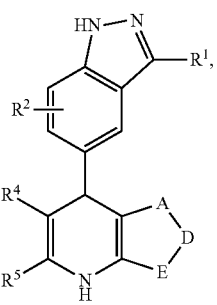

(I-A)

wherein A, D, E, $R^1$, $R^2$, $R^4$ and $R^5$ have the meanings described above,
or
[B] with a compound of formula (V)

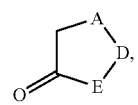

(V)

wherein A, D and E have the meanings described above,
optionally in the presence of a base and/or a dehydrating agent to yield a compound of formula (VI)

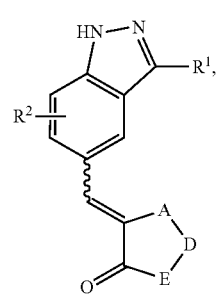

(VI)

wherein A, D, E, $R^1$ and $R^2$ have the meanings described above, and the latter is then condensed with a compound of formula (VII)

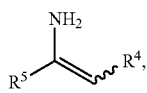
(VII)

wherein R⁴ and R⁵ have the meanings described above, in the presence of an acid to give the compound of formula (I-A)

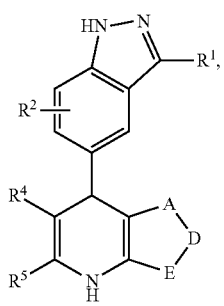
(I-A)

wherein A, D, E, R¹, R², R⁴ and R⁵ have the meanings described above, optionally followed, where appropriate, by (i) separating the compounds (I-A) into their respective enantiomers and/or diastereomers, preferably using chromatographic methods, and/or (ii) converting the compounds (I-A) into their respective hydrates, solvates, salts and/or hydrates or solvates of the salts by treatment with the corresponding solvents and/or acids or bases.

Process steps (II)+(III)→(IV), (IV)+(V)→(I-A), (II)+(V) →(VI) and (VI)+(VII)→(I-A) are generally carried out in an inert solvent at a temperature range from +20° C. to the boiling point of the solvent under atmospheric pressure.

Inert solvents suitable for this purpose are, for example, alcohols such as methanol, ethanol, n-propanol, isopropanol, n-butanol, tert-butanol or n-pentanol, hydrocarbons such as hexane, cyclohexane, benzene, toluene or xylene, halohydrocarbons such as dichloromethane, trichloromethane, tetrachloromethane, trichloroethane, 1,2-dichloroethane, chlorobenzene or chlorotoluene, ethers such as tetrahydrofuran, 1,4-dioxane or 1,2-dimethoxyethane, or other solvents such as acetonitrile or acetic acid. It is likewise possible to use mixtures of these solvents. Reactions (II)+(III)-4 (IV) and (II)+(V)→(VI) are preferably performed in dichloromethane, toluene, ethanol, n-propanol, isopropanol, n-butanol or n-pentanol at the respective reflux temperature under atmospheric pressure, and reactions (IV)+(V)→(I-A) and (VI)+ (VII)→(I-A) are preferably carried out in acetic acid also at reflux temperature under atmospheric pressure.

Reaction (II)+(III)→(IV) can advantageously take place in the presence of an acid, an acid/base combination and/or a dehydrating agent such as, for example, molecular sieves. Examples of suitable acid catalysts are acetic acid, trifluoroacetic acid, methanesulfonic acid or p-toluenesulfonic acid; suitable bases are in particular piperidine or pyridine.

Depending on the reactivity of the components, conversion (II)+(V)→(VI) may be performed without further auxiliary reagents, or it can be facilitated by a customary amine base, such as piperidine, and/or a dehydrating agent, such as molecular sieves. Reactions (IV)+(V)→(I-A) and (VI)+ (VII)→ (I-A) are usually carried out in the presence of an acid; preferably, acetic acid is used both as acid catalyst and solvent.

Suitable ammonia sources for reaction (IV)+(V)→(I-A) are, for example, ammonium formate, ammonium acetate, ammonium chloride or ammonium hydrogensulfate; preference is given to ammonium acetate [for the synthesis of 1,4-dihydropyridines in general, see, for example, D. M. Stout, A. I. Meyers, Chem. Rev. 1982, 82, 223-243; H. Meier et al., Liebigs Ann. Chem. 1977, 1888; H. Meier et al., ibid. 1977, 1895; H. Meier et al., ibid. 1976, 1762; F. Bossert et al., Angew. Chem. 1981, 93, 755].

Compounds of the invention having the formula (I-B)

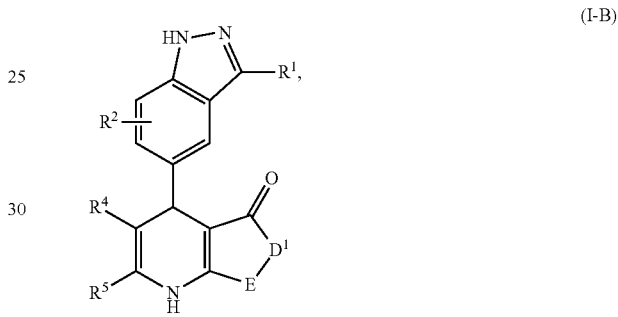
(I-B)

wherein E, R¹, R², R⁴ and R⁵ have the meanings described above, and

D¹ represents —O— or —NR⁷—, wherein R⁷ has the meaning described above, may also be prepared by a three-component condensation reaction of the indazolyl aldehyde (II)

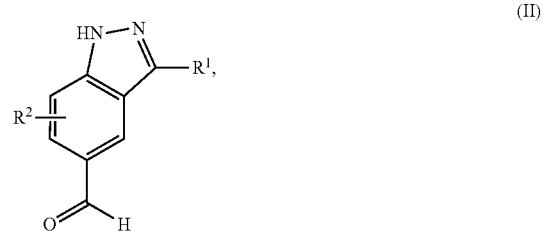
(II)

wherein R¹ and R² have the meanings described above, with an enamine of formula (VII)

(VII)

wherein $R^4$ and $R^5$ have the meanings described above,
and a compound of formula (VIII)

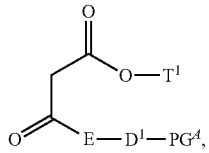

(VIII)

wherein E and $D^1$ have the meanings described above,
$T^1$ represents $(C_1-C_4)$-alkyl,
and
$PG^A$ represents a suitable hydroxy- or amino-protecting group, such as acetyl, trimethylsilyl, tetrahydropyranyl, tert-butoxycarbonyl or benzyloxycarbonyl, respectively,
to give an intermediate compound of formula (IX)

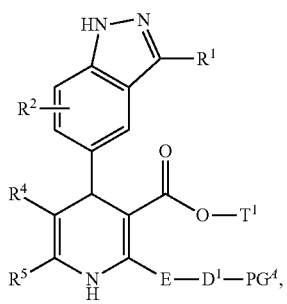

(IX)

wherein $D^1$, E, $PG^A$, $T^1$, $R^1$, $R^2$, $R^4$ and $R^5$ have the meanings described above,
which is then deprotected and cyclized to yield the target compound of formula (I-B).

The condensation reaction (II)+(VII)+(VIII)→(IX) is preferably carried out in an alcoholic solvent such as methanol, ethanol, n-propanol, isopropanol, n-butanol, tert-butanol or n-pentanol, optionally in combination with an acid catalyst such as acetic acid. The conversion is generally performed at a temperature range from +20° C. to +150° C., preferably from +80° C. to +120° C., under atmospheric pressure.

The removal of the protecting group $PG^A$ in process step (IX)→(I-B) is generally carried out by standard methods well known in the art [see, for example, T. W. Greene and P. G. M. Wuts, *Protective Groups in Organic Synthesis*, Wiley, New York, 1999]. As a hydroxy-protecting group, acetyl is preferably used. In this case, deprotection and subsequent lactone formation [$D^1$=O in (I-B)] may be accomplished in a one-pot procedure, i.e. without isolation of the deprotected intermediate, by treating the compound (IX) with an aqueous solution of a strong acid, such as hydrogen chloride, hydrogen bromide or trifluoroacetic acid, at elevated temperature (e.g. from +50° C. to +120° C.).

For nitrogen protection, tert-butoxycarbonyl (Boc) is preferably employed as group $PG^A$. Deprotection by standard treatment with anhydrous hydrogen chloride or trifluoroacetic acid, and final cyclization to lactame (I-B) [$D^1$=$NR^7$] by exposing the intermediate amine salt to a customary base may again be performed using a one-pot procedure or in two separate steps.

Compounds of formula (I), wherein $R^3$ is $(C_1-C_4)$-alkyl or cyclopropyl, can be prepared by converting the compound of formula (I-A) by standard methods first into the indazole $N^1$-protected derivative of formula (X)

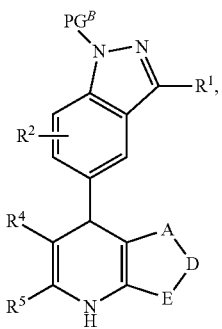

(X)

wherein A, D, E, $R^1$, $R^2$, $R^4$ and $R^5$ have the meanings described above,
and
$PG^B$ represents a suitable indazole-protecting group, such as tert-butoxycarbonyl, 2-(trimethylsilyl)ethoxymethyl or p-methoxybenzyl,
followed by dihydropyridine N-alkylation with a compound of formula (XI)

$$R^{3A}-Z \quad (XI),$$

wherein
$R^{3A}$ represents $(C_1-C_4)$-alkyl or cyclopropyl,
and
Z represents a leaving group such as halogen, mesylate, triflate or tosylate,
in the presence of a base to afford a compound of formula (XII)

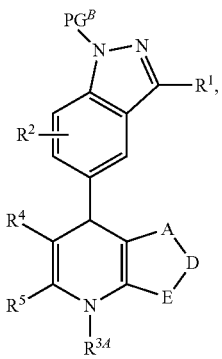

(XII)

wherein A, D, E, $PG^B$, $R^1$, $R^2$, $R^{3A}$, $R^4$ and $R^5$ have the meanings described above,
and subsequent removal of the protecting group $PG^B$ using standard procedures to give the compound of formula (I-C)

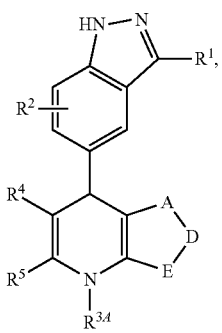

(I-C)

wherein A, D, E, $R^1$, $R^2$, $R^{3A}$, $R^4$ and $R^5$ have the meanings described above.

Introduction and removal of the indazole-protecting group $PG^B$ in process steps (I-A)→(X) and (XII)→(I-C), respectively, is generally carried out by standard methods well known in the art [see, for example, T. W. Greene and P. G. M. Wuts, *Protective Groups in Organic Synthesis*, Wiley, New York, 1999; M. Bodanszky and A. Bodanszky, *The Practice of Peptide Synthesis*, Springer-Verlag, Berlin, 1984]. Preferably used as protecting group in the above process is tert-butoxycarbonyl (Boc), 2-(trimethylsilyl)ethoxymethyl (SEM) or p-methoxybenzyl (PMB). The removal of these groups is preferably carried out by reacting with a strong acid such as hydrogen chloride, hydrogen bromide or trifluoroacetic acid in an inert solvent such as water, dioxane, dichloromethane or acetic acid; it is also possible, where appropriate, for the removal to be carried out without an additional inert solvent. When using the SEM group for indazole protection, cleavage may alternatively be accomplished by treatment with a fluoride source such as potassium fluoride or tetrabutylammonium fluoride in an inert solvent such as tetrahydrofuran.

In some cases, however, it may be more convenient to perform the dihydropyridine N-alkylation step without prior blockade of the indazole $N^1$-nitrogen, and to separate product mixtures that may result preferably using chromatographic methods.

Inert solvents for the alkylation reaction (X)+(XI)→(XII) are, for example, ethers such as diethyl ether, methyl tert-butyl ether, tetrahydrofuran, 1,4-dioxane or 1,2-dimethoxyethane, hydrocarbons such as benzene, toluene, xylene, hexane or cyclohexane, halohydrocarbons such as dichloromethane, trichloromethane, tetrachloromethane, 1,2-dichloroethane, trichloroethane, tetrachloroethane, chlorobenzene or chlorotoluene, or other solvents such as acetonitrile, N,N-dimethylformamide (DMF), dimethyl sulfoxide (DMSO), N,N'-dimethylpropylene urea (DMPU), N-methylpyrrolidinone (NMP) or pyridine. It is also possible to use mixtures of these solvents. Dichloromethane, tetrahydrofuran, dimethylformamide or mixtures thereof are preferably employed.

Bases suitable for process step (X)+(XI)→(XII) are in particular alkali metal or alkaline earth metal carbonates such as lithium, sodium, potassium, calcium or caesium carbonate, alkali metal hydrides such as sodium or potassium hydride, sterically hindered alkali alkoxides such as sodium or potassium tert-butoxide, sterically hindered alkali amides such as lithium, sodium or potassium bis(trimethylsilyl)amide or lithium diisopropylamide, or organic amines such as triethylamine, N-methylmorpholine, N-methylpiperidine, N,N-diisopropylethylamine or pyridine. Potassium carbonate, caesium carbonate, sodium hydride or triethylamine are preferably used.

The reaction (X)+(XI)→(XII) is generally performed under atmospheric pressure at a temperature range from −20° C. to +120° C., preferably at 0° C. to +80° C.

Compounds of the invention having the formula (I-D)

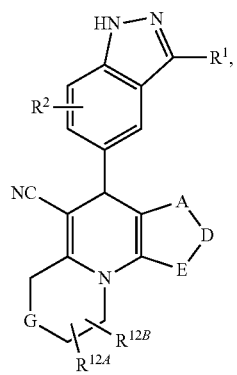

(I-D)

wherein A, D, E, G, $R^1$, $R^2$, $R^{12A}$ and $R^{12B}$ have the meanings described above, can be prepared in close analogy to the condensation reactions described above by substituting the compound of formula (XIII)

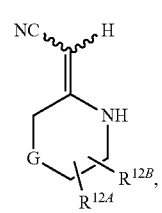

(XIII)

wherein G, $R^{12A}$ and $R^{12B}$ have the meanings described above, for the compound of formula (VII) [cf. transformations (VI)+(VII)→(I-A) and (II)+(VII)+(VIII)→(IX), respectively]. Reaction parameters listed above, such as solvents and acid catalysts, are applied correspondingly.

The compound of formula (XIII) may be prepared starting from a lactam of formula (XIV)

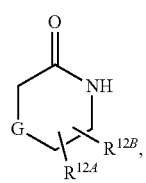

(XIV)

wherein G, $R^{12A}$ and $R^{12B}$ have the meanings described above, which is first condensed via its lactim ether derivative of formula (XV)

(XV)

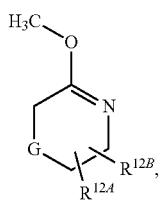

wherein G, $R^{12A}$ and $R^{12B}$ have the meanings described above,
with a cyanoacetate of formula (XVI)

(XVI)

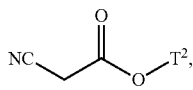

wherein
$T^2$ represents $(C_1-C_4)$-alkyl or benzyl,
to give a compound of formula (XVII)

(XVII)

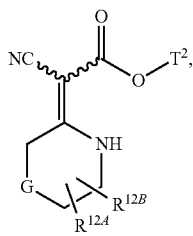

wherein G, $T^2$, $R^{12A}$ and $R^{12B}$ have the meanings described above,
which upon ester cleavage and decarboxylation yields the cyano-enamine of formula (XIII) [see reaction scheme 4 below]. This intermediate is usually employed in the subsequent reactions as a solution of the crude material, i.e. without further isolation and purification.

If expedient, further compounds of formula (I) according to the invention can also be prepared by transformations of functional groups of individual substituents, in particular those listed under $R^1$ and $R^5$, starting with other compounds of formula (I) obtained by the above processes. These transformations are carried out according to customary methods known to the person skilled in the art and include, for example, reactions such as nucleophilic or electrophilic substitution reactions, transition metal-mediated coupling reactions (for example Suzuki or Heck reactions), oxidation, reduction, hydrogenation, halogenation, alkylation, acylation, amination, hydroxylation, etherification, esterification, ester cleavage and ester hydrolysis, formation of nitriles, carboxamides and carbamates, and also the introduction and removal of temporary protective groups.

For example, a compound of the formula (I-B1)

(I-B1)

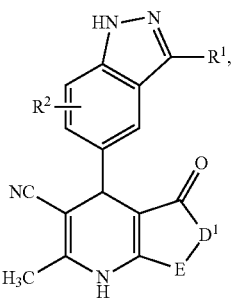

wherein $D^1$, E, $R^1$ and $R^2$ have the meanings described above, may be converted into the bromo derivative of formula (XVIII)

(XVIII)

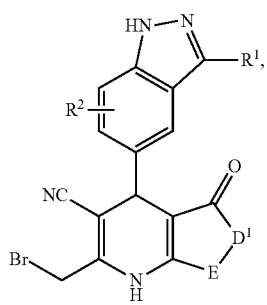

wherein $D^1$, E, $R^1$ and $R^2$ have the meanings described above, by treatment with N-bromosuccinimide and then reacted with an alcohol (R—OH) or amine (R—NH—R') component in the presence of a base to yield substituted analogs of formula (I-B2) and (I-B3), respectively, (I-B2)

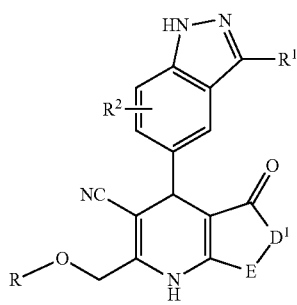

(I-B3)

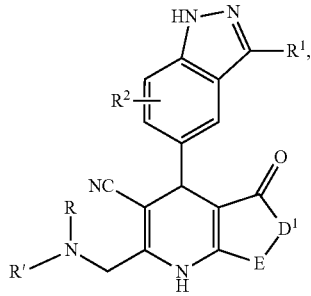

wherein $D^1$, E, $R^1$ and $R^2$ have the meanings described above, and

R and R' represent optionally substituted $(C_1-C_4)$-alkyl groups as defined above in the $R^5$ section.

The compounds of formula (II) are known from the literature or can be prepared from readily available starting materials by adaptation of standard methods described in the literature [see, for example, G. Luo et al., *J. Org. Chem.* 71, 5392 (2006), and procedures described in WO 2007/124288-A1, WO 2005/056550-A2, US 2005/0227968-A1 and EP 1 510 516-A1]. In one synthetic route, the parent indazolyl aldehyde of formula (XIX)

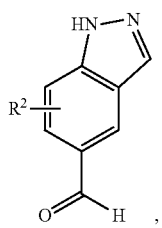

(XIX)

wherein $R^2$ has the meaning described above, is first halogenated in 3-position and converted into the di-protected derivative of formula (XX)

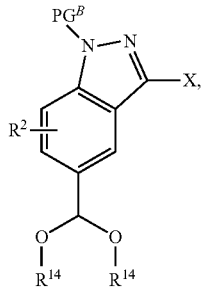

(XX)

wherein $PG^B$ and $R^2$ have the meanings described above,

X represents chloro, bromo or iodo, and $R^{14}$ represents $(C_1-C_4)$-alkyl, or both $R^{14}$ residues together form a —$(CH_2)_2$— or —$(CH_2)_3$— bridge, using standard procedures, and the compound of formula (XX) is then coupled by means of a suitable transition metal catalyst, preferably employing copper or palladium catalysts, either

[C] with a compound of formula (XXI)

$R^{14}$—H (XXI), wherein $R^{1A}$ represents an N- or O-linked $R^1$ residue of the formula —$NR^{9A}R^{9B}$ or —$OR^{10}$, respectively, as defined above, to yield a compound of formula (XXII-A)

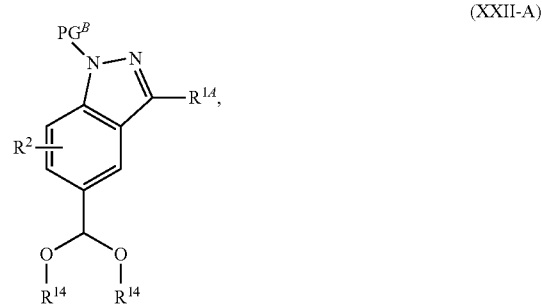

(XXII-A)

wherein $PG^B$, $R^{1A}$, $R^2$ and $R^{14}$ have the meanings described above, or

[D] with a compound of formula (XXIII)

$R^{1B}$-Q (XXIII), wherein $R^{1B}$ represents an optionally substituted C-linked $R^1$ residue selected from the group consisting of $(C_1-C_6)$-alkyl, $(C_3-C_7)$-cycloalkyl, phenyl, 4- to 7-membered heterocycloalkyl, 5- to 10-membered heteroaryl and benzo-1,4-dioxanyl, as defined above, and Q represents a —$B(OR^{15})_2$, —MgHal, —ZnHal or —Sn$(R^{16})_3$ group, wherein Hal is halogen, especially chloro, bromo or iodo, $R^{15}$ is hydrogen or $(C_1-C_4)$-alkyl, or both $R^{15}$ residues together form a —$(CH_2)_2$—, —$C(CH_3)_2$—$C(CH_3)_2$—, —$(CH_2)_3$— or —$CH_2$—$C(CH_3)_2$—$CH_2$— bridge, and $R^{16}$ is $(C_1-C_4)$-alkyl, to afford a compound of formula (XXII-B)

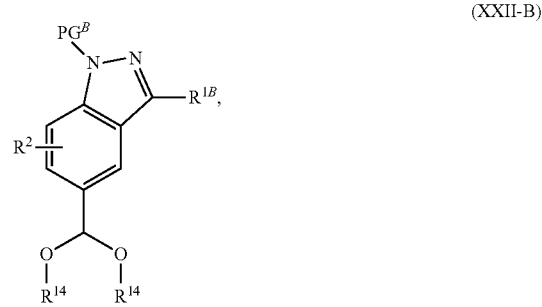

(XXII-B)

wherein $PG^B$, $R^{1B}$, $R^2$ and $R^{14}$ have the meanings described above, and finally the protecting groups are sequentially or simultaneously removed using standard methods to give the 3-substituted indazolyl aldehydes of formula (II-A) and (II-B), respectively,

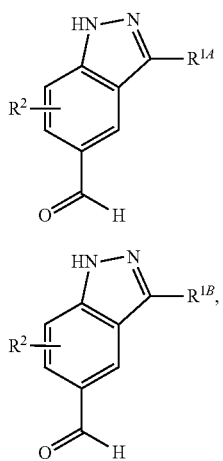

wherein $R^{1A}$, $R^{1B}$ and $R^2$ have the meanings described above.

Inert solvents suitable for process steps (XX)+(XXI) (XXII-A) and (XX)+(XXIII)→(XXII-B) include, for example, aromatic hydrocarbons such as benzene, toluene and xylene, ethers such as diethyl ether, diisopropyl ether, methyl tert-butyl ether, 1,2-dimethoxyethane, tetrahydrofuran, 1,4-dioxane and bis-(2-methoxyethyl)-ether, or dipolar-aprotic solvents such as acetonitrile, dimethylsulfoxide (DMSO), N,N-dimethylformamide (DMF), N,N-dimethylacetamide (DMA), N-methylpyrrolidinone (NMP), N,N'-dimethylpropylene urea (DMPU) and pyridine. Employing mixtures of these solvents is also possible. Preferred solvents are toluene, tetrahydrofuran, 1,4-dioxane, N,N-dimethylformamide and mixtures thereof.

The coupling reactions (XX)+(XXI)→(XXII-A) and (XX)+(XXIII)→(XXII-B) are carried out with the aid of a transition metal catalyst. Suitable for this purpose are in particular copper catalysts such as copper(I) iodide, and palladium catalysts such as palladium on activated charcoal, bis(dibenzylideneacetone)-palladium(0), tris(dibenzylideneacetone)-dipalladium(0), tetrakis(triphenylphosphine)-palladium(0), palladium(II) acetate, bis(triphenylphosphine)-palladium(II) chloride, bis(acetonitrile)-palladium(II) chloride or [1,1'-bis(diphenylphosphino) ferrocene]-palladium(II) chloride, optionally in combination with additional phosphane ligands such as, for example, dicyclohexyl[2',4',6'-tris(1-methylethyl)biphenyl-2-yl]phosphane (XPHOS) or 4,5-bis(diphenylphosphino)-9,9-dimethylxanthene (Xantphos) [see, for example, J. Hassan et al., *Chem. Rev.* 102, 1359-1469 (2002); V. Farina, V. Krishnamurthy and W. J. Scott, in: *The Stille Reaction*, Wiley, New York, 1998].

Process steps (XX)+(XXI)→(XXII-A) and (XX)+(XXIII)→(XXII-B) are usually performed at a temperature range from +20° C. to +200° C., preferably from +80° C. to +180° C., at atmospheric pressure. However, it is also possible to run these reactions at elevated pressure or at reduced pressure (for example in a range from 0.5 to 5 bar). Furthermore, said transformations can advantageously be carried out by means of concomitant microwave irradiation.

Alternatively, such indazole coupling reactions may be carried out at a later stage in the preparation process, employing compounds of formula (I-A) or (I-C), for example, as precursors wherein $R^1$ is chloro or bromo [see reaction scheme 6 below]. The reaction parameters described above for transformations (XX)+(XXI)→(XXII-A) and (XX)+ (XXIII)→(XXII-B), such as solvents and catalysts, are applied analogously. In some cases, depending on specific reaction conditions and reagents, these coupling reactions can be carried out directly, i.e. without prior protection of the indazole $N^1$-nitrogen.

The compounds of the formulae (BI), (V), (VII), (VIII), (XI), (XIV), (XVI), (XIX), (XXI) and (XXIII) are either commercially available, known from the literature, or can be prepared from readily available starting materials by adaptation of standard methods described in the literature.

The preparation of the compounds of the invention can be illustrated by means of the following synthesis schemes 1-6. More detailed procedures are presented below in the experimental section describing the Examples.

Scheme 1

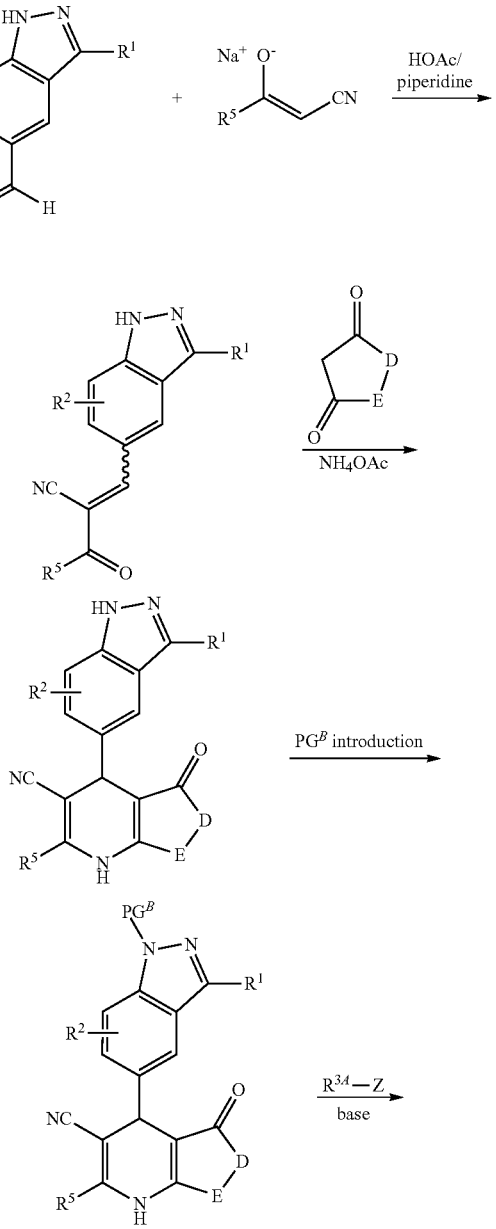

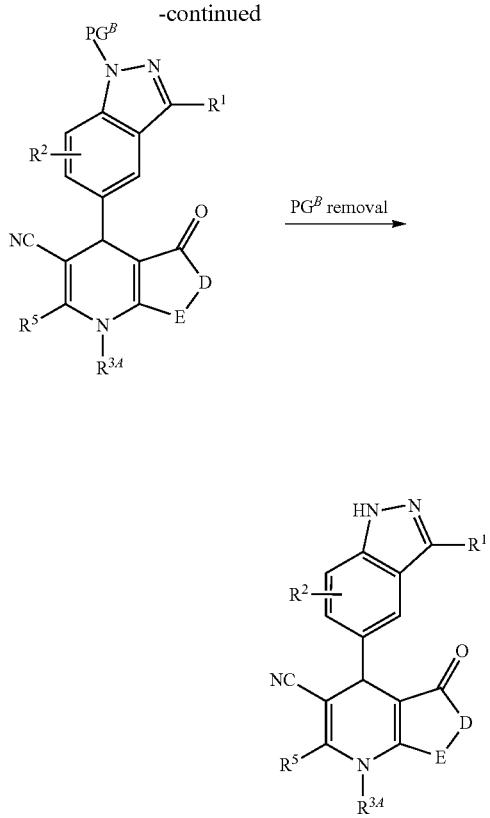
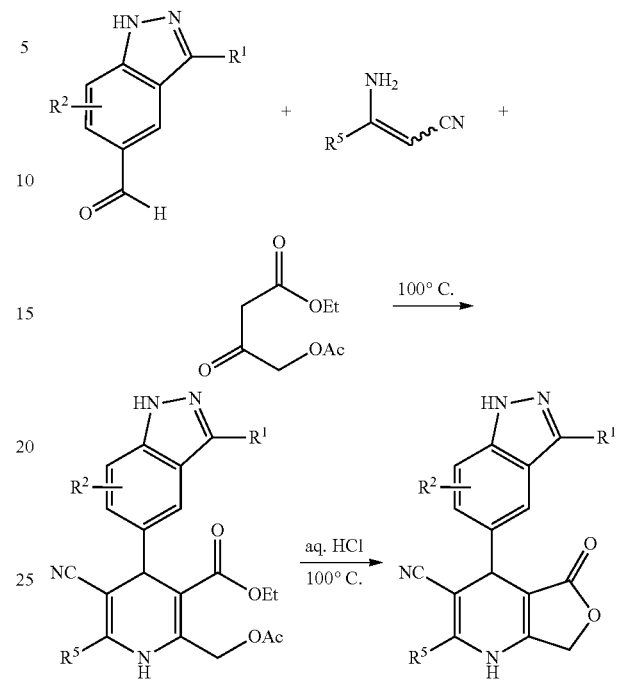
Scheme 3
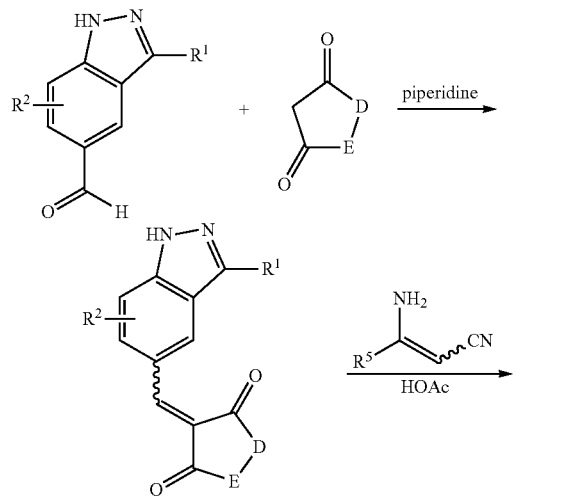
Scheme 2
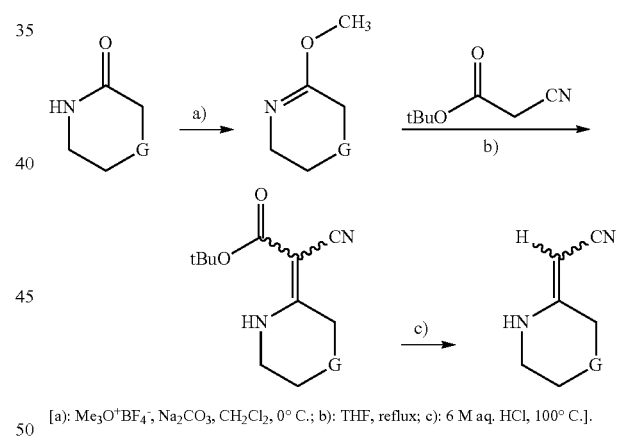
Scheme 4
[a]: Me$_3$O$^+$BF$_4^-$, Na$_2$CO$_3$, CH$_2$Cl$_2$, 0° C.; b): THF, reflux; c): 6 M aq. HCl, 100° C.].
Scheme 5
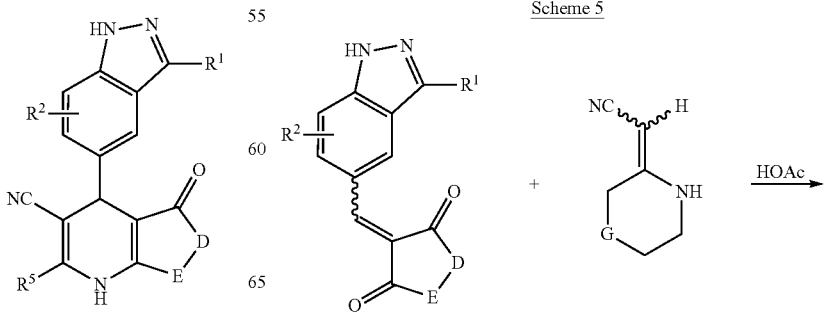

-continued

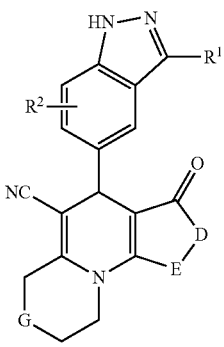

Scheme 6

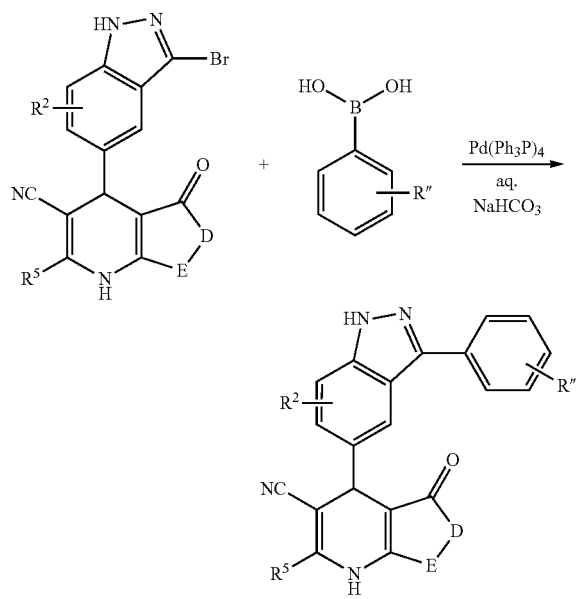

[R″ = hydrogen or substituent as defined above in R¹ section].

Methods of Use

The compounds of the present invention may be used to inhibit the activity or expression of receptor tyrosine kinases, particularly of the c-Met receptor tyrosine kinase. Moreover, the compounds of the present invention exhibit favorable in-vitro clearance properties in liver microsomes and/or hepatocytes. Therefore, the compounds of formula (I) are expected to be valuable as therapeutic agents.

Accordingly, in another embodiment, the present invention provides a method of treating disorders relating to or mediated by c-Met kinase activity in a patient in need of such treatment, comprising administering to the patient an effective amount of a compound of formula (I) as defined above. In certain embodiments, the disorders relating to c-Met kinase activity are cell proliferative disorders, particularly cancer.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The term "disorders relating to or mediated by c-Met" shall include diseases associated with or implicating c-Met activity, for example the hyperactivity of c-Met, and conditions that accompany with these diseases. Examples of "disorders relating to or mediated by c-Met" include disorders resulting from overstimulation of c-Met due to abnormally high amount of c-Met or mutations in c-Met, or disorders resulting from abnormally high amount of c-Met activity due to abnormally high amount of c-Met or mutations in c-Met.

The term "hyperactivity of c-Met" refers to either c-Met expression in cells which normally do not express c-Met or c-Met activity by cells which normally do not possess active c-Met or increased c-Met expression leading to unwanted cell proliferation or mutations leading to constitutive activation of c-Met.

The term "cell proliferative disorder" includes disorders involving the undesired or uncontrolled proliferation of a cell. The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, isomer, polymorph, metabolite, hydrate or solvate thereof which is effective to treat or prevent the disorder.

Cell proliferative or hyper-proliferative disorders in the context of this invention include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral, and hereditary and sporadic papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer, and squamous cell cancer.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present invention include lung fibrosis, atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the present invention include tumor growth, retinopathy, including diabetic retinopathy, ischemic retinal-vein occlusion, retinopathy of prematurity and age-related macular degeneration, rheumatoid arthritis, psoriasis, and bullous disorders associated with sub-epidermal blister formation, including bullous pemphigoid, erythema multiforme and dermatitis herpetiformis.

The compounds of the present invention may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering pharmaceutical compositions of the present invention.

Compounds of formula (I) may be administered as the sole pharmaceutical agent or in combination with one or more additional therapeutic agents where the combination causes no unacceptable adverse effects. This combination therapy includes administration of a single pharmaceutical dosage formulation which contains a compound of formula (I) and one or more additional therapeutic agents, as well as administration of the compound of formula (I) and each additional therapeutic agent in its own separate pharmaceutical dosage formulation. For example, a compound of formula (I) and a therapeutic agent may be administered to the patient together in a single oral dosage composition such as a tablet or capsule, or each agent may be administered in separate dosage formulations.

Where separate dosage formulations are used, the compound of formula (I) and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention:

Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, and mitolactol; platinum-coordinated alkylating compounds include, but are not limited to, cisplatin, carboplatin, eptaplatin, lobaplatin, nedaplatin, oxaliplatin, and satraplatin;

Anti-metabolites include, but are not limited to, methotrexate, 6-mercaptopurine riboside, mercaptopurine, 5-fluorouracil alone or in combination with leucovorin, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosfite, disodium premetrexed, pentostatin, pelitrexol, raltitrexed, triapine, trimetrexate, vidarabine, vincristine, and vinorelbine;

Hormonal therapy agents include, but are not limited to, exemestane, Lupron, anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as fmasteride and epristeride, anti-estrogens such as tamoxifen citrate and fulvestrant, Trelstar, toremifene, raloxifene, lasofoxifene, letrozole, anti-androgens such as bicalutamide, flutamide, mifepristone, nilutamide, Casodex, and anti-progesterones and combinations thereof;

Plant-derived anti-tumor substances include, e.g., those selected from mitotic inhibitors, for example epothilones such as sagopilone, ixabepilone and epothilone B, vinblastine, vinflunine, docetaxel, and paclitaxel;

Cytotoxic topoisomerase inhibiting agents include, but are not limited to, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof;

Immunologicals include interferons such as interferon alpha, interferon alpha-2a, interferon alpha-2b, interferon beta, interferon gamma-1a and interferon gamma-n1, and other immune enhancing agents such as L19-IL2 and other IL2 derivatives, filgrastim, lentinan, sizofilan, TheraCys, ubenimex, aldesleukin, alemtuzumab, BAM-002, dacarbazine, daclizumab, denileukin, gemtuzumab, ozogamicin, ibritumomab, imiquimod, lenograstim, lentinan, melanoma vaccine (Corixa), molgramostim, sargramostim, tasonermin, tecleukin, thymalasin, tositumomab, Vimlizin, epratuzumab, mitumomab, oregovomab, pemtumomab, and Provenge;

Biological response modifiers are agents that modify defense mechanisms of living organisms or biological responses such as survival, growth or differentiation of tissue cells to direct them to have anti-tumor activity; such agents include, e.g., krestin, lentinan, sizofuran, picibanil, ProMune, and ubenimex;

Anti-angiogenic compounds include, but are not limited to, acitretin, aflibercept, angiostatin, aplidine, asentar, axitinib, bevacizumab, brivanib alaninat, cilengtide, combretastatin, endostatin, fenretinide, halofuginone, pazopanib, ranibizumab, rebimastat, recentin, regorafenib, removab, revlimid, sorafenib, squalamine, sunitinib, telatinib, thalidomide, ukrain, vatalanib, and vitaxin;

Antibodies include, but are not limited to, trastuzumab, cetuximab, bevacizumab, rituximab, ticilimumab, ipilimumab, lumiliximab, catumaxomab, atacicept, oregovomab, and alemtuzumab;

VEGF inhibitors such as, e.g., sorafenib, regorafenib, bevacizumab, sunitinib, recentin, axitinib, aflibercept, telatinib, brivanib alaninate, vatalanib, pazopanib, and ranibizumab;

EGFR (HER1) inhibitors such as, e.g., cetuximab, panitumumab, vectibix, gefitinib, erlotinib, and Zactima;

HER2 inhibitors such as, e.g., lapatinib, tratuzumab, and pertuzumab;

mTOR inhibitors such as, e.g., temsirolimus, sirolimus/ Rapamycin, and everolimus;

c-Met inhibitors;

PI3K and AKT inhibitors;

CDK inhibitors such as roscovitine and flavopiridol;

Spindle assembly checkpoints inhibitors and targeted antimitotic agents such as PLK inhibitors, Aurora inhibitors (e.g. Hesperadin), checkpoint kinase inhibitors, and KSP inhibitors;

HDAC inhibitors such as, e.g., panobinostat, vorinostat, MS275, belinostat, and LBH589;

HSP90 and HSP70 inhibitors;

Proteasome inhibitors such as bortezomib and carfilzomib;

Serine/threonine kinase inhibitors including MEK inhibitors and Raf inhibitors such as sorafenib;

Farnesyl transferase inhibitors such as, e.g., tipifarnib;

Tyrosine kinase inhibitors including, e.g., dasatinib, nilotibib, regorafenib, bosutinib, sorafenib, bevacizumab, sunitinib, cediranib, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab, and c-Kit inhibitors;

Vitamin D receptor agonists;

Bcl-2 protein inhibitors such as obatoclax, oblimersen sodium, and gossypol;

Cluster of differentiation 20 receptor antagonists such as, e.g., rituximab;

Ribonucleotide reductase inhibitors such as, e.g., gemcitabine;

Tumor necrosis apoptosis inducing ligand receptor 1 agonists such as, e.g., mapatumumab;

5-Hydroxytryptamine receptor antagonists such as, e.g., rEV598, xaliprode, palonosetron hydrochloride, granisetron, Zindol, and AB-1001;

Integrin inhibitors including alpha5-beta1 integrin inhibitors such as, e.g., E7820, JSM 6425, volociximab, and endostatin;

Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide;

Aromatase inhibitors such as, e.g., anastrozole, letrozole, testolactone, exemestane, aminoglutethimide, and formestane;

Matrix metalloproteinase inhibitors;

Other anti-cancer agents including, e.g., alitretinoin, ampligen, atrasentan bexarotene, bortezomib, bosentan, calcitriol, exisulind, fotemustine, ibandronic acid, miltefosine, mitoxantrone, l-asparaginase, procarbazine, dacarbazine, hydroxycarbamide, pegaspargase, pentostatin, tazaroten, velcade, gallium nitrate, canfosfamide, darinaparsin, and tretinoin.

In a preferred embodiment, the compounds of the present invention may be used in combination with chemotherapy (i.e. cytotoxic agents), anti-hormones and/or targeted therapies such as other kinase inhibitors (for example, EGFR inhibitors), mTOR inhibitors and angiogenesis inhibitors.

The compounds of the present invention may also be employed in cancer treatment in conjunction with radiation therapy and/or surgical intervention.

Furthermore, the compounds of formula (I) may be utilized, as such or in compositions, in research and diagnostics, or as analytical reference standards, and the like, which are well known in the art.

Pharmaceutical Compositions and Methods of Treatment

In another aspect, the invention provides a pharmaceutical composition comprising a compound of formula (I) as defined above, together with a pharmaceutically acceptable carrier.

In still another aspect, the invention provides a process for preparing a pharmaceutical composition. The process includes the step of comprising combining at least one compound of formula (I) as defined above with at least one pharmaceutically acceptable carrier, and bringing the resulting combination into a suitable administration form.

The active component of formula (I) can act systemically and/or locally. For this purpose, it can be applied in a suitable manner, for example orally, parenterally, pulmonally, nasally, sublingually, lingually, buccally, rectally, transdermally, conjunctivally, otically, or as an implant or stent.

For these application routes, the active component of formula (I) can be administered in suitable application forms.

Useful oral application forms include application forms which release the active component rapidly and/or in modified form, such as, for example, tablets (non-coated and coated tablets, for example with an enteric coating), capsules, sugar-coated tablets, granules, pellets, powders, emulsions, suspensions, solutions and aerosols.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders.

Forms suitable for other application routes include, for example, inhalatory pharmaceutical forms (including powder inhalers, nebulizers), nasal drops, solutions or sprays, tablets or capsules to be administered lingually, sublingually or buccally, suppositories, ear and eye preparations, vaginal capsules, aqueous suspensions (lotions, shake mixtures), lipophilic suspensions, ointments, creams, milk, pastes, dusting powders, implants or stents.

In a preferred embodiment, the pharmaceutical composition comprising a compound of formula (I) as defined above is provided in a form suitable for oral administration. In another preferred embodiment, the pharmaceutical composition comprising a compound of formula (I) as defined above is provided in a form suitable for intravenous administration.

The active component of formula (I) can be converted into the recited application forms in a manner known per se. This is carried out using inert non-toxic, pharmaceutically suitable excipients. These include, inter alfa, carriers (for example microcrystalline cellulose), solvents (for example liquid polyethylene glycols), emulsifiers (for example sodium dodecyl sulphate), dispersing agents (for example polyvinylpyrrolidone), synthetic and natural biopolymers (for example albumin), stabilizers (for example antioxidants such as ascorbic acid), colorants (for example inorganic pigments such as iron oxides) or taste and/or odor corrigents.

In another embodiment, the invention provides a method of treating a cell proliferative disorder in a patient in need of such treatment, comprising administering to the patient an effective amount of a compound of formula (I) as defined above. In certain embodiments, the cell proliferative disorder is cancer.

In still another aspect, the invention provides use of a compound of formula (I) as defined above for manufacturing a pharmaceutical composition for the treatment or prevention of a cell proliferative disorder. In certain embodiments, the cell proliferative disorder is cancer.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compounds of the invention, which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.01 to 100 mg/kg per day or 0.1 to 150 mg/kg per day.

In certain embodiments, the compound of the invention can be used in combination therapy with conventional cancer chemotherapeutics. Conventional treatment regimens for leukemia and for other tumors include radiation, drugs, or a combination of both.

Determination of a therapeutically effective anti-proliferative amount or a prophylactically effective anti-proliferative amount of the compounds of the invention can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective anti-proliferative amount or dose, and the prophylactically effective anti-proliferative amount or dose, a number of factors are considered by the attending clinician, including, but not limited to: the specific cell proliferative disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective anti-proliferative amount and a prophylactically effective anti-proliferative amount of a compound of the invention may be expected to vary from about 0.01 milligram per kilogram of body weight per day (mg/kg/day) to about 100 mg/kg/day.

A preferred dose of the compound of the invention for the present invention is the maximum that a patient can tolerate and not develop serious side effects. Illustratively, the compound of the present invention is administered at a dose of about 0.01 mg/kg to about 100 mg/kg of body weight, about 0.01 mg/kg to about 10 mg/kg of body weight or about 0.1 mg/kg to about 10 mg/kg of body weight. Ranges intermediate to the above-recited values are also intended to be part of the invention.

The percentages in the tests and examples which follows are, unless otherwise stated, by weight; parts are by weight. Solvent ratios, dilution ratios and concentrations reported for liquid/liquid solutions are each based on volume.

A. EXAMPLES

Abbreviations and Acronyms

Ac acetyl
aq. aqueous (solution)
br. s broad singlet (NMR)
conc. concentrated
d doublet (NMR)
DCI direct chemical ionization (MS)
dd doublet of doublets (NMR)
DMF N,N-dimethylformamide
DMSO dimethylsulfoxide
DMSO-$d_6$ dimethylsulfoxide-$d_6$
ee enantiomeric excess
EI electron impact ionization (MS)
equiv. equivalent(s)
ESI electro-spray ionization (MS)
Et ethyl
EtOAc ethyl acetate
GC-MS gas chromatography-coupled mass spectrometry
h hour(s)
$^1$H-NMR proton nuclear magnetic resonance spectrometry
HOAc acetic acid HPLC high performance/high pressure liquid chromatography
LC-MS liquid chromatography-coupled mass spectrometry
m multiplet (NMR)
Me methyl
MeOH methanol
min minute(s)
MS mass spectrometry
m/z mass-to-charge ratio
of th. of theory (chemical yield)
Ph phenyl
q quartet (NMR)
$R_f$ TLC retention factor
RP reverse phase (HPLC)
rt room temperature
$R_t$ retention time (HPLC)
singlet (NMR)
tBu tert-butyl
tBuO tert-butoxy
TFA trifluoroacetic acid
THF tetrahydrofuran
TLC thin layer chromatography
t triplet (NMR)
v/v volume-to-volume ratio
w/v weight-to-volume ratio
w/w weight-to-weight ratio
LC-MS and GC-MS Methods:
Method 1 (LC-MS):
Instrument: Micromass ZQ with HPLC Waters Alliance 2795; column: Phenomenex Synergi 2.5μ MAX-RP 100A Mercury, 20 mm×4 mm; eluent A: 1 L water+0.5 mL 50% formic acid, eluent B: 1 L acetonitrile+0.5 mL 50% formic acid; gradient: 0.0 min 90% A→0.1 min 90% A→3.0 min 5% A→4.0 min 5% A→4.01 min 90% A; flow rate: 2 mL/min; oven: 50° C.; UV detection: 210 nm.
Method 2 (LC-MS):
Instrument: Micromass Quattro Premier with HPLC Waters HPLC Acquity; column: Thermo Hypersil GOLD 1.9μ, 50 mm×1 mm; eluent A: 1 L water+0.5 mL 50% formic acid, eluent B: 1 L acetonitrile+0.5 mL 50% formic acid; gradient: 0.0 min 90% A→0.1 min 90% A→1.5 min 10% A→2.2 min 10% A; oven: 50° C.; flow rate: 0.33 mL/min; UV detection: 210 nm.
Method 3 (GC-MS):
Instrument: Micromass GCT, $GC_{6890}$; column: Restek RTX-35, 15 m×200 μm×0.33 μm; constant flow with helium: 0.88 mL/min; oven: 70° C.; inlet: 250° C.; gradient: 70° C., 30° C./min→310° C. (keep for 3 min).
Method 4 (LC-MS):
Instrument: Waters Acquity SQD HPLC System; column: Waters Acquity HPLC HSS T3 1.8μ, 50 mm×1 mm; eluent A: 1 L water+0.25 mL 99% formic acid, eluent B: 1 L acetonitrile+0.25 mL 99% formic acid; gradient: 0.0 min 90% A→1.2 min 5% A→2.0 min 5% A; oven: 50° C.; flow rate: 0.40 mL/min; UV detection: 210-400 nm.
Method 5 (LC-MS):
Instrument: Micromass Quattro Micro with HPLC Agilent 1100 Series; column: Thermo Hypersil GOLD 3μ, 20 mm×4 mm; eluent A: 1 L water+0.5 mL 50% formic acid, eluent B: 1 L acetonitrile+0.5 mL 50% formic acid; gradient: 0.0 min 100% A→3.0 min 10% A→4.0 min 10% A→4.01 min 100% A (flow rate 2.5 mL/min)→5.00 min 100% A; oven: 50° C.; flow rate: 2 mL/min; UV detection: 210 nm.
Method 6 (LC-MS):
Instrument: Micromass ZQ with HPLC HP 1100 Series; UV DAD; column: Phenomenex Gemini 3μ, 30 mm×3.00 mm; eluent A: 1 L water+0.5 mL 50% formic acid, eluent B: 1 L acetonitrile+0.5 mL 50% formic acid; gradient: 0.0 min 90% A→2.5 min 30% A→3.0 min 5% A→4.5 min 5% A; flow rate: 0.0 min 1 mL/min→2.5 min/3.0 min/4.5 min 2 mL/min; oven: 50° C.; UV detection: 210 nm.

Starting Materials and Intermediates

Example 1A

3-Methyl-1H-indazole-5-carbaldehyde

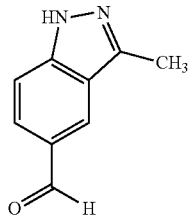

Tetrahydrofuran (600 ml) was cooled down to −78° C. under argon atmosphere. At this temperature, a 1.7 M solution of tert-butyllithium in n-pentane (200 ml) was added dropwise. After 15 minutes at −78° C., a solution of 22.4 g (106.1 mmol) 5-bromo-3-methyl-1H-indazole in THF (300 ml) was added dropwise at such a rate that the temperature of the solution did not exceed −70° C. The mixture was stirred for 30 minutes before N,N-dimethylformamide (24.5 ml) was added dropwise. After 20 min, the cooling bath was removed, and stirring was continued for 1 h before water (250 ml) was added carefully. The mixture was extracted several times with ethyl acetate (500 ml). The combined organic layers were washed with saturated aqueous sodium chloride solution, dried over sodium sulfate, and concentrated under reduced pressure to yield 18.5 g of crude 3-methyl-1H-indazole-5-carbaldehyde, which was used in the next step without further purification.

$^1$H-NMR (DMSO-$d_6$): δ=13.13 (br. s, 1H), 10.01 (s, 1H), 8.40 (s, 1H), 7.81 (d, 1H), 7.58 (d, 1H), 2.56 (s, 3H) ppm.

Example 2A (2E)-2-[(3-Methyl-1H-indazol-5-yl)methylidene]-3-oxobutanenitrile

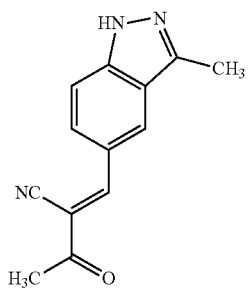 [SMILES: CC(=O)/C(C#N)=C/c1ccc2[nH]nc(C)c2c1]

A mixture of 5.0 g (31.2 mmol) 3-methyl-1H-indazole-5-carbaldehyde (Example 1A), 3.61 g (34.3 mmol) sodium (1Z)-1-cyanoprop-1-en-2-olate, 2.23 g (39 mmol) acetic acid and 0.31 ml (3.12 mmol) piperidine in dry dichloromethane (250 ml) containing 4 Å molecular sieve was stirred under reflux for 12 h. Upon cooling, a precipitate was formed which was collected by filtration and washed with saturated aqueous sodium bicarbonate solution and water. The solid was dissolved in ethanol, and the molecular sieve was filtered off. The filtrate was concentrated under reduced pressure, and the residue was treated with ethyl acetate and saturated aqueous sodium carbonate solution. The organic layer was washed with water, dried, and concentrated under reduced pressure to afford the title compound (3.5 g, 50% of th.) as a pale yellow solid which was used in the next step without further purification.

LC-MS (method 1): $R_t$=1.32 min; MS (ESIpos): m/z=226 (M+H)$^+$ $^1$H-NMR (400 MHz, DMSO-d$_6$): δ=13.18 (br. s, 1H), 8.52 (s, 1H), 8.49 (s, 1H), 8.19 (d, 1H), 7.69 (d, 1H), 2.55 (br. m, 6H) ppm.

Example 3A 1-(5-Bromo-2-fluorophenyl)-1-propanol

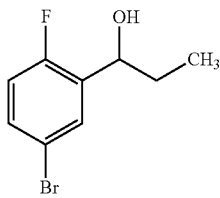

To a solution of 15 g (73.9 mmol) 5-bromo-2-fluorobenzaldehyde in diethyl ether (100 ml) at 0° C. were slowly added 27.1 ml (81.3 mmol) of ethyl magnesium bromide (3 M solution in diethyl ether). After stirring at 0° C. for 3 h, water (20 ml) was carefully added upon which a white precipitate formed. The solid was filtered off and washed with tert-butylmethyl ether. The combined filtrates were washed with brine, dried over sodium sulfate and concentrated under reduced pressure. The crude title compound thus obtained (16.1 g, 93% of th.) was used in the next step without further purification.

GC-MS (method 3): $R_t$=4.54 min; MS (EIpos): m/z=232 (M)$^+$.

Example 4A 1-(5-Bromo-2-fluorophenyl)-1-propanone

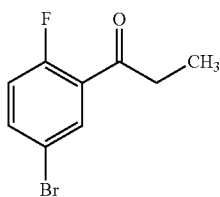

A mixture of 10 g (42.9 mmol) 1-(5-bromo-2-fluorophenyl)-1-propanol (Example 3A), 8.75 g (85.8 mmol) neutral aluminium oxide and 18.5 g (85.8 mmol) pyridinium chlorochromate in dichloromethane (100 ml) was stirred at room temperature for 4 h. The mixture was then filtered through silica gel (200 g, 0.06-0.2 mm) which was thoroughly washed with dichloromethane (1000 ml). The combined filtrates were washed with brine, dried over sodium sulfate and concentrated under reduced pressure. The crude title compound thus obtained (8.6 g, 87% of th.) was used in the next step without further purification.

GC-MS (method 3): $R_t$=4.30 min; MS (EIpos): m/z=230 (M)$^+$.

Example 5A

5-Bromo-3-ethyl-1H-indazole

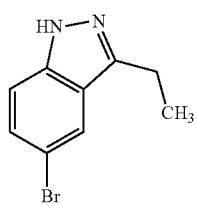

A solution of 7.50 g (32.5 mmol) 1-(5-bromo-2-fluorophenyl)-1-propanone (Example 4A) in 1-methyl-2-pyrrolidone (NMP; 100 ml) was treated with 3.25 g (3.16 ml, 64.9 mmol) hydrazine hydrate and stirred at reflux temperature for 16 h. Upon cooling, the mixture was poured into a mixture of ice and water. The precipitate was collected by filtration and washed thoroughly with water to yield 4.56 g (62% of th.) of the title compound as a beige-coloured solid.

LC-MS (method 4): $R_t$=1.00 min; MS (ESIpos): m/z=225 (M+H)$^+$.

Example 6A

3-Ethyl-1H-indazole-5-carbaldehyde

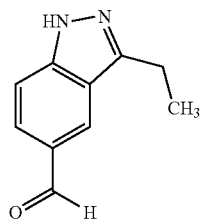

A solution of 6.90 g (30.7 mmol) 5-bromo-3-ethyl-1H-indazole (Example 5A) in THF (300 ml) was cooled to −78° C. At this temperature, a 1.7 M solution of tert-butyllithium in n-pentane (63.1 ml, 107 mmol) was slowly added. The mixture was stirred at −78° C. for 30 minutes before N,N-dimethylformamide (80.0 ml) was slowly added. The cooling bath was removed, and stirring was continued until room temperature was reached. Then, water (250 ml) was added carefully. The mixture was extracted several times with ethyl acetate (500 ml). The combined organic layers were washed with saturated aqueous sodium chloride solution, dried over sodium sulfate, and concentrated under reduced pressure to yield 4.5 g (84% of th.) of the crude title compound which was used in the next step without further purification.

LC-MS (method 4): $R_t$=0.73 min; MS (ESIpos): m/z=175 (M+H)$^+$.

Example 7A (2E)-2-[(3-Ethyl-1H-indazol-5-yl)methylidene]-3-oxobutanenitrile

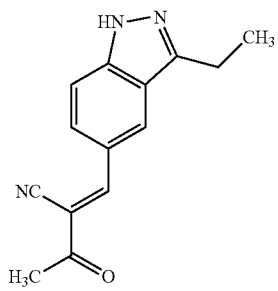 [SMILES: CCc1n[nH]c2ccc(/C=C(\C#N)C(C)=O)cc12]

A mixture of 0.50 g (2.87 mmol) 3-ethyl-1H-indazole-5-carbaldehyde (Example 6A), 0.33 g (3.16 mmol) sodium (1Z)-1-cyanoprop-1-en-2-olate, 0.21 ml (3.6 mmol) acetic acid and 0.028 ml (0.29 mmol) piperidine in dry dichloromethane (25 ml) containing 4 Å molecular sieve was stirred under reflux for 16 h. Upon cooling, a precipitate was formed which was collected by filtration and washed with saturated aqueous sodium bicarbonate solution and water. The solid was dissolved in ethanol, and the molecular sieve was filtered off. The filtrate was concentrated under reduced pressure, and the residue was treated with ethyl acetate and saturated aqueous sodium carbonate solution. The organic layer was washed with water, dried, and concentrated under reduced pressure to afford the title compound (0.60 g, 88% of th.) as a pale yellow solid which was used in subsequent steps without further purification.

LC-MS (method 1): $R_t$=1.50 min; MS (ESIpos): m/z=240 (M+H)$^+$ $^1$H-NMR (400 MHz, DMSO-d$_6$): δ=13.17 (br. s, 1H), 8.59 (s, 1H), 8.51 (s, 1H), 8.17 (d, 1H), 7.67 (d, 1H), 2.97 (q, 2H), 2.55 (br. m, 3H), 1.36 (t, 3H) ppm.

Example 8A (2E)-2-(1H-Indazol-5-ylmethylidene)-3-oxobutanenitrile

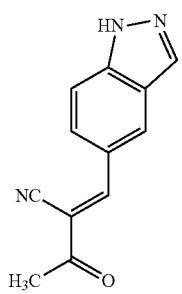 [SMILES: CC(=O)/C(C#N)=C/c1ccc2[nH]ncc2c1]

10 g (68.4 mmol) 1H-indazole-5-carbaldehyde [preparation described in US 2005/0227968-A1 (Intermediate 1)], 7.91 g (75.2 mmol) sodium (1Z)-1-cyanoprop-1-en-2-olate, 4.89 ml (85.5 mmol) acetic acid and 0.68 ml (6.84 mmol) piperidine in dry dichloromethane (500 ml) were stirred at reflux temperature for 7 h using an inverse water separator. Upon cooling, a precipitate was formed which was collected by filtration and washed with dichloromethane. The solid was dried in vacuo to afford the crude title compound (19 g, 75% purity by LC-MS, 96% of th.) which was used in subsequent steps without further purification.

LC-MS (method 2): $R_t$=0.82 min; MS (ESIpos): m/z=212 (M+H)$^+$.

Example 9A

5-Methoxy-3,6-dihydro-2H-1,4-oxazine

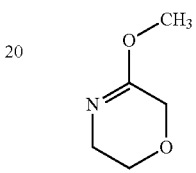

A solution of 1.2 g (11.9 mmol) morpholine-3-one in dichloromethane (70 ml) was cooled to 0° C. and treated with 25 g (238 mmol) dry sodium carbonate. After stirring for 10 min at 0° C., 6.14 g (41.5 mmol) trimethyloxonium tetrafluoroborate were added at 0° C. The mixture was allowed to warm to room temperature and stirred for 6 h. Water (100 ml) was added, and the organic layer was separated. The aqueous phase was extracted several times with dichloromethane, and the combined organic layers were washed with brine, dried over sodium sulfate and concentrated under reduced pressure. The crude product thus obtained was used in the next step without further purification.

GC-MS (method 3): $R_t$=3.36 min; MS (ESIpos): m/z=116 (M+H)$^+$.

Example 10A tert-Butyl (2E/Z)-cyano(morpholin-3-ylidene)ethanoate

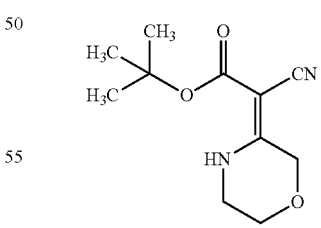

A mixture of 0.48 g (4.17 mmol) 5-methoxy-3,6-dihydro-2H-1,4-oxazine (Example 9A) and 0.61 g (4.34 mmol) tert-butyl cyanoacetate in THF (25 ml) was stirred under reflux for 12 h. The mixture was then cooled to room temperature and concentrated under reduced pressure. The residue was purified by flash chromatography (silica gel, eluent cyclohexane/ethyl acetate 3:1) to yield the title compound as a white solid (0.269 g, 27% of th.).

LC-MS (method 2): $R_t$=0.99 min; MS (ESIpos): m/z=225 (M+H)$^+$ $^1$H-NMR (400 MHz, DMSO-$d_6$): δ=10.02 (br. s, 1H), 4.47 (s, 2H), 3.84 (t, 2H), 3.37 (m, 2H), 1.44 (s, 9H) ppm.

Example 11A

3-Amino-3-(6-methoxypyridin-3-yl)prop-2-enenitrile

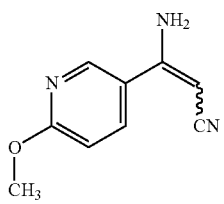

A solution of 0.258 ml (1.844 mmol) diisopropylamine in dry THF (1.5 ml) was cooled to −70° C. under inert gas atmosphere, and 1.152 ml (1.844 mmol) n-butyllithium (1.6 M solution in hexanes) were added dropwise. Then, a solution of 85.6 μl (1.627 mmol) acetonitrile in dry THF (1.5 ml) was slowly added over 10 min. The resulting solution was stirred for further 30 min at −70° C. before a solution of 150 mg (1.085 mmol) 2-methoxypyridine-5-carbonitrile in dry THF (1.5 ml) was added. The mixture was allowed to warm to room temperature and stirred for 1 h before water (2 ml) was added slowly. The mixture was extracted several times with dichloromethane (50 ml). The combined organic layers were dried over sodium sulfate and concentrated under reduced pressure to yield 188 mg (99% of th.) of the crude title compound which was used in the next step without further purification.

GC-MS (method 3): $R_t$=6.45 min; MS (EIpos): m/z=175 (M)$^+$.

Example 12A

5-Methoxy-3-oxopentanenitrile

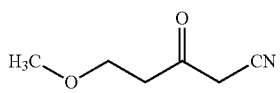

A flame-dried flask was charged with 5 ml (8.0 mmol) n-butyllithium (1.6 M solution in hexanes) in dry THF (25 ml) under inert gas atmosphere and cooled to −78° C. Next, 0.368 ml (7 mmol) acetonitrile were slowly added, and the resulting mixture was stirred for 1 h at −70° C. Then, 0.585 ml (5.0 mmol) methyl 3-methoxypropanoate were slowly added maintaining the temperature below −66° C. The reaction mixture was stirred for 2 h at −45° C. and then quenched by addition of hydrochloric acid (2 M, 16 ml) keeping the temperature below −35° C. The resulting clear solution was allowed to warm to room temperature and then concentrated under reduced pressure, and the residue was dried under high vacuum. The crude product thus obtained (1.51 g) was used in the next step without further purification.

GC-MS (method 3): $R_t$=3.18 min; MS (EIpos): m/z=127 (M)$^+$.

Example 13A

3-Bromo-1H-indazole-5-carbaldehyde

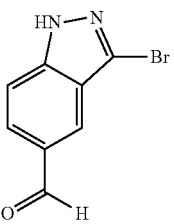 [SMILES: O=Cc1ccc2[nH]nc(Br)c2c1]

To a solution of 20 g (137 mmol) 1H-indazole-5-carbaldehyde in acetonitrile (580 ml), 28 g (157 mmol) 1-bromopyrrolidine-2,5-dione were added over 20 min at room temperature. The resulting suspension was stirred under reflux for 30 min, then cooled to room temperature and concentrated under reduced pressure. The residue was dissolved in ethyl acetate (1500 ml), and the solution was washed with water and with brine, dried over sodium sulfate, filtered and concentrated under reduced pressure. The crude product was triturated with ethyl acetate. After filtration, the precipitate was dried under vacuum to yield the title compound as a white solid (30.9 g, 75% of th.).

LC-MS (method 4): $R_t$=0.77 min; MS (ESIpos): m/z=225 (M+H)$^+$ $^1$H-NMR (400 MHz, DMSO-$d_6$): δ=15.01 (br. s, 1H), 10.09 (s, 1H), 8.29 (s, 1H), 7.91 (d, 1H), 7.73 (d, 1H) ppm.

Example 14A

3-Amino-3-(4-chloro-3-fluorophenyl)prop-2-enenitrile

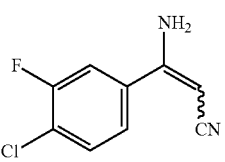 [SMILES: N#CC=C(N)c1ccc(Cl)c(F)c1]

The title compound was prepared following the procedure described for Example 11A using 4-chloro-3-fluorobenzonitrile (300 mg, 1.85 mmol) to yield 358 mg (98% of th.) of the crude product which was used in the next step without further purification.

GC-MS (method 3): $R_t$=6.30 min; MS (EIpos): m/z=196 (M)$^+$.

Example 15A

3-Amino-3-(3,5-difluorophenyl)prop-2-enenitrile

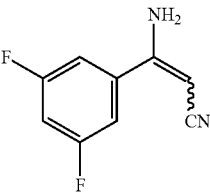 [SMILES: N#CC=C(N)c1cc(F)cc(F)c1]

The title compound was prepared following the procedure described for Example 11A using 3,5-difluorobenzonitrile (500 mg, 3.59 mmol) to yield 640 mg (99% of th.) of the crude product which was used in the next step without further purification.

GC-MS (method 3): $R_t$=5.13 min; MS (EIpos): m/z=180 (M)⁺.

Example 16A

3-Amino-3-(2,4-difluorophenyl)prop-2-enenitrile

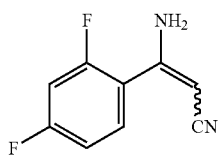

The title compound was prepared following the procedure described for Example 11A using 2,4-difluorobenzonitrile (300 mg, 2.1 mmol) to yield 288 mg (76% of th.) of the crude product which was used in the next step without further purification.

GC-MS (method 3): $R_t$=5.13 min; MS (EIpos): m/z=180 (M)⁺.

Example 17A

6-Fluoro-3-methyl-1H-indazole-5-carbaldehyde

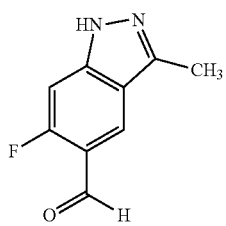

A solution of 30 g (131 mmol) 5-bromo-6-fluoro-3-methyl-1H-indazole [preparation described in WO 2005/085227-A1, Example 104c); also commercially available, CAS Reg.-No. 864773-66-0] in THF (525 ml) was cooled to −45° C. A solution of methylmagnesium chloride in THF (3 M; 50.2 ml, 151 mmol) was added dropwise at −45° C., and the resulting solution was stirred for 40 min at this temperature. Using a dosing pump, 253 ml (354 mmol) of 2-butyllithium solution (1.4 M in cyclohexane) were added so that the temperature did not exceed −40° C. The resulting mixture was stirred for 30 min at −40° C., and then 30.2 ml (393 mmol) N,N-dimethylformamide were added dropwise keeping the temperature at −40° C. The resulting mixture was stirred for 30 min at −40° C., then allowed to warm up to room temperature, and slowly poured into a volume of 2.8 L of 2 N hydrochloric acid cooled to 5° C. (ice-water bath). The mixture was extracted several times with ethyl acetate. The combined organic layers were washed with brine, dried over sodium sulfate, filtered, and concentrated under reduced pressure. The residue was dissolved in dichloromethane and purified by chromatography on silica gel (eluent: pentane/ethyl acetate 6:4 v/v) to afford 19.6 g (78% of th.) of the title compound as a pale yellow solid.

MS (ESIpos): m/z=179 (M+H)⁺
¹H-NMR (400 MHz, DMSO-d₆): δ=13.14 (s, 1H), 10.17 (s, 1H), 8.33 (d, 1H), 7.37 (d, 1H), 2.54 (s, ³H) ppm.

Example 18A (2E)-2-[(6-Fluoro-3-methyl-1H-indazol-5-yl)methylidene]-3-oxobutanenitrile

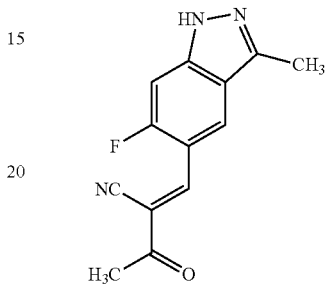

Following the procedure described for Example 2A, the title compound was prepared using 2.74 g (15.5 mmol) 6-fluoro-3-methyl-1H-indazole-5-carbaldehyde (Example 17A) and 2.6 g (24.8 mmol) sodium (1Z)-1-cyanoprop-1-en-2-olate to yield 1.6 g (42% of th.) of the crude product which was used in the next step without further purification.

LC-MS (method 4): $R_t$=0.83 min; MS (ESIpos): m/z=244 (M+H)⁺.

Example 19A

6-Fluoro-1H-indazole-5-carbaldehyde

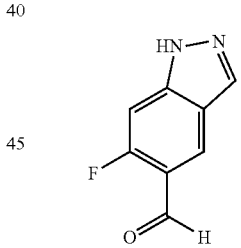

A slurry of 4.8 g (30 mmol) 6-fluoro-1H-indazole-5-carbonitrile [commercially available; preparation given in EP 1 510 516-A1 (production example 82)] in anhydrous toluene (150 ml) was cooled to −40° C. Under inert gas atmosphere, 48 ml (72 mmol) diisobutylaluminium hydride solution (1.5 M in toluene) were added over 30 min, and the resulting mixture was stirred at −40° C. for 3 h. Then, ethyl acetate (30 ml) was added, and the mixture was stirred for further 20 min at −40° C. followed by dropwise addition of aqueous tartaric acid (1 M, 30 ml). The mixture was allowed to warm to 0° C. and filtered at this temperature. The filtrate was extracted with ethyl acetate several times, and the combined organic phases were subsequently washed with saturated aqueous sodium hydrogencarbonate and with brine, dried over sodium sulfate, filtered and concentrated under reduced pressure. The crude product thus obtained (2.60 g, 53% of th.) was used in the next step without further purification.

LC-MS (method 4): $R_t$=0.59 min; MS (ESIpos): m/z=165 (M+H)$^+$.

Example 20A (2E)-2-[(6-Fluoro-1H-indazol-5-yl)methylidene]-3-oxobutanenitrile

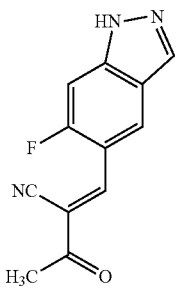 [SMILES: CC(=O)/C(C#N)=C/c1cc2cn[nH]c2cc1F]

The title compound was prepared from 3.7 g (80% purity, 18.0 mmol) 6-fluoro-1H-indazole-5-carbaldehyde (Example 19A) and 2.08 g (19.84 mmol) sodium (1Z)-1-cyanoprop-1-en-2-olate in analogy to the procedure described in Example 2A yielding 2.5 g (61% of th.) of product which was used in subsequent steps without further purification.

LC-MS (method 2): $R_t$=0.71 min; MS (ESIpos): m/z=230 (M+H)$^+$ $^1$H-NMR (400 MHz, DMSO-d$_6$): δ=13.90 (s, 1H), 8.59 (s, 1H), 8.46 (s, 1H), 8.23 (d, 1H), 7.80 (d, 1H), 2.5 (br. s, 31-1) ppm.

Example 21A

3-Amino-3-[4-(trifluoromethyl)phenyl]prop-2-enenitrile

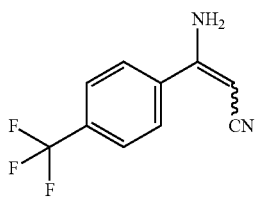 [SMILES: N#CC=C(N)c1ccc(C(F)(F)F)cc1]

The title compound was prepared following the procedure described for Example 11A using 4-(trifluoromethyl)benzonitrile (500 mg, 2.89 mmol) to yield 606 mg (99% of th.) of the crude product which was used in the next step without further purification.

LC-MS (method 5): $R_t$=2.08 min; MS (EIpos): m/z=213 (M+H)$^+$.

PREPARATION EXAMPLES

Example 1

2-Methyl-4-(3-methyl-1H-indazol-5-yl)-5-oxo-1,4,5,7-tetrahydrofuro[3,4-b]pyridine-3-carbonitrile

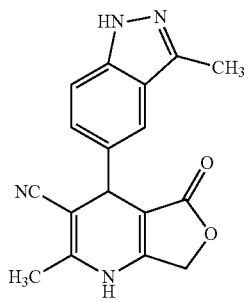

Method A:

A solution of 300 mg (1.332 mmol) (2E)-2-[(3-methyl-1H-indazol-5-yl)methylidene]-3-oxobutanenitrile (Example 2A), 136 mg (1.332 mmol) furan-2,4(3H,5H)-dione and 123 mg (1.598 mmol) ammonium acetate in acetic acid (6.3 ml) was stirred at 110° C. for 3 h. The reaction mixture was then concentrated under reduced pressure, and the residue was purified by flash chromatography (silica gel; dichloromethane/methanol gradient, final mixture 30:1 v/v) to give 59 mg (14% of th.) of the racemic title compound.

Method B:

A solution of 100 mg (0.624 mmol) 3-methyl-1H-indazole-5-carbaldehyde (Example 1A), 54 mg (0.624 mmol) 3-aminobut-2-enenitrile and 120 mg (0.624 mmol) ethyl 4-(acetoxy)-3-oxobutanoate [preparation: U.S. Pat. No. 4,720,572 (Example 1)] in 1-propanol (2 ml) was stirred at reflux temperature overnight. Then, concentrated hydrochloric acid (115 μl) and water (350 μl) were added, and stirring was continued at 100° C. for 1 h. After cooling, the mixture was directly purified by preparative RP-HPLC (acetonitrile/water+0.1% TFA gradient) to yield 103 mg (51% of th.) of the racemic title compound.

LC-MS (method 2): $R_t$=0.72 min; MS (ESIpos): m/z=307 (M+H)$^+$ $^1$H-NMR (400 MHz, DMSO-d$_6$): δ=12.62 (br. s, 1H), 10.69 (br. s, 1H), 7.50 (s, 1H), 7.42 (d, 1H), 7.23 (d, 1H), 4.89 (dd, 2H), 4.61 (s, 1H), 2.48 (s, 3H), 2.12 (s, 3H) ppm.

Example 2 and Example 3

2-Methyl-4-(3-methyl-1H-indazol-5-yl)-5-oxo-1,4,5,7-tetrahydrofuro[3,4-b]pyridine-3-carbonitrile (Enantiomer 1 and 2)

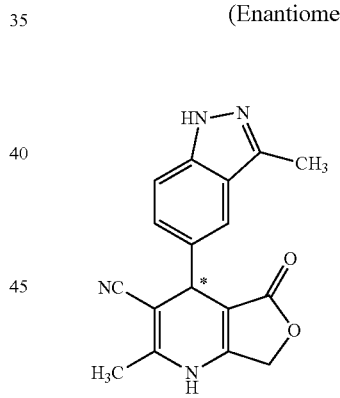

The racemic compound from Example 1 (125 mg) was separated into the enantiomers by HPLC chromatography on a chiral phase [column: Daicel Chiralpak AS-H, 5 μm, 250 mm×20 mm; eluent: iso-hexane/ethanol 65:35 v/v; flow rate: 15 ml/min; temperature: 35° C.; UV detection: 220 nm]:

Example 2

Enantiomer 1

Yield: 49 mg (chemical purity >99%, >99% ee)

$R_t$=5.66 min [column: Daicel Chiralpak AS-H, 5 μm, 250 mm×4.6 mm; Eluent: iso-hexane/ethanol 70:30+0.2% diethylamine; flow rate: 1 ml/min; temperature: 30° C.; UV detection: 235 nm].

Example 3

Enantiomer 2

Yield: 45 mg (chemical purity >95%, >99% ee)

$R_t$=10.10 min [column: Daicel Chiralpak AS-H, 5 μm, 250 mm×4.6 mm; Eluent: iso-hexane/ethanol 70:30+0.2% diethylamine; flow rate: 1 ml/min; temperature: 30° C.; UV detection: 235 nm].

Example 4

4-(3-Ethyl-1H-indazol-5-yl)-2-methyl-5-oxo-1,4,5,7-tetrahydrofuro[3,4-b]pyridine-3-carbonitrile

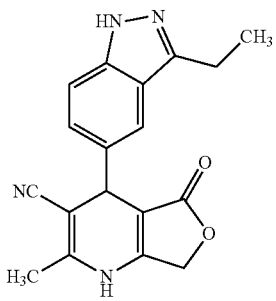 [SMILES: CCc1n[nH]c2ccc(C3C(C#N)=C(C)NC4=C3C(=O)OC4)cc12]

The title compound was prepared from 600 mg (2.508 mmol) (2E)-2-[(3-ethyl-1H-indazol-5-yl)-methylidene]-3-oxobutanenitrile (Example 7A), 256 mg (2.508 mmol) furan-2,4(3H,5H)-dione and 232 mg (3.010 mmol) ammonium acetate in analogy to the procedure described in Example 1 yielding 98 mg (12% of th.) of the racemic compound after purification by flash chromatography (silica gel; dichloromethane/methanol gradient, final mixture 30:1 v/v).

LC-MS (method 2): $R_t$=0.81 min; MS (ESIpos): m/z=321 (M+H)$^+$ $^1$H-NMR (400 MHz, DMSO-d$_6$): δ=12.61 (br. s, 1H), 10.66 (br. s, 1H), 7.54 (s, 1H), 7.42 (d, 1H), 7.22 (d, 1H), 4.89 (dd, 2H), 4.62 (s, 1H), 2.90 (q, 2H), 2.12 (s, 3H), 1.31 (t, 3H) ppm.

Example 5 and Example 6

4-(3-Ethyl-1H-indazol-5-yl)-2-methyl-5-oxo-1,4,5,7-tetrahydrofuro[3,4-b]pyridine-3-carbonitrile (Enantiomer 1 and 2)

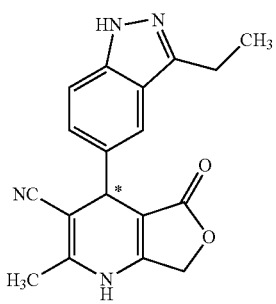 [SMILES: CCc1n[nH]c2ccc(C3C(C#N)=C(C)NC4=C3C(=O)OC4)cc12]

The racemic compound from Example 4 (90 mg) was separated into the enantiomers by HPLC chromatography on a chiral phase [column: Daicel Chiralpak AS-H, 5 μm, 250 mm×20 mm; eluent: iso-hexane/ethanol 50:50 v/v; flow rate: 15 ml/min; temperature: 30° C.; UV detection: 220 nm]:

Example 5

Enantiomer 1

Yield: 25 mg (chemical purity >98.5%, >99% ee)

$R_t$=3.90 min [column: Daicel Chiralpak AS-H, 5 μm, 250 mm×4.6 mm; eluent: iso-hexane/ethanol 50:50; flow rate: 1 ml/min; temperature: 30° C.; UV detection: 220 nm].

Example 6

Enantiomer 2

Yield: 25 mg (chemical purity >94%, >98.8% ee)

$R_t$=6.24 min [column: Daicel Chiralpak AS-H, 5 μm 250 mm×4.6 mm; eluent: iso-hexane/ethanol 50:50; flow rate: 1 ml/min; temperature: 30° C.; UV detection: 220 nm].

Example 7

2,8,8-Trimethyl-4-(3-methyl-1H-indazol-5-yl)-5-oxo-1,5,7,8-tetrahydro-4H-pyrano[4,3-b]pyridine-3-carbonitrile

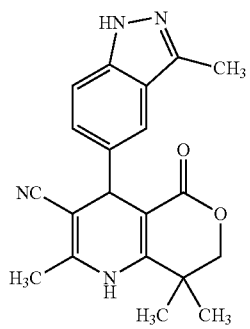 [SMILES: CC1=C(C#N)C(c2ccc3[nH]nc(C)c3c2)C2=C(N1)C(C)(C)COC2=O]

The title compound was prepared from 200 mg (0.888 mmol) (2E)-2-[(3-methyl-1H-indazol-5-yl)-methylidene]-3-oxobutanenitrile (Example 2A), 126 mg (0.888 mmol) 5,5-dimethyldihydro-2H-pyran-2,4(3H)-dione [preparation: US 2006/0014826-A1 (Intermediate 6)] and 102 mg (1.332 mmol) ammonium acetate in analogy to the procedure described in Example 1 yielding 51 mg (16% of th.) after purification by preparative RP-HPLC (acetonitrile/water+0.1% TFA gradient) followed by flash chromatography (silica gel; ethyl acetate/cyclohexane gradient, final mixture 5:1 v/v).

LC-MS (method 4): $R_t$=0.76 min; MS (ESIpos): m/z=349 (M+H)$^+$

¹H-NMR (400 MHz, DMSO-d₆): δ=12.60 (s, 1H), 8.94 (s, 1H), 7.43-7.38 (m, 2H), 7.29 (d, 1H), 4.56 (s, 1H), 3.90 (dd, 2H), 2.48 (s, 3H), 2.14 (s, 3H), 1.25 (s, 6H) ppm.

Example 8

2-Methyl-4-(3-methyl-1H-indazol-5-yl)-5-oxo-4,5,6,7-tetrahydro-1H-pyrrolo[3,4-b]pyridine-3-carbonitrile

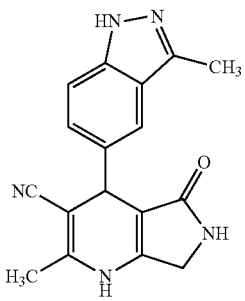

A solution of 200 mg (0.888 mmol) (2E)-2-[(3-methyl-1H-indazol-5-yl)methylidene]-3-oxobutanenitrile (Example 2A), 353 mg (0.888 mmol, approx. 50% purity) tert-butyl 4-hydroxy-2-oxo-2,5-dihydro-1H-pyrrole-1-carboxylate [W.-R. Li et al., J. Org. Chem. 2002, 67, 4702-4706] and 102 mg (1.332 mmol) ammonium acetate in acetic acid (4 ml) was stirred at 100° C. for 45 min. The reaction mixture was concentrated under reduced pressure, and the residue was purified first by flash chromatography (silica gel; dichloromethane/methanol gradient, final mixture 10:1 v/v) and then by preparative RP-HPLC (acetonitrile/water+0.1% TFA gradient) to give 31 mg (11% of th.) of the title compound.

LC-MS (method 2): $R_t$=0.63 min; MS (ESIpos): m/z=306 (M+H)⁺

¹H-NMR (400 MHz, DMSO-d₆): δ=12.58 (br. s, 1H), 9.72 (s, 1H), 7.44 (s, 1H), 7.40 (d, 1H), 7.21 (d, 1H), 4.53 (s, 1H), 3.91 (dd, 2H), 2.48 (s, 3H), 2.10 (s, 3H) ppm.

Example 9

2,7,7-Trimethyl-4-(3-methyl-1H-indazol-5-yl)-5-oxo-4,5,6,7-tetrahydro-1H-pyrrolo[3,4-b]pyridine-3-carbonitrile

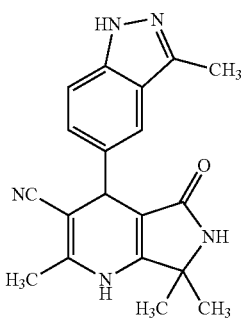

A solution of 200 mg (0.888 mmol) (2E)-2-[(3-methyl-1H-indazol-5-yl)methylidene]-3-oxobutanenitrile (Example 2A), 226 mg (0.888 mmol, approx. 50% purity) 4-hydroxy-5,5-dimethyl-1,5-dihydro-2H-pyrrol-2-one [K. Matsuo et al., Chem. Pharm. Bull. 1984, 32, 3724-3729] and 102 mg (1.332 mmol) ammonium acetate in acetic acid (4 ml) was stirred at 100° C. for 15 min. The reaction mixture was concentrated under reduced pressure, and the residue was purified first by preparative RP-HPLC (acetonitrile/water+0.1% TFA gradient) and then by preparative TLC (eluent: dichloromethane/methanol 10:1) to give 33 mg (11% of th.) of the title compound.

LC-MS (method 4): $R_t$=0.65 min; MS (ESIpos): m/z=334 (M+H)⁺

¹H-NMR (400 MHz, DMSO-d₆): δ=12.58 (s, 1H), 9.58 (s, 1H), 7.61 (s, 1H), 7.41-7.38 (m, 2H), 7.18 (d, 1H), 4.49 (s, 1H), 2.48 (s, 3H), 2.12 (s, 3H), 1.35 (s, 3H), 1.33 (s, 3H) ppm.

Example 10

7-(1H-Indazol-5-yl)-5-methyl-2,3,4,7-tetrahydrothieno[3,2-b]pyridine-6-carbonitrile-1,1-dioxide

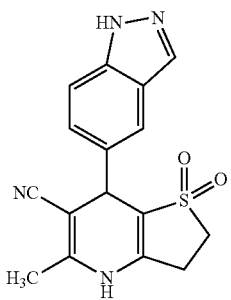 [SMILES: CC1=C(C#N)C(c2ccc3[nH]ncc3c2)C2=C(CCS2(=O)=O)N1]

127 mg (0.947 mmol) dihydrothiophen-3(2H)-one-1,1-dioxide, 266 mg (0.947 mmol) (2E)-2-(1H-indazol-5-ylmethylidene)-3-oxobutanenitrile (Example 8A) and 88 mg (1.136 mmol) ammonium acetate in acetic acid (5 ml) were heated to reflux overnight. After cooling, the mixture was evaporated to dryness, and the residue was purified by preparative RP-HPLC (acetonitrile/water gradient) to yield 16 mg (5% of th.) of the title compound.

LC-MS (method 5): $R_t$=1.31 min; MS (ESIpos): m/z=327 (M+H)⁺

¹H-NMR (400 MHz, DMSO-d₆): δ=9.75 (s, 1H), 8.05 (s, 1H), 7.59 (s, 1H), 7.49 (d, 1H), 7.26 (d, 1H), 4.73 (s, 1H), 3.37-3.26 (m, 2H), 3.01-2.93 (m, 1H), 2.84-2.77 (m, 1H), 2.07 (s, 3H) ppm.

Example 11

5-Methyl-7-(3-methyl-1H-indazol-5-yl)-2,3,4,7-tetrahydrothieno[3,2-b]pyridine-6-carbonitrile-1,1-dioxide

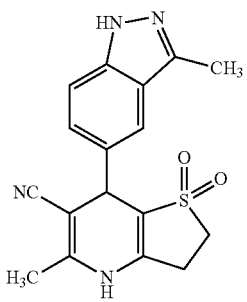 [SMILES: CC1=C(C#N)C(c2ccc3[nH]nc(C)c3c2)C2=C(CCS2(=O)=O)N1]

850 mg (6.336 mmol) dihydrothiophen-3(2H)-one-1,1-dioxide, 1.78 g (6.336 mmol) (2E)-2-[(3-methyl-1H-indazol-5-yl)methylidene]-3-oxobutanenitrile (Example 2A) and 586 mg (7.603 mmol) ammonium acetate in acetic acid (30 ml) were heated to reflux overnight. After cooling, the mixture was evaporated to dryness, and the residue was taken up in ethyl acetate and washed with water and brine. The organic layer was separated and dried over sodium sulfate. After filtration and evaporation to dryness, the remaining solid was purified by preparative RP-HPLC (acetonitrile/water gradient) to yield 89 mg (4% of th.) of the title compound.

LC-MS (method 5): $R_t$=1.36 min; MS (ESIpos): m/z=341 $(M+H)^+$ $^1$H-NMR (400 MHz, DMSO-$d_6$): δ=9.73 (s, 1H), 7.50 (s, 1H), 7.41 (d, 1H), 7.24 (d, 1H), 4.73 (s, 1H), 3.37-3.26 (m, 2H), 3.01-2.93 (m, 1H), 2.84-2.77 (m, 1H), 2.47 (s, 3H), 2.07 (s, 3H) ppm.

Example 12

2-Methyl-4-(3-methyl-1H-indazol-5-yl)-5-oxo-1,4,5,6,7,8-hexahydroquinoline-3-carbonitrile

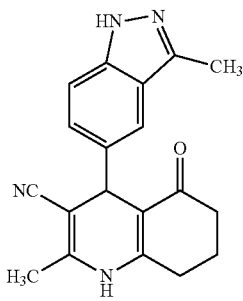 [SMILES: CC1=C(C#N)C(c2ccc3[nH]nc(C)c3c2)C2=C(CCCC2=O)N1]

273 mg (2.442 mmol) cyclohexane-1,3-dione, 500 mg (2.222 mmol) (2E)-2-[(3-methyl-1H-indazol-5-yl)methylidene]-3-oxobutanenitrile (Example 2A) and 205 mg (2.664 mmol) ammonium acetate in acetic acid (5 ml) were heated to 50° C. overnight. Then, additional ammonium acetate (102 mg, 1.332 mmol) was added, and the mixture was heated to reflux for 24 h. After cooling, the mixture was evaporated to dryness, and the residue was taken up in ethyl acetate and washed with water twice. The combined aqueous phases were extracted with ethyl acetate. The organic layers were combined and dried over sodium sulfate. After filtration and evaporation to dryness, the remaining solid was purified by preparative RP-HPLC (acetonitrile/water gradient) to yield 55 mg (8% of th.) of the title compound.

LC-MS (method 5): $R_t$=1.42 min; MS (ESIpos): m/z=319 $(M+H)^+$ $^1$H-NMR (400 MHz, DMSO-$d_6$): δ=12.52 (s, 1H), 9.48 (s, 1H), 7.38 (s, 1H), 7.36 (d, 1H), 7.17 (d, 1H), 4.54 (s, 1H), 2.51 (m, 2H), 2.45 (s, 3H), 2.27-2.12 (m, 2H), 2.07 (s, 3H), 1.94-1.89 (m, 1H), 1.85-1.74 (m, 1H) ppm.

Example 13

2-Methyl-4-(3-methyl-1H-indazol-5-yl)-5-oxo-4,5,6,7-tetrahydro-1H-cyclopenta[b]pyridine-3-carbonitrile

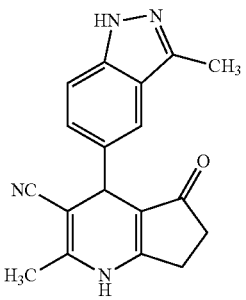

91 mg (0.936 mmol) cyclopentane-1,3-dione, 150 mg (0.936 mmol) 3-methyl-1H-indazole-5-carbaldehyde (Example 1A) and piperidine (0.1 ml) in ethanol (8 ml) were heated to reflux for 1.5 h and then left standing without stirring at room temperature overnight. The mixture was then evaporated to dryness, the remaining solid was dissolved in acetic acid (8 ml), and 77 mg (0.936 mmol) 3-aminobut-2-enenitrile were added. The solution was heated to reflux for 2 h. After cooling, the mixture was evaporated to dryness again, and the remaining solid was purified by preparative RP-HPLC (acetonitrile/water gradient) to yield 34 mg (12% of th.) of the title compound.

LC-MS (method 5): $R_t$=1.32 min; MS (ESIpos): m/z=305 $(M+H)^+$ $^1$H-NMR (400 MHz, DMSO-$d_6$): δ=12.55 (s, 1H), 10.06 (s, 1H), 7.43 (br. s, 1H), 7.37 (d, 1H), 7.17 (dd, 1H), 4.49 (s, 1H), 2.64-2.58 (m, 2H), 2.46 (s, 3H), 2.26-2.23 (m, 2H), 2.12 (s, 3H) ppm.

Example 14

4-(1H-Indazol-5-yl)-2-methyl-5-oxo-4,5,6,7-tetrahydro-1H-cyclopenta[b]pyridine-3-carbonitrile

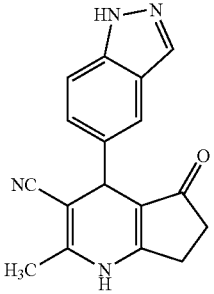

100 mg (1.026 mmol) cyclopentane-1,3-dione, 150 mg (1.026 mmol) 1H-indazole-5-carbaldehyde and piperidine (0.1 ml) in ethanol (8 ml) were heated to reflux for 4 h. The mixture was then evaporated to dryness, the remaining solid was dissolved in acetic acid (8 ml), and 84 mg (1.026 mmol)

3-aminobut-2-enenitrile were added. The solution was heated to reflux for 2 h. After cooling, the mixture was evaporated to dryness again, and the remaining solid was purified by preparative RP-HPLC (acetonitrile/water gradient) to yield 40 mg (13% of th.) of the title compound.

LC-MS (method 5): $R_t$=1.27 min; MS (ESIpos): m/z=291 (M+H)$^+$ $^1$H-NMR (400 MHz, DMSO-d$_6$): δ=12.99 (s, 1H), 10.08 (s, 1H), 8.02 (s, 1H), 7.52 (s, 1H), 7.46 (d, 1H), 7.22 (dd, 1H), 4.49 (s, 1H), 2.69-2.56 (m, 2H), 2.26-2.23 (m, 2H), 2.12 (s, 3H) ppm.

Example 15

8-(3-Methyl-1H-indazol-5-yl)-3,4,7,8-tetrahydro-1H, 5H-difuro[3,4-b:3',4'-e]pyridine-1,5-dione

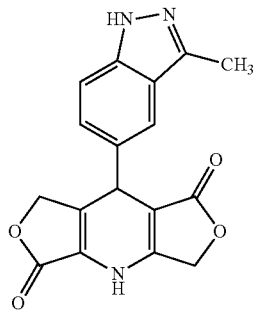 [SMILES: Cc1n[nH]c2ccc(C3C4=C(NC5=C3C(=O)OC5)C(=O)OC4)cc12]

A solution of 120 mg (0.75 mmol) 3-methyl-1H-indazole-5-carbaldehyde (Example 1A) and 75 mg (0.75 mmol) furan-2,4(3H,5H)-dione in 1-pentanol (1.5 ml) was stirred at reflux for 1 h. The mixture was then cooled to room temperature, water (1.5 ml) was added, and the mixture was concentrated under reduced pressure. The residue was dissolved in acetic acid (1.5 ml), and 111 mg (1.12 mmol) 3-aminofuran-2(5H)-one [U. Kraatz et al., Chem. Ber. 1971, 104, 2458-2466] were added. The resulting solution was stirred at 100° C. for 2 h, then cooled to room temperature and concentrated under reduced pressure. The residue was purified by preparative RP-HPLC (acetonitrile/water gradient) to give 68 mg (27% of th.) of the title compound.

LC-MS (method 4): $R_t$=0.60 min; MS (ESIpos): m/z=324 (M+H)$^+$ $^1$H-NMR (400 MHz, DMSO-d$_6$): δ=12.60 (s, 1H), 10.21 (s, 1H), 7.53 (s, 1H), 7.41 (d, 1H), 7.24 (d, 1H), 4.97-4.81 (m, 4H), 4.45-4.35 (m, 1H), 2.47 (s, 3H) ppm.

Example 16

4-(3-Methyl-1H-indazol-5-yl)-5-oxo-2-(trifluoromethyl)-1,4,5,7-tetrahydrofuro[3,4-b]pyridine-3-carbonitrile

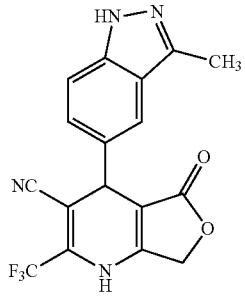 [SMILES: Cc1n[nH]c2ccc(C3C(C#N)=C(C(F)(F)F)NC4=C3C(=O)OC4)cc12]

100 mg (0.624 mmol) 3-methyl-1H-indazole-5-carbaldehyde (Example 1A) and 62.5 mg (0.624 mmol) furan-2,4(3H, 5H)-dione were heated up to reflux in 1-pentanol (3 ml) for 1 h. After addition of 425 mg (3.120 mmol) 3-amino-4,4,4-trifluorobut-2-enenitrile [A. W. Lutz, U.S. Pat. No. 3,635,977], the reaction mixture was stirred at 100° C. for further 4 h. Then, conc. hydrochloric acid (115 µl) and water (350 µl) were added, and the mixture was stirred at 100° C. for another 1 h. After cooling, the mixture was directly purified by RP-HPLC (acetonitrile/water+0.1% TFA gradient) to give 33 mg (14% of th.) of the title compound.

LC-MS (method 4): $R_t$=0.78 min; MS (ESIpos): m/z=361 (M+H)$^+$ $^1$H-NMR (400 MHz, DMSO-d$_6$): δ=12.70 (br. s, 1H), 11.04 (s, 1H), 7.60 (s, 1H), 7.29 (d, 1H), 4.95 (dd, 2H), 4.90 (s, 1H), 2.50 (s, 3H) ppm.

Example 17

1,2-Dimethyl-4-(3-methyl-1H-indazol-5-yl)-5-oxo-1, 4,5,7-tetrahydrofuro[3,4-b]pyridine-3-carbonitrile

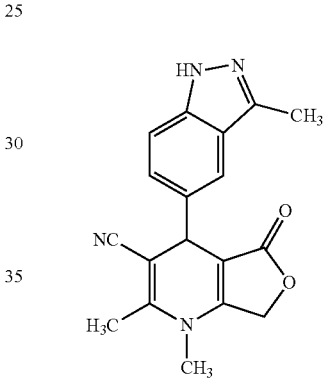

A solution of 100 mg (0.326 mmol) 2-methyl-4-(3-methyl-1H-indazol-5-yl)-5-oxo-1,4,5,7-tetrahydrofuro[3,4-b]pyridine-3-carbonitrile (Example 1) in DMF (2 ml) was cooled to 0° C. 128 mg (0.392 mmol) caesium carbonate were added at this temperature, and after 30 min 14 µl (0.229 mmol) methyl iodide were added dropwise. After stirring overnight at rt, additional methyl iodide (2 µl) was added, and stirring at rt was continued for further 3 h. Again, methyl iodide (6 µl) and a small amount of caesium carbonate were added, and the reaction mixture was stirred at rt overnight before water (1 ml) was added. The solution was directly purified first by preparative RP-HPLC (acetonitrile/water+0.1% TFA gradient) followed by preparative TLC (eluent: dichloromethane/ethanol 20:1) to give 11 mg (11% of th.) of the title compound.

LC-MS (method 2): $R_t$=0.75 min; MS (ESIpos): m/z=321 (M+H)$^+$ $^1$H-NMR (400 MHz, DMSO-d$_6$): δ=12.62 (br. s, 1H), 7.51 (s, 1H), 7.42 (d, 1H), 7.26 (d, 1H), 5.07 (dd, 2H), 4.61 (s, 1H), 3.18 (s, 3H), 2.48 (s, 3H), 2.28 (s, 3H) ppm.

Example 18

4-(3-Methyl-1H-indazol-5-yl)-3-oxo-1,3,4,6,8,9-hexahydrofuro[3',4':5,6]pyrido[2,1-c][1,4]oxazine-5-carbonitrile

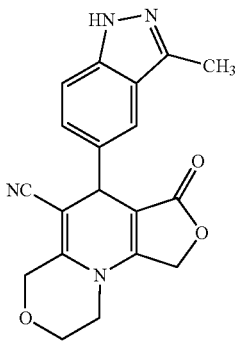

In flask A, 235 mg (1.469 mmol) 3-methyl-1H-indazole-5-carbaldehyde (Example 1A) and 150 mg (1.469 mmol) furan-2,4(3H,5H)-dione were heated up to reflux in 1-pentanol (3 ml) for 1 h and then cooled to room temperature. In a second flask B, a mixture of 494 mg (2.203 mmol) tert-butyl (2E/Z)-cyano(morpholin-3-ylidene)ethanoate (Example 10A) in 6 M hydrochloric acid (21 ml) was heated to 100° C. for 15 min. After cooling to room temperature, the solution in flask B was concentrated under reduced pressure, and the remaining solid was dissolved in acetic acid (4 ml). This solution was added to flask A, and the resulting mixture was stirred at 100° C. for 1.5 h. The mixture was then cooled to room temperature and concentrated under reduced pressure. The residue was purified by flash chromatography (silica gel; toluene/ethanol gradient, final mixture 10:1 v/v) to yield the title compound as a white solid (151 mg, 29% of th.).

LC-MS (method 4): $R_t$=0.70 min; MS (ESIpos): m/z=349 (M+H)$^+$ $^1$H-NMR (400 MHz, DMSO-d$_6$): δ=12.63 (br. s, 1H), 7.55 (s, 1H), 7.44 (d, 1H), 7.30 (d, 1H), 5.09 (s, 2H), 4.69 (s, 1H), 4.59 (m, 2H), 3.99 (m, 2H), 3.55 (m, 1H), 3.44 (m, 1H), 2.54 (s, 3H) ppm.

Example 19

2-(5-Methoxypyridin-2-yl)-4-(3-methyl-1H-indazol-5-yl)-5-oxo-1,4,5,7-tetrahydrofuro[3,4-b]-pyridine-3-carbonitrile

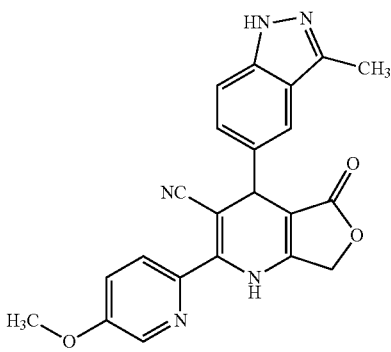

A solution of 172 mg (1.073 mmol) 3-methyl-1H-indazole-5-carbaldehyde (Example 1A), 188 mg (1.073 mmol) crude 3-amino-3-(6-methoxypyridin-3-yl)prop-2-enenitrile (Example 11A) and 242 mg (1.288 mmol) ethyl 4-(acetyloxy)-3-oxobutanoate [*Tetrahedron* 1978, 34, 1453-5] in 1-propanol (4 ml) was heated up to reflux for 12 h and then cooled to room temperature. Hydrochloric acid (3 M, 0.75 ml) was added, and the resulting mixture was again heated to 100° C. for 1 h. After cooling to room temperature, the solution was concentrated under reduced pressure, and the remaining solid was purified by preparative RP-HPLC (acetonitrile/water gradient) followed by flash chromatography (silica gel; dichloromethane/methanol gradient, final mixture 95:5 v/v) to yield the title compound as a white solid (30.7 mg, 7% of th.).

LC-MS (method 4): $R_t$=0.77 min; MS (ESIpos): m/z=400 (M+H)$^+$ $^1$H-NMR (400 MHz, DMSO-d$_6$): δ=12.64 (s, 1H), 10.43 (br. s, 1H), 8.43 (d, 1H), 7.92 (m, 1H), 7.60 (s, 1H), 7.46 (m, 1H), 7.36 (m, 1H), 7.01 (d, 1H), 5.00-4.83 (m, 2H), 4.79 (s, 1H), 3.91 (s, 3H), 2.54 (s, 3H) ppm.

Example 20

2-(2-Methoxyethyl)-4-(3-methyl-1H-indazol-5-yl)-5-oxo-1,4,5,7-tetrahydrofuro[3,4-b]pyridine-3-carbonitrile

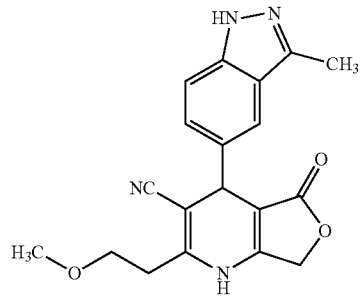

A solution of 100 mg (0.624 mmol) 3-methyl-1H-indazole-5-carbaldehyde (Example 1A), 87 mg (0.69 mmol) crude 5-methoxy-3-oxopentanenitrile (Example 12A), 120 mg (0.624 mmol) ethyl 4-(acetyloxy)-3-oxobutanoate [*Tetrahedron* 1978, 34, 1453-5] and 147 mg (1.87 mmol) ammonium acetate in 1-propanol (2 ml) was heated up to reflux for 12 h and then cooled to room temperature. Hydrochloric acid (3 M, 0.465 ml) was added, and the resulting mixture was again heated to 100° C. for 1 h. After cooling to room temperature, the solution was concentrated under reduced pressure, and the remaining solid was purified by preparative RP-HPLC (acetonitrile/water gradient, final mixture 9:1 v/v) to yield the title compound as a white solid (51.2 mg, 23% of th.).

LC-MS (method 4): $R_1$=0.69 min; MS (ESIpos): m/z=351 (M+H)$^+$ $^1$H-NMR (400 MHz, DMSO-d$_6$): δ=12.62 (s, 1H), 10.12 (s, 1H), 7.52 (s, 1H), 7.42 (m, 1H), 7.25 (m, 1H), 4.95-4.80 (m, 2H), 4.62 (s, 1H), 3.61 (t, 2H), 3.30 (s, 3H), 2.78-2.55 (m, 2H), 2.47 (s, 3H) ppm.

Example 21

4-[3-(2,3-Dihydro-1,4-benzodioxin-6-yl)-1H-indazol-5-yl]-2-methyl-5-oxo-1,4,5,7-tetrahydrofuro-[3,4-b]pyridine-3-carbonitrile

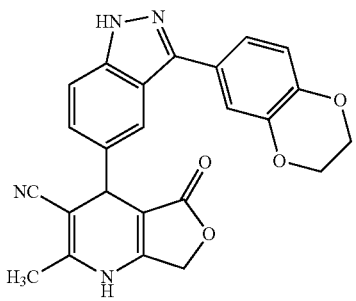 [SMILES: CC1=C(C#N)C(c2ccc3[nH]nc(-c4ccc5c(c4)OCCO5)c3c2)C2=C(COC2=O)N1]

To a degassed solution of 120 mg (0.323 mmol) 4-(3-bromo-1H-indazol-5-yl)-2-methyl-5-oxo-1,4,5,7-tetrahydrofuro[3,4-b]pyridine-3-carbonitrile (Example 24) and 69.8 mg (0.388 mmol) 2,3-dihydro-1,4-benzodioxin-6-ylboronic acid in anhydrous 1,4-dioxane (4.5 ml) were added under inert gas atmosphere 37.4 mg (0.032 mmol) tetrakis(triphenylphosphine)palladium(0) and aqueous sodium bicarbonate solution (2 M, 0.77 ml). The resulting mixture was stirred at 95° C. for 12 h. After cooling to room temperature and concentration under reduced pressure, the remaining solid was dissolved in ethyl acetate (20 ml). The solution was subsequently washed with water and brine, dried over sodium sulfate and concentrated under reduced pressure. The crude product was purified by preparative RP-HPLC (acetonitrile/water gradient, final mixture 95:5 v/v) to yield the title compound as a white solid (26 mg, 19% of th.).

LC-MS (method 4): $R_t$=0.82 min; MS (ESIpos): m/z=427 (M+H)$^+$ $^1$H-NMR (400 MHz, DMSO-d$_6$): δ=13.12 (s, 1H), 10.18 (br. s, 1H), 7.83 (s, 1H), 7.54 (d, 1H), 7.45-7.38 (m, 2H), 7.29 (m, 1H), 7.02 (d, 1H), 4.97-4.80 (m, 2H), 4.73 (s, 1H), 4.31 (s, 4H), 2.13 (s, 3H) ppm.

Example 22

2-Methyl-5-oxo-4-{3-[6-(propan-2-yloxy)pyridin-3-yl]-1H-indazol-5-yl}-1,4,5,7-tetrahydrofuro-[3,4-b]pyridine-3-carbonitrile

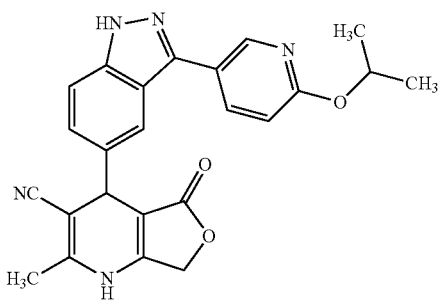 [SMILES: CC1=C(C#N)C(c2ccc3[nH]nc(-c4ccc(OC(C)C)nc4)c3c2)C2=C(COC2=O)N1]

To a degassed solution of 120 mg (0.323 mmol) 4-(3-bromo-1H-indazol-5-yl)-2-methyl-5-oxo-1,4,5,7-tetrahydrofuro[3,4-b]pyridine-3-carbonitrile (Example 24) and 70.2 mg (0.388 mmol) [6-(propan-2-yloxy)pyridin-3-yl]boronic acid in anhydrous 1,4-dioxane (3.5 ml) were added under inert gas atmosphere 37.4 mg (0.032 mmol) tetrakis(triphenylphosphine)palladium(0) and aqueous sodium bicarbonate solution (2 M, 0.77 ml). The resulting mixture was stirred at 100° C. for 12 h. After cooling to room temperature and concentration under reduced pressure, the remaining solid was dissolved in ethyl acetate (20 ml). The solution was subsequently washed with water and brine, dried over sodium sulfate and concentrated under reduced pressure. The crude product was purified by preparative RP-HPLC (acetonitrile/water gradient, final mixture 95:5 v/v) to yield the title compound as a white solid (27 mg, 19% of th.).

LC-MS (method 4): $R_t$=0.90 min; MS (ESIpos): m/z=428 (M+H)$^+$ $^1$H-NMR (400 MHz, DMSO-d$_6$): δ=13.25 (s, 1H), 10.17 (s, 1H), 8.73 (d, 1H), 8.22 (dd, 1H), 7.91 (s, 1H), 7.58 (s, 1H), 7.32 (d, 1H), 6.92 (d, 1H), 5.34 (sept, 1H), 4.97-4.80 (m, 2H), 4.75 (s, 1H), 2.13 (s, 3H), 1.35 (d, 6H) ppm.

Example 23

4-(3-Methyl-1H-indazol-5-yl)-3-oxo-1,4,6,7,8,9-hexahydro-3H-furo[3,4-c]quinolizine-5-carbonitrile

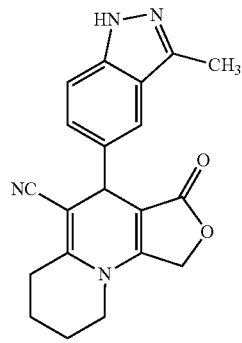 [SMILES: Cc1n[nH]c2ccc(C3C(C#N)=C4CCCCN4C4=C3C(=O)OC4)cc12]

A solution of 138 mg (0.86 mmol) 3-methyl-1H-indazole-5-carbaldehyde (Example 1A), 105 mg (1.073 mmol) piperidin-2-ylidene-ethanenitrile [WO 2008/071451, Synth. Prep. 5] and 194 mg (1.031 mmol) ethyl 4-(acetyloxy)-3-oxobutanoate [Tetrahedron 1978, 34, 1453-5] in 1-propanol (3 ml) was heated up to reflux for 12 h and then cooled to room temperature. Hydrochloric acid (3 M, 0.60 ml) was added, and the resulting mixture was again heated to 100° C. for 1 h. After cooling to room temperature, the solution was concentrated under reduced pressure, and the remaining solid was purified by preparative TLC (silica gel; eluent: dichloromethane/ethanol 20:1 v/v). The product was further purified by trituration in a mixture of acetonitrile/methanol/water (2:6:1 v/v/v). The precipitate was collected by filtration and dried in vacuo to yield the title compound as a white solid (18 mg, 6% of th.).

LC-MS (method 4): $R_t$=0.78 min; MS (ESIpos): m/z=347 (M+H)$^+$ $^1$H-NMR (400 MHz, DMSO-d$_6$): δ=12.62 (s, 1H), 7.52 (s, 1H), 7.43 (d, 1H), 7.27 (d, 1H), 5.12-4.98 (m, 2H), 4.63 (s, 1H), 3.60-3.39 (m, 2H), 2.75-2.60 (m, 2H), 2.54 (s, 3H), 1.90-1.80 (m, 2H), 1.78-1.62 (m, 2H) ppm.

Example 24

4-(3-Bromo-1H-indazol-5-yl)-2-methyl-5-oxo-1,4,5,7-tetrahydrofuro[3,4-b]pyridine-3-carbonitrile

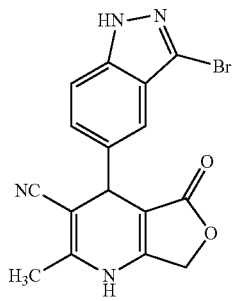

A solution of 2.45 g (10.89 mmol) 3-bromo-1H-indazole-5-carbaldehyde (Example 13A), 0.931 g (10.89 mmol) 3-aminobut-2-enenitrile and 2.09 g (10.89 mmol) ethyl 4-(acetyloxy)-3-oxobutanoate [*Tetrahedron* 1978, 34, 1453-5] in 1-propanol (50 ml) was heated up to reflux for 12 h and then cooled to room temperature. Hydrochloric acid (3 M, 14 ml) was added, and the resulting mixture was again heated to 100° C. for 1 h. After cooling to room temperature, the solution was concentrated under reduced pressure, and the remaining solid was purified by preparative RP-HPLC (acetonitrile/water gradient, final mixture 95:5 v/v) to yield the title compound as a pale yellow solid (756 mg, 19% of th.).

LC-MS (method 5): $R_t$=1.52 min; MS (ESIpos): m/z=371 (M+H)+

$^1$H-NMR (400 MHz, DMSO-$d_6$): δ=13.44 (s, 1H), 10.21 (s, 1H), 7.57 (m, 1H), 7.41-7.37 (m, 2H), 5.00-4.82 (m, 2H), 4.72 (s, 1H), 2.13 (s, 3H) ppm.

Example 25

2-(4-Fluorophenyl)-4-(3-methyl-1H-indazol-5-yl)-5-oxo-1,4,5,7-tetrahydrofuro[3,4-b]pyridine-3-carbonitrile

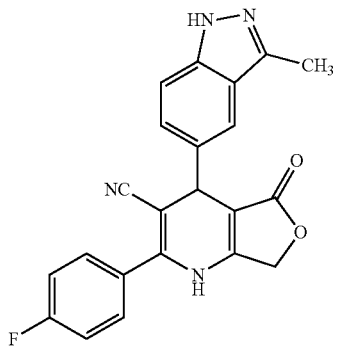 [SMILES: Cc1n[nH]c2ccc(C3C(C#N)=C(c4ccc(F)cc4)NC4=C3C(=O)OC4)cc12]

A solution of 241 mg (1.51 mmol) 3-methyl-1H-indazole-5-carbaldehyde (Example 1A), 244 mg (1.51 mmol) 3-amino-3-(4-fluorophenyl)prop-2-enenitrile [*J. Heterocyclic Chem.* 1998, 35, 805-810] and 340 mg (1.81 mmol) ethyl 4-(acetyloxy)-3-oxobutanoate [*Tetrahedron* 1978, 34, 1453-5] in 1-propanol (4 ml) was heated up to reflux for 12 h and then cooled to room temperature. Hydrochloric acid (3 M, 1.05 ml) was added, and the resulting mixture was again heated to 100° C. for 1 h. After cooling to room temperature, the solution was concentrated under reduced pressure, and the remaining solid was purified by preparative RP-HPLC (acetonitrile/water gradient, final mixture 95:5 v/v) to yield the title compound as a white solid (200 mg, 34% of th.).

LC-MS (method 4): $R_t$=0.83 min; MS (ESIpos): m/z=387 (M+H)+

$^1$H-NMR (400 MHz, DMSO-$d_6$): δ=12.64 (s, 1H), 10.39 (s, 1H), 7.70-7.63 (m, 2H), 7.60 (s, 1H), 7.46 (d, 1H), 7.43-7.33 (m, 3H), 5.00-4.84 (m, 2H), 4.78 (s, 1H), 2.54 (s, 3H) ppm.

Example 26 and Example 27

2-(4-Fluorophenyl)-4-(3-methyl-1H-indazol-5-yl)-5-oxo-1,4,5,7-tetrahydrofuro[3,4-b]pyridine-3-carbonitrile (Enantiomer 1 and 2)

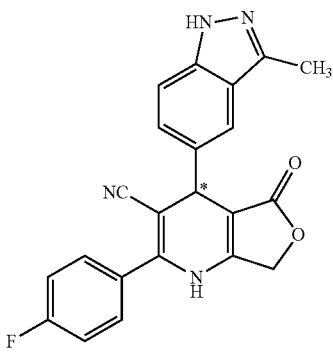 [SMILES: Cc1n[nH]c2ccc(C3C(C#N)=C(c4ccc(F)cc4)NC4=C3C(=O)OC4)cc12]

The racemic compound from Example 25 (100 mg) was separated into the enantiomers by HPLC chromatography on a chiral phase [column: Daicel Chiralpak AS-H, 5 µm, 250 mm×20 mm; eluent: iso-hexane/ethanol 50:50 v/v; flow rate: 15 ml/min; temperature: 30° C.; UV detection: 220 nm]:

Example 26

Enantiomer 1

Yield: 38 mg (chemical purity >98.5%, >99.5% ee)

$R_t$=4.06 min [column: Daicel Chiralpak AS-H, 5 µm, 250 mm×4.6 mm; eluent: iso-hexane/ethanol 50:50; flow rate: 1 ml/min; temperature: 40° C.; UV detection: 220 nm].

Example 27

Enantiomer 2

Yield: 51 mg (chemical purity >99.5%, >99.5% ee)
$R_t$=8.43 min [column: Daicel Chiralpak AS-H, 5 μm, 250 mm×4.6 mm; eluent: iso-hexane/ethanol 50:50; flow rate: 1 ml/min; temperature: 40° C.; UV detection: 220 nm].

Example 28

2-(4-Chlorophenyl)-4-(3-methyl-1H-indazol-5-yl)-5-oxo-1,4,5,7-tetrahydrofuro[3,4-b]pyridine-3-carbonitrile

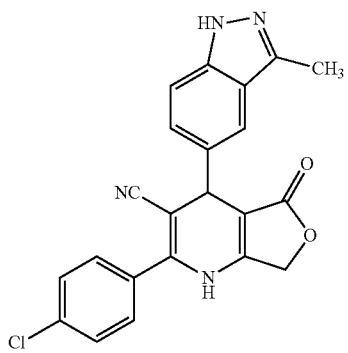 [SMILES: Cc1n[nH]c2ccc(C3C(C#N)=C(c4ccc(Cl)cc4)NC4=C3C(=O)OC4)cc12]

A solution of 245 mg (1.53 mmol) 3-methyl-1H-indazole-5-carbaldehyde (Example 1A), 300 mg (1.68 mmol) 3-amino-3-(4-chlorophenyl)prop-2-enenitrile [*J. Heterocyclic Chem.* 1998, 35, 805-810] and 287 mg (1.53 mmol) ethyl 4-(acetyloxy)-3-oxobutanoate [*Tetrahedron* 1978, 34, 1453-5] in 1-propanol (6 ml) was heated up to reflux for 12 h and then cooled to room temperature. Hydrochloric acid (3 M, 1.2 ml) was added, and the resulting mixture was again heated to 100° C. for 1 h. After cooling to room temperature, the solution was concentrated under reduced pressure, and the remaining solid was purified by preparative RP-HPLC (acetonitrile/water gradient, final mixture 95:5 v/v) to yield the title compound as a pale yellow solid (248 mg, 40% of th.).

LC-MS (method 4): $R_t$=0.88 min; MS (ESIpos): m/z=403 (M+H)$^+$.

$^1$H-NMR (400 MHz, DMSO-d$_6$): δ=12.64 (s, 1H), 10.41 (s, 1H), 7.63 (m, 4H), 7.60 (s, 1H), 7.46 (d, 1H), 7.35 (m, 1H), 5.00-4.84 (m, 2H), 4.79 (s, 1H), 2.54 (s, 3H) ppm.

Example 29

2-(4-Chloro-3-fluorophenyl)-4-(3-methyl-1H-indazol-5-yl)-5-oxo-1,4,5,7-tetrahydrofuro[3,4-b]-pyridine-3-carbonitrile

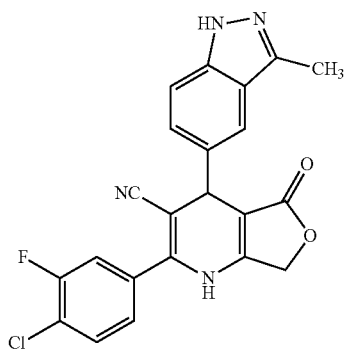 [SMILES: Cc1n[nH]c2ccc(C3C(C#N)=C(c4ccc(Cl)c(F)c4)NC4=C3C(=O)OC4)cc12]

A solution of 148 mg (0.93 mmol) 3-methyl-1H-indazole-5-carbaldehyde (Example 1A), 200 mg (1.02 mmol) 3-amino-3-(4-chloro-3-fluorophenyl)prop-2-enenitrile (Example 14A) and 174 mg (0.93 mmol) ethyl 4-(acetyloxy)-3-oxobutanoate [*Tetrahedron* 1978, 34, 1453-5] in 1-propanol (3.5 ml) was heated up to reflux for 12 h and then cooled to room temperature. Hydrochloric acid (3 M, 0.76 ml) was added, and the resulting mixture was again heated to 100° C. for 1 h. After cooling to room temperature, the solution was concentrated under reduced pressure, and the remaining solid was purified by preparative RP-HPLC (acetonitrile/water gradient, final mixture 95:5 v/v) followed by preparative TLC (silica gel; eluent: dichloromethane/methanol 20:1 v/v) to yield the title compound as a white solid (50 mg, 13% of th.).

LC-MS (method 2): $R_t$=1.02 min; MS (ESIpos): m/z=421 (M+H)$^+$ $^1$H-NMR (400 MHz, DMSO-d$_6$): δ=12.63 (s, 1H), 10.46 (s, 1H), 7.80 (m, 1H), 7.73 (m, 1H), 7.60 (s, 1H), 7.52-7.44 (m, 2H), 7.36 (m, 1H), 5.00-4.84 (m, 2H), 4.79 (s, 1H), 2.54 (s, 3H) ppm.

Example 30

2-(3,5-Difluorophenyl)-4-(3-methyl-1H-indazol-5-yl)-5-oxo-1,4,5,7-tetrahydrofuro[3,4-b]pyridine-3-carbonitrile

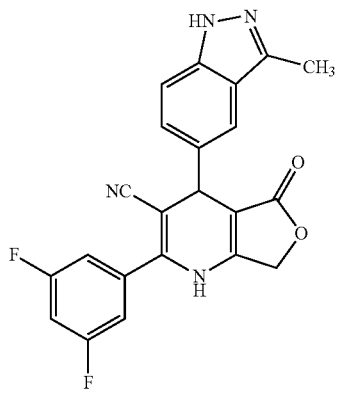 [SMILES: Cc1n[nH]c2ccc(C3C(C#N)=C(c4cc(F)cc(F)c4)NC4=C3C(=O)OC4)cc12]

A solution of 162 mg (1.01 mmol) 3-methyl-1H-indazole-5-carbaldehyde (Example 1A), 200 mg (1.11 mmol) 3-amino-3-(3,5-difluorophenyl)prop-2-enenitrile (Example 15A) and 190 mg (1.01 mmol) ethyl 4-(acetyloxy)-3-oxobutanoate [*Tetrahedron* 1978, 34, 1453-5] in 1-propanol (4 ml) was heated up to reflux for 12 h and then cooled to room temperature. Hydrochloric acid (3 M, 0.80 ml) was added, and the resulting mixture was again heated to 100° C. for 1 h. After cooling to room temperature, the solution was concentrated under reduced pressure, and the remaining solid was purified by preparative RP-HPLC (acetonitrile/water gradient, final mixture 95:5 v/v) to yield the title compound as a pale yellow solid (39 mg, 10% of th.).

LC-MS (method 4): $R_t$=0.86 min; MS (ESIpos): m/z=405 (M+H)$^+$ $^1$H-NMR (400 MHz, DMSO-d$_6$): δ=12.63 (s, 1H), 10.48 (s, 1H), 7.60 (s, 1H), 7.52-7.32 (m, 5H), 5.00-4.84 (m, 2H), 4.79 (s, 1H), 2.54 (s, 3H) ppm.

Example 31

2-(2,4-Difluorophenyl)-4-(3-methyl-1H-indazol-5-yl)-5-oxo-1,4,5,7-tetrahydrofuro[3,4-b]pyridine-3-carbonitrile

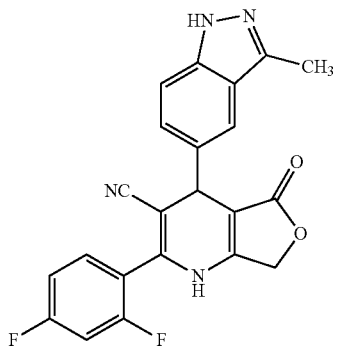 [SMILES: Cc1n[nH]c2ccc(C3C(C#N)=C(c4ccc(F)cc4F)NC4=C3C(=O)OC4)cc12]

A solution of 232 mg (1.45 mmol) 3-methyl-1H-indazole-5-carbaldehyde (Example 1A), 287 mg (1.59 mmol) 3-amino-3-(2,4-difluorophenyl)prop-2-enenitrile (Example 16A) and 273 mg (1.45 mmol) ethyl 4-(acetyloxy)-3-oxobutanoate [*Tetrahedron* 1978, 34, 1453-5] in 1-propanol (6 ml) was heated up to reflux for 12 h and then cooled to room temperature. Hydrochloric acid (3 M, 0.80 ml) was added, and the resulting mixture was again heated to 100° C. for 1 h. After cooling to room temperature, the solution was concentrated under reduced pressure, and the remaining solid was purified by preparative RP-HPLC (acetonitrile/water gradient, final mixture 95:5 v/v) followed by flash chromatography (silica gel; dichloromethane/methanol gradient, final mixture 95:5 v/v) to yield the title compound as a pale yellow solid (62 mg, 10% of th.).

LC-MS (method 4): $R_t$=0.82 min; MS (ESIpos): m/z=405 $(M+^{14})^+$ $^1$H-NMR (400 MHz, DMSO-$d_6$): δ=12.66 (s, 1H), 10.52 (s, 1H), 7.69 (m, 1H), 7.61 (s, 1H), 7.58-7.48 (m, 2H), 7.36 (m, 1H), 7.30 (m, 1H), 5.00-4.84 (m, 2H), 4.81 (s, 1H), 2.54 (s, 3H) ppm.

Example 32

2-Methyl-5-oxo-4-{3-[3-(trifluoromethyl)phenyl]-1H-indazol-5-yl}-1,4,5,7-tetrahydrofuro[3,4-b]-pyridine-3-carbonitrile

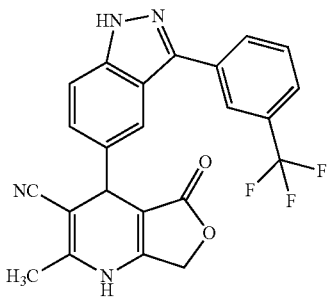 [SMILES: CC1=C(C#N)C(c2ccc3[nH]nc(-c4cccc(C(F)(F)F)c4)c3c2)C2=C(COC2=O)N1]

To a degassed solution of 120 mg (0.323 mmol) 4-(3-bromo-1H-indazol-5-yl)-2-methyl-5-oxo-1,4,5,7-tetrahydrofuro[3,4-b]pyridine-3-carbonitrile (Example 24) and 73.7 mg (0.388 mmol) [3-(trifluoromethyl)phenyl]boronic acid in anhydrous 1,4-dioxane (4.8 ml) were added under argon atmosphere 37.4 mg (0.032 mmol) tetrakis(triphenylphosphine)palladium(0) and aqueous sodium bicarbonate solution (2 M, 0.77 ml). The resulting mixture was stirred at 95° C. for 12 h. After cooling to room temperature and concentration under reduced pressure, the remaining solid was dissolved in ethyl acetate (20 ml). The solution was subsequently washed with water and brine, dried over sodium sulfate and concentrated under reduced pressure. The crude product was purified by preparative RP-HPLC (first run: acetonitrile/water gradient, final mixture 95:5 v/v; second run: methanol/water isocratic 75:25 v/v) to yield the title compound as a white solid (6 mg, 4% of th.).

LC-MS (method 6): $R_t$=2.14 min; MS (ESIpos): m/z=437 $(M+H)^+$.

$^1$H-NMR (400 MHz, DMSO-$d_6$): δ=13.47 (s, 1H), 10.20 (s, 1H), 8.29 (d, 1H), 8.23 (s, 1H), 7.83 (s, 1H), 7.84-7.76 (m, 2H), 7.63 (d, 1H), 7.37 (d, 1H), 4.90 (m, 2H), 4.76 (s, 1H), 2.13 (s, 3H) ppm.

The following compounds were prepared in analogy to the procedure described for Example 19; purification was carried out by preparative silica gel chromatography using a dichloromethane/methanol gradient.

| Example | Name/Structure (yield) | Analytical data |
|---|---|---|
| 33 | 4-(3-Methyl-1H-indazol-5-yl)-5-oxo-2-[4-(trifluoromethyl)phenyl]-1,4,5,7-tetra-hydrofuro[3,4-b]pyridine-3-carbonitrile<br>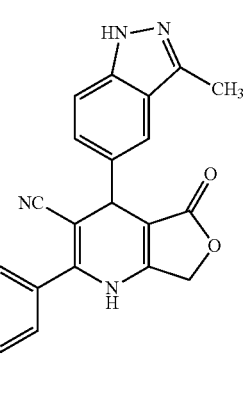<br>(6% of th.)[1] | LC-MS (method 4):<br>$R_t$ = 0.93 min; m/z = 437 (M + H)$^+$<br>$^1$H-NMR (400 MHz, DMSO-d$_6$):<br>δ = 12.64 (s, 1H), 10.49 (s, 1H), 7.94 (d, 2H), 7.81 (d, 2H), 7.62 (s, 1H), 7.47 (d, 1H), 7.37 (d, 1H), 4.94 (m, 2H), 4.82 (s, 1H), 2.54 (s, 3H) ppm. |
| 34 | 4-(6-Fluoro-1H-indazol-5-yl)-5-oxo-2-[4-(trifluoromethyl)phenyl]-1,4,5,7-tetra-hydrofuro[3,4-b]pyridine-3-carbonitrile<br>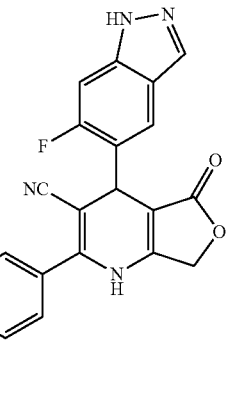<br>(26% of th.) | LC-MS (method 2):<br>$R_t$ = 1.04 min; m/z = 441 (M + H)$^+$<br>$^1$H-NMR (400 MHz, DMSO-d$_6$):<br>δ = 13.17 (s, 1H), 10.57 (s, 1H), 8.11 (s, 1H), 7.94 (m, 2H), 7.86-7.81 (m, 3H), 7.36 (d, 1H), 5.06 (s, 1H), 4.95 (m, 2H) ppm. |
| 35 | 2-(4-Chlorophenyl)-4-(6-fluoro-1H-indazol-5-yl)-5-oxo-1,4,5,7-tetrahydro-furo[3,4-b]pyridine-3-carbonitrile<br>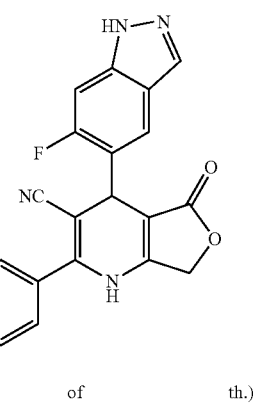<br>(33% of th.) | LC-MS (method 4):<br>$R_t$ = 0.88 min; m/z = 407 (M + H)$^+$<br>$^1$H-NMR (400 MHz, DMSO-d$_6$):<br>δ = 13.16 (s, 1H), 10.48 (s, 1H), 8.10 (s, 1H), 7.80 (d, 2H), 7.62 (m, 4H), 7.37 (d, 1H), 5.02 (s, 1H), 4.93 (m, 2H) ppm. |

-continued

| Example | Name/Structure (yield) | Analytical data |
|---|---|---|
| 36 | 4-(6-Fluoro-1H-indazol-5-yl)-2-(4-fluoro-phenyl)-5-oxo-1,4,5,7-tetrahydro-furo[3,4-b]pyridine-3-carbonitrile 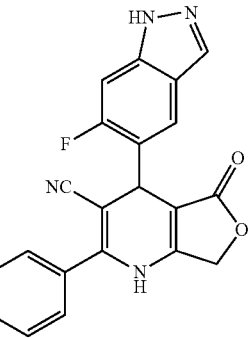 (28% of th.) | LC-MS (method 4):<br>$R_t$ = 0.82 min; m/z = 391 (M + H)$^+$<br>$^1$H-NMR (400 MHz, DMSO-$d_6$):<br>δ = 13.15 (s, 1H), 10.45 (s, 1H), 8.10 (s, 1H), 7.82 (d, 1H), 7.65 (m, 2H), 7.42-7.34 (m, 3H), 5.02 (s, 1H), 4.93 (m, 2H) ppm. |

[1] after further purification by preparative RP-HPLC [column: Sunfire C18, 5 μm, 19 mm × 150 mm; eluent: acetonitrile/water gradient, final mixture 70:30 v/v; flow rate: 25 ml/min; temperature: 30° C.; UV detection: 210 nm].

The following compounds were prepared in analogy to the procedure described for Example 16; purification was carried out by preparative RP-HPLC using an acetonitrile/water+ 0.1% TFA gradient.

| Example | Name/Structure (yield) | Analytical data |
|---|---|---|
| 37 | 4-(6-Fluoro-1H-indazol-5-yl)-5-oxo-2-(trifluoromethyl)-1,4,5,7-tetrahydro-furo[3,4-b]pyridine-3-carbonitrile 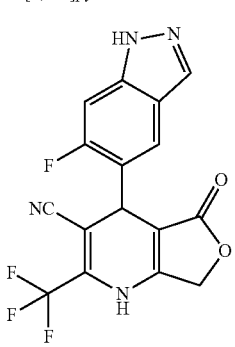 (5% of th.) | LC-MS (method 2):<br>$R_t$ = 0.86 min; m/z = 365 (M + H)$^+$<br>$^1$H-NMR (400 MHz, DMSO-$d_6$):<br>δ = 13.20 (s, 1H), 11.10 (s, 1H), 8.11 (s, 1H), 7.81 (d, 1H), 7.38 (d, 1H), 5.12 (s, 1H), 4.94 (m, 2H) ppm. |

| Example | Name/Structure (yield) | Analytical data |
| --- | --- | --- |
| 38 | 4-(6-Fluoro-3-methyl-1H-indazol-5-yl)-5-oxo-2-(trifluoromethyl)-1,4,5,7-tetra-hydrofuro[3,4-b]pyridine-3-carbonitrile<br><br>(10% of th.) | LC-MS (method 4):<br>$R_t$ = 0.79 min; m/z = 379 (M + H)$^+$<br>$^1$H-NMR (400 MHz, DMSO-d$_6$):<br>δ = 12.77 (s, 1H), 11.07 (s, 1H), 7.72 (d, 1H), 7.28 (d, 1H), 5.11 (s, 1H), 4.94 (m, 2H), 2.50 (s, 3H) ppm. |

Example 39

4-(3-Methyl-1H-indazol-5-yl)-5-oxo-2-(propan-2-yl)-1,4,5,7-tetrahydrofuro[3,4-b]pyridine-3-carbonitrile

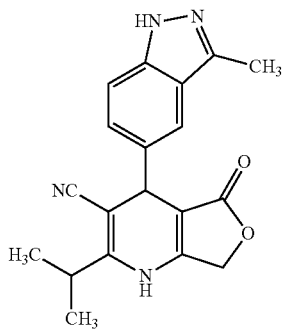 [SMILES: Cc1n[nH]c2ccc(C3C(C#N)=C(C(C)C)NC4=C3C(=O)OC4)cc12]

A solution of 50 mg (0.312 mmol) 3-methyl-1H-indazole-5-carbaldehyde (Example 1A), 34 mg (0.312 mmol) 3-amino-4-methylpent-2-enenitrile [P. Stanetty et al., *Monatshefte für Chemie* 1999, 130, 441-450] and 59 mg (0.312 mmol) ethyl 4-(acetoxy)-3-oxobutanoate [preparation: U.S. Pat. No. 4,720,572 (Example 1)] in 1-propanol (1 ml) was stirred at reflux temperature overnight. Then, concentrated hydrochloric acid (60 μl) and water (175 μl) were added, and stirring was continued at 100° C. for 1 h. After cooling to room temperature, the mixture was directly purified by preparative RP-HPLC (acetonitrile/water+0.1% TFA gradient) to yield 50 mg (48% of th.) of the racemic title compound.

LC-MS (method 4): $R_t$=0.77 min; MS (ESIpos): m/z=335 (M+H)$^+$ $^1$H-NMR (400 MHz, DMSO-d$_6$): δ=12.62 (br. s, 1H), 9.83 (s, 1H), 7.49 (s, 1H), 7.42 (d, 1H), 7.22 (d, 1H), 4.90 (dd, 2H), 4.61 (s, 1H), 3.02 (sept, 1H), 2.48 (s, 3H), 1.20 (dd, 6H) ppm.

B. EVALUATION OF BIOLOGICAL ACTIVITY

Demonstration of the activity of the compounds of the present invention may be accomplished through in vitro, ex vivo, and in vivo assays that are well known in the art. For example, to demonstrate the activity of the compounds of the present invention, the following assays may be used.

c-Met Receptor Tyrosine Kinase Activity Assay (NADH Read-Out):

Recombinant human c-Met protein (Invitrogen, Carlsbad, Calif., USA) is used. As substrate for the kinase reaction the peptide KKKSPGEYVNIEFG (JPT, Germany) is used. For the assay, 1 μL of a 51-fold concentrated solution of the test compound in DMSO is pipetted into a white 384-well microtiter plate (Greiner Bio-One, Frickenhausen, Germany). 25 μL of a solution of c-Met (final concentration 30 nM) and pyruvate kinase/lactate dehydrogenase (Roche Diagnostics, Mannheim, Germany; final concentration 8 mg/L) in assay buffer [3-(N-morpholino)propane-sulfonic acid (MOPS), 50 mM, pH 7; MgCl$_2$, 10 mM; bovine serum albumin (BSA), 0.01%; Triton X 100, 0.01%; DTT, 2 mM] are added, and the mixture is incubated for 5 min at room temperature. Then, the kinase reaction is started by the addition of 25 μL of a solution of adenosine triphosphate (ATP, final concentration 30 μM), substrate (final concentration 100 μM), nicotinamide adenine dinucleotide (NADH, final concentration 50 μM) and dithiothreitol (DTT, final concentration 2 mM) in assay buffer, and the resulting mixture is incubated for a reaction time of 100 min at 32° C.

Subsequently, the amount of phosphorylated substrate is evaluated by measurement of the decrease of NADH fluorescence. Therefore, the fluorescence emissions at 465 nm after excitation at 340 nm is measured in a fluorescence reader, e.g. Tecan Ultra (Tecan, Mannedorf, Switzerland). The data are normalised (enzyme reaction without inhibitor=0% inhibition; all other assay components but no enzyme=100% inhibition). Normally, test compounds are tested on the same microtiter plate at 9 different concentrations in the range of 10 μM to 1 nM (10 μM, 3.1 μM, 1.0 μM, 0.3 μM, 0.1 μM, 0.03 μM, 0.01 μM, 0.003 μM, 0.001 μM; dilution series prepared before the assay at the level of the 51-fold concentrated stock solutions by serial 1:3 dilutions) in duplicate for each concentration, and IC$_{50}$ values are calculated using an inhouse software.

Compounds of the invention, when tested in this assay, demonstrated the ability to inhibit c-Met tyrosine kinase activity at IC$_{50}$ values of less than 10 μM, preferably at less than 1 μM.

Some representative IC$_{50}$ values are listed in the table below:

| Example No. | IC$_{50}$ [μM] |
|---|---|
| 2 | 0.014 |
| 8 | 0.11 |
| 18 | 0.015 |
| 22 | 0.009 |
| 25 | 0.016 |
| 36 | 0.019 |
| 38 | 0.020 |
| 39 | 0.014 | c-Met Receptor Tyrosine Kinase Homogeneous Time-Resolved Fluorescence Assay (Alternative Format):

The N-terminally His6-tagged recombinant kinase domain of the human c-Met (amino acids 960-1390), expressed in insect cells (SF21) and purified by Ni-NTA affinity chromatography and consecutive size exclusion chromatography (Superdex 200), is used. Alternatively, commercially available c-Met (Millipore) can be used. As substrate for the kinase reaction, the biotinylated poly-Glu,Tyr (4:1) copolymer (#61GTOBLC, Cis Biointernational, Marcoule, France) is used.

For the assay, 50 mL of a 100-fold concentrated solution of the test compound in DMSO is pipetted into a black low-volume 384-well microtiter plate (Greiner Bio-One, Frickenhausen, Germany). 2 μL of a solution of c-Met in assay buffer [25 mM Hepes/NaOH, pH 7.5; 5 mM MgCl$_2$; 5 mM MnCl$_2$; 2 mM dithiothreitol; 0.1% (v/v) Tween 20 (Sigma); 0.1% (w/v) bovine serum albumin] are added, and the mixture is incubated for 15 min at 22° C. to allow pre-binding of the test compound to the enzyme before the start of the kinase reaction. Then, the kinase reaction is started by the addition of 3 μL of a solution of adenosine triphosphate (ATP, 16.7 μM; final concentration in the 5 μL assay volume is 10 μM) and substrate (2.27 μg/mL, final concentration in the 5 μL assay volume is 1.36 μg/mL~30 nM) in assay buffer, and the resulting mixture is incubated for a reaction time of 30 min at 22° C. The concentration of c-Met in the assay is adjusted depending on the activity of the enzyme lot and is appropriately chosen to have the assay in the linear range; typical enzyme concentrations are in the range of about 0.03 nM (final concentration in the 5 μL assay volume). The reaction is stopped by the addition of 5 μL of a solution of HTRF detection reagents [40 nM streptavidine-XLent and 2.4 nM PT66-Eu-chelate, an europium-chelate labelled anti-phosphotyrosine antibody (Perkin-Elmer)] in an aqueous EDTA solution [100 mM EDTA, 0.2% (w/v) bovine serum albumin in 50 mM HEPES/NaOH, pH 7.5].

The resulting mixture is incubated for 1 h at 22° C. to allow the binding of the biotinylated phosphorylated peptide to the streptavidine-XLent and the PT66-Eu-chelate. Subsequently, the amount of phosphorylated substrate is evaluated by measurement of the resonance energy transfer from the PT66-Eu-chelate to the streptavidine-XLent. Therefore, the fluorescence emissions at 620 nm and 665 nm after excitation at 350 nm are measured in an HTRF reader, e.g. Rubystar (BMG Lab-technologies, Offenburg, Germany) or Viewlux (Perkin-Elmer). The ratio of the emissions at 665 nm and at 622 nm is taken as the measure for the amount of phosphorylated substrate. The data are normalised (enzyme reaction without inhibitor=0% inhibition; all other assay components but no enzyme=100% inhibition). Normally, test compounds are tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM; dilution series prepared before the assay at the level of the 100-fold concentrated stock solutions by serial 1:3 dilutions) in duplicate for each concentration, and IC$_{50}$ values are calculated by a 4-parameter-fit using an inhouse software.

Compounds of the invention, when tested in this assay, demonstrated the ability to inhibit c-Met tyrosine kinase activity at IC$_{50}$ values of less than 10 μM, preferably at less than 1 μM.

Some representative IC$_{50}$ values are listed in the table below:

| Example No. | IC$_{50}$ [μM] |
|---|---|
| 2 | 0.001 |
| 7 | 0.028 |
| 8 | 0.25 |
| 16 | 0.007 |
| 18 | 0.002 |
| 31 | 0.002 |
| 38 | 0.020 |

Phospho-c-Met Assay:

This is a cell based, ELISA-like assay [Mesoscale Discovery (MSD), Gaithersburg, Md., USA] using MKN-45 tumor cells (gastric carcinoma, purchased from ATCC) without growth factor stimulation. The cells are plated in full growth media (10 000 cells/well) in 96-well plates on day one. On day two, after a two-hour drug treatment in serum-free media, cells are washed and then lysed (60 μl/well using MSD recommended lysis buffer) and frozen at −80° C. Also on day two, non-specific antibody-binding sites on the MSD phospho-Met plates are blocked with MSD Blocking Solution A overnight at 4° C. On day three, frozen lysates are thawed on ice, and 25 μl of lysate is transferred to the MSD phospho-Met plate, for 1 hour with shaking, after washing once with Tris-buffered saline+0.05% Tween 20 (TBST). After removing the unbound proteins, the Sulfa-TAG anti-Met antibody from MSD is added at a final concentration of 5 nM in antibody dilution buffer (following protocol of MSD) to the plate for 1 hour with shaking. The plate is then washed with TBST buffer three times before adding 1×MSD Read Buffer. The plate is then read on the MSD Discovery Workstation instrument. Raw data, including wells with 10 μM of a reference compound (minimum signal), and DMSO wells without any drug treatment (maximum signal), are entered into the Analyze 5 program for IC$_{50}$ value determinations.

Cellular Phospho-c-Met Assay:

Human gastric adenocarcinoma cells (MKN45, purchased from ATCC) seeded on 384-well microtiter plates (9000 cells/well) are incubated in 25 μl full growth media for 24 h at 37° C. with 5% CO$_2$. On day two, after a two-hour drug treatment in serum-reduced media containing 0.1% FCS, cells are washed and lysed. Lysates are transferred to BSA-blocked plates with prebound c-Met capture antibody [purchased from Mesoscale Discovery (MSD), Gaithersburg, Md., USA] for 1 hour with shaking, after washing once with Tris-buffered saline+0.05% Tween 20 (TBST). Following the MSD protocol, the Sulfa-TAG anti-phospho-c-Met detection antibody is added at a final concentration of 5 nM in antibody dilution buffer to the plate for 1 hour with shaking at RT. After washing the wells with Tris buffer, 1× reading buffer is added, and the plates are measured on the Sector Imager 6000 (purchased from Mesoscale). $IC_{50}$ values are calculated from dose-response curves using Marquardt-Levenberg-Fit.

In-Vitro Tumor Cell Proliferation Assay:

The adherent tumor cell proliferation assay used to test the compounds of the present invention involves a read-out called Cell Titre-Glo developed by Promega [B. A. Cunningham, "A Growing Issue: Cell Proliferation Assays. Modern kits ease quantification of cell growth", *The Scientist* 2001, 15 (13), 26; S. P. Crouch et al., "The use of ATP bioluminescence as a measure of cell proliferation and cytotoxicity", *Journal of Immunological Methods* 1993, 160, 81-88]. Generation of a luminescent signal corresponds to the amount of ATP present, which is directly proportional to the number of metabolically active (proliferating) cells.

H460 cells (lung carcinoma, purchased from ATCC) are plated in 96-well plates at 3000 cells/well in complete media with 10% fetal calf serum and incubated 24 hours at 37° C. Twenty-four hours after plating, test compounds are added over a final concentration range of 10 nM to 20 µM in serial dilutions at a final DMSO concentration of 0.2%. Cells are incubated for 72 hours at 37° C. in complete growth media after addition of the test compound. On day 4, using a Promega Cell Titre-Glo Luminescent® assay kit, the cells are lysed, and 100 µl of substrate/buffer mixture is added to each well, mixed and incubated at room temperature for 8 minutes. The samples are read on a luminometer to measure the amount of ATP present in the cell lysates from each well, which corresponds to the number of viable cells in that well. Values read at 24-hour incubation are subtracted as Day 0. For determination of $IC_{50}$ values, a linear regression analysis can be used to determine the drug concentration which results in a 50% inhibition of cell proliferation using this assay format. This protocol can be applied to different cell lines of interest, which include, but not limited to, CAKI-1, MNK-45, GTL-16, $HCC_{2998}$, K562, H441, K812, MEG01, SUP15 and HCT116.

In-Vitro Clearance Determinations with Liver Microsomes:

Microsomal incubations are performed at 37° C. in a total volume of 1.5 ml using a modified Janus® robotic system (Perkin-Elmer). The incubation mixtures contain 0.5 mg/ml microsomal protein, ~1 µM substrate, 0.05 M potassium phosphate buffer (pH 7.4), 1 mM EDTA, 5 mM glucose-6-phosphate and 1.5 U/ml glucose-6-phosphate dehydroxygenase from *Leuconostoc Mesenteroides*. Although the reaction is started by adding $NADP^+$ (final concentration 1 mM), FMO-activity is maintained. The final acetonitrile (ACN) concentration is ≤1%.

Aliquots of 125 µl are withdrawn from the incubation mixture after 2, 5, 10, 20, 30 and 60 min or after 2, 10, 20, 30, 50, 70 and 90 min, depending on the metabolic stability of the compound, and are dispensed in a 96-well plate containing 250 µl ACN to stop the reaction. After centrifugation, supernatants are analyzed by MSMS (typically API 2000 or API 3000).

Calculation of in-vitro clearance values (CL) from half-life data ($t_{1/2}$) in liver microsomes, reflecting substrate depletion, is performed using the following equation [J. B. Houston, *Biochem. Pharmacol.* 1994, 47 (9), 1469-79; R. S. Obach et al., *J. Pharmacol. Exp. Ther.* 1997, 283 (1), 46-58]:

$$CL_{intrinsic}'[\text{ml}/(\text{min}\cdot\text{kg})]=(0.693/\text{in vitro } t_{1/2} \text{ [min]})\cdot (\text{liver weight [g liver/kg body mass]})\cdot(\text{microsomal protein [mg]/liver weight [g]})/(\text{microsomal protein [mg]/incubation volume[ml]}).$$

The $CL_{blood}$ value is estimated using the non-restricted well-stirred model [K. S. Pang, M. Rowland, *J. Pharmacokin. Biopharm.* 1977, 5 (6), 625-53]:

$$CL_{blood} \text{ well-stirred } [\text{L}/(\text{h}\cdot\text{kg})]=(Q_H \text{ [L}/(\text{h}\cdot\text{kg})]\cdot CL_{intrinsic}'[\text{L}/(\text{h}\cdot\text{kg})])/(Q_H[\text{L}/(\text{h}\cdot\text{kg})]+CL_{intrinsic}'[\text{L}/(\text{h}\cdot\text{kg})]).$$

Specific liver weights and hepatic blood flows ($Q_H$) are 32 g/kg body mass and 4.2 L/(h·kg), respectively, for rats, and 21 g/kg body mass and 1.32 L/(h·kg), respectively, for man. For both species, a specific microsomal protein content in the liver of 40 mg/g is assumed. Species-specific factors for the prediction of in-vivo clearance values for other species are shown below:

|  | male/female | | | | | |
| --- | --- | --- | --- | --- | --- | --- |
|  | Mouse m | Mouse f | Rat m/f | Dog m/f | Cyno f | Man m/f |
| microsomal protein [mg]/ g liver | 40 | 40 | 40 | 40 | 40 | 40 |
| liver [g]/ kg body weight | 50 | 43 | 32 | 39 | 30 | 21 |
| liver blood flow [L/(h · kg)] | 5.4 | 5.4 | 4.2 | 2.1 | 2.5 | 1.3 |

$F_{max}$ values (maximal possible bioavailability) are calculated using the formula:

$$F_{max} \text{ well-stirred } [\%]=[1-(CL_{blood}\text{ well-stirred } [\text{L}/(\text{h}\cdot\text{kg})]/Q_H[\text{L}/(\text{h}\cdot\text{kg})])]\cdot 100.$$

In-Vitro Clearance Determinations with Hepatocytes:

Incubations with hepatocytes are performed at 37° C. in a total volume of 1.5 ml using a modified Janus® robotic system (Perkin-Elmer). The incubation mixtures contain 1 million viable cells/ml, ~1 µM substrate and 0.05 M potassium phosphate buffer (pH 7.4). The final acetonitrile (ACN) concentration is ≤1%.

Aliquots of 125 µl are withdrawn from the incubation mixture after 2, 10, 20, 30, 50, 70 and 90 min and typically dispensed in a 96-well filter plate (0.45 µm low-binding hydrophilic PTFE; Millipore, MultiScreen Solvinert), containing 250 µl ACN to stop the reaction. After centrifugation, filtrates are analyzed by MSMS (typically API 2000 or API 3000).

Calculation of in-vitro clearance values (CL) from half-life data ($t_{1/2}$) in hepatocytes, reflecting substrate depletion, is performed using the following equation [J. B. Houston, *Biochem. Pharmacol.* 1994, 47 (9), 1469-79; R. S. Obach et al., *J. Pharmacol. Exp. Ther.* 1997, 283 (1), 46-58]:

$$CL_{intrinsic}'[\text{ml}/(\text{min}\cdot\text{kg})]=(0.693/\text{in vitro } t_{1/2} \text{ [min]})\cdot (\text{liver weight [g liver/kg body mass]})\cdot(\text{cell number } [1.1\cdot 10^8]/\text{liver weight [g]})/(\text{cell number } [1\cdot 10^6]/\text{incubation volume [ml]}).$$

The $CL_{blood}$ value is estimated using the non-restricted well-stirred model [K. S. Pang, M. Rowland, *J. Pharmacokin. Biopharm.* 1977, 5 (6), 625-53]:

$$CL_{blood} \text{ well-stirred } [\text{L}/(\text{h}\cdot\text{kg})]=(Q_H \text{ [L}/(\text{h}\cdot\text{kg})]\cdot CL_{intrinsic}'[\text{L}/(\text{h}\cdot\text{kg})])/(Q_H[\text{L}/(\text{h}\cdot\text{kg})]+CL_{intrinsic}'[\text{L}/(\text{h}\cdot\text{kg})]).$$

Specific liver weights and hepatic blood flows ($Q_H$) are 32 g/kg body mass and 4.2 L/(h·kg), respectively, for rats, 40 g/kg body mass and 2.1 L/(h·kg) for dogs, and 21 g/kg body mass and 1.32 L/(h·kg) for man. The cell number in the liver is supposed to be 110 million cells/g liver for all species used.

Species-specific factors for the prediction of in-vivo clearance values for other species are shown below:

|  | male/female | | | | | |
| --- | --- | --- | --- | --- | --- | --- |
|  | Mouse m | Mouse f | Rat m/f | Dog m/f | Cyno f | Man m/f |
| cell number [·10$^6$]/g liver | 110 | 110 | 110 | 110 | 110 | 110 |
| liver [g]/ kg body weight | 50 | 43 | 32 | 39 | 30 | 21 |
| liver blood flow [L/(h · kg)] | 5.4 | 5.4 | 4.2 | 2.1 | 2.5 | 1.3 |

$F_{max}$ values (maximal possible bioavailability) are calculated using the formula:

$F_{max}$ well-stirred [%]=[1−(CL$_{blood}$ well-stirred [L/ (h·kg)]/$Q_H$ [L/(h·kg)])]·100.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

C. EXAMPLES RELATING TO PHARMACEUTICAL COMPOSITIONS

Pharmaceutical compositions according to the present invention can be illustrated as follows:

Sterile i.v. Solution:

A 5 mg/ml solution of the desired compound of this invention can be made using sterile, injectable water, and the pH is adjusted if necessary. The solution is diluted for administration to 1-2 mg/ml with sterile 5% dextrose and is administered as an i.v. infusion over about 60 minutes.

Lyophilized Powder for i.v. Administration:

A sterile preparation can be prepared with (i) 100-1000 mg of the desired compound of this invention as a lyophilized powder, (ii) 32-327 mg/ml sodium citrate, and (iii) 300-3000 mg Dextran 40. The formulation is reconstituted with sterile, injectable saline or 5% dextrose to a concentration of 10 to 20 mg/ml, which is further diluted with saline or 5% dextrose to 0.2 to 0.4 mg/ml, and is administered either as i.v. bolus or by i.v. infusion over 15-60 minutes.

Intramuscular Suspension:

The following solution or suspension can be prepared for intramuscular injection:

50 mg/ml of the desired, water-insoluble compound of this invention; 5 mg/ml sodium carboxymethylcellulose; 4 mg/mL TWEEN 80; 9 mg/ml sodium chloride; 9 mg/ml benzyl alcohol.

Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water-miscible medicine mix.

Tablets:

A large number of tablets are prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability, or delay absorption.

We claim:

1. A compound of formula (I)

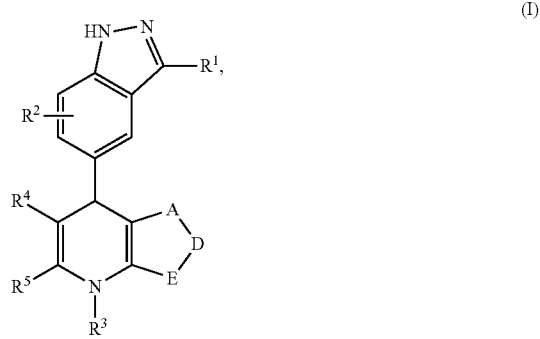

wherein

A is —C(=O)— or —S(=O)$_2$—,

D is —CR$^{6A}$R$^{6B}$—, —O— or —NR$^7$—, wherein R$^{6A}$, R$^{6B}$ and R$^7$ are independently hydrogen or (C$_1$-C$_4$)-alkyl optionally substituted with hydroxy or up to three fluoro atoms, E is —CR$^{8A}$R$^{8B}$— or *—CR$^{8A}$R$^{8B}$—CR$^{8C}$R$^{8D}$—**, wherein

* denotes the link to the dihydropyridine ring,

** denotes the link to the D group, and

R$^{8A}$, R$^{8B}$, R$^{8C}$ and R$^{8D}$ are independently hydrogen, fluoro or (C$_1$-C$_4$)-alkyl optionally substituted with hydroxy, (C$_1$-C$_4$)-alkoxy, amino, mono-(C$_1$-C$_4$)-alkylamino or di-(C$_1$-C$_4$)-alkylamino or up to three fluoro atoms, or R$^{8A}$ and R$^{8B}$ are joined and, taken together with the carbon atom to which they are attached, form a cyclopropyl or cyclobutyl ring, R$^1$ is selected from the group consisting of hydrogen, chloro, bromo, (C$_1$-C$_6$)-alkyl, (C$_3$-C$_7$)-cycloalkyl, phenyl, 4- to 7-membered heterocycloalkyl, 5- to 10-membered heteroaryl and benzo-1,4-dioxanyl, wherein (i) said (C$_3$-C$_7$)-cycloalkyl, phenyl, 4- to 7-membered heterocycloalkyl and 5- to 10-membered heteroaryl are optionally substituted with one or two substituents independently selected from the group consisting of fluoro, chloro, bromo, difluoromethyl, trifluoromethyl, (C$_1$-C$_4$)-alkyl, oxo, hydroxy, difluoromethoxy, trifluoromethoxy, (C$_1$-C$_4$)-alkoxy, amino, mono-(C$_1$-C$_4$)-alkylamino, di-(C$_1$-C$_4$)-alkylamino, (C$_3$-C$_6$)-cycloalkyl and 4- to 6-membered heterocycloalkyl, wherein the alkyl groups of said (C$_1$-C$_4$)-alkoxy, mono-(C$_1$-C$_4$)-alkylamino and di-(C$_1$-C$_4$)-alkylamino substituents in turn are optionally substituted with hydroxy or (C$_1$-C$_4$)-alkoxy, and (ii) said $(C_1-C_6)$-alkyl is optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, $(C_3-C_7)$-cycloalkyl, phenyl, 4- to 7-membered heterocycloalkyl and 5- to 10-membered heteroaryl, wherein said $(C_3-C_7)$-cycloalkyl, phenyl, 4- to 7-membered heterocycloalkyl and 5- to 10-membered heteroaryl substituents in turn are optionally substituted with one or two residues independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino and di-$(C_1-C_4)$-alkylamino, or $R^1$ is a group of the formula —$NR^{9A}R^{9B}$ or —$OR^{10}$, wherein $R^{9A}$ and $R^{9B}$ are independently selected from the group consisting of hydrogen, $(C_1-C_6)$-alkyl, $(C_3-C_7)$-cycloalkyl and 4- to 7-membered heterocycloalkyl, wherein (i) said $(C_3-C_7)$-cycloalkyl and 4- to 7-membered heterocycloalkyl are optionally substituted with one or two substituents independently selected from the group consisting of fluoro, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino and di-$(C_1-C_4)$-alkylamino, and (ii) said $(C_1-C_6)$-alkyl is optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, $(C_3-C_7)$-cycloalkyl, phenyl, 4- to 7-membered heterocycloalkyl and 5- to 10-membered heteroaryl, wherein said $(C_3-C_7)$-cycloalkyl, phenyl, 4- to 7-membered heterocycloalkyl and 5- to 10-membered heteroaryl substituents in turn are optionally substituted with one or two residues independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino and di-$(C_1-C_4)$-alkylamino, or $R^{9A}$ and $R^{9B}$ are joined and, taken together with the nitrogen atom to which they are attached, form a 4- to 7-membered heterocycloalkyl ring, which may contain a second ring heteroatom selected from N, O and S, and which is optionally substituted with one or two substituents independently selected from the group consisting of fluoro, $(C_1-C_4)$-alkyl, oxo, hydroxy, $(C_1-C_4)$-alkoxy, amino, mono-$(C_1-C_4)$-alkylamino, di-$(C_1-C_4)$-alkylamino and $(C_3-C_6)$-cycloalkyl, $R^{10}$ is selected from the group consisting of $(C_1-C_6)$-alkyl, $(C_3-C_7)$-cycloalkyl and 4- to 7-membered heterocycloalkyl, wherein (i) said $(C_3-C_7)$-cycloalkyl and 4- to 7-membered heterocycloalkyl are optionally substituted with one or two substituents independently selected from the group consisting of fluoro, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino and di-$(C_1-C_4)$-alkylamino, and (ii) said $(C_1-C_6)$-alkyl is optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, $(C_3-C_7)$-cycloalkyl, phenyl, 4- to 7-membered heterocycloalkyl and 5- to 10-membered heteroaryl, wherein said $(C_3-C_7)$-cycloalkyl, phenyl, 4- to 7-membered heterocycloalkyl and 5- to 10-membered heteroaryl substituents in turn are optionally substituted with one or two residues independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino and di-$(C_1-C_4)$-alkylamino, $R^2$ is hydrogen, fluoro, chloro or methyl, $R^3$ is hydrogen, $(C_1-C_4)$-alkyl or cyclopropyl, $R^4$ is cyano or aminocarbonyl, $R^5$ is selected from the group consisting of $(C_1-C_6)$-alkyl, $(C_3-C_7)$-cycloalkyl, phenyl and 5- or 6-membered heteroaryl, wherein (i) said $(C_3-C_7)$-cycloalkyl, phenyl and 5- or 6-membered heteroaryl are optionally substituted with one or two substituents independently selected from the group consisting of fluoro, chloro, bromo, cyano, difluoromethyl, trifluoromethyl, $(C_1-C_4)$-alkyl, hydroxy, difluoromethoxy, trifluoromethoxy, $(C_1-C_4)$-alkoxy, amino, mono-$(C_1-C_4)$-alkylamino and di-$(C_1-C_4)$-alkylamino, and (ii) said $(C_1-C_6)$-alkyl is optionally substituted with up to three fluoro atoms or with one or two substituents independently selected from the group consisting of trifluoromethyl, hydroxy, $(C_1-C_4)$-alkoxy, amino, mono-$(C_1-C_4)$-alkylamino, di-$(C_1-C_4)$-alkylamino, $(C_3-C_7)$-cycloalkyl, phenyl, 4- to 7-membered heterocycloalkyl and 5- or 6-membered heteroaryl, wherein the alkyl groups of said $(C_1-C_4)$-alkoxy, mono-$(C_1-C_4)$-alkylamino and di-$(C_1-C_4)$-alkylamino substituents in turn are optionally substituted with up to three fluoro atoms or with one or two residues independently selected from the group consisting of trifluoromethyl, hydroxy, $(C_1-C_4)$-alkoxy, amino, mono-$(C_1-C_4)$-alkylamino, di-$(C_1-C_4)$-alkylamino and 4- to 7-membered heterocycloalkyl, and wherein said $(C_3-C_7)$-cycloalkyl, phenyl, 4- to 7-membered heterocycloalkyl and 5- or 6-membered heteroaryl groups in turn are optionally substituted with one or two residues independently selected from the group consisting of fluoro, chloro, cyano, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino, or $R^5$ is $(C_1-C_4)$-alkoxycarbonyl, aminocarbonyl, mono-$(C_1-C_4)$-alkylaminocarbonyl or di-$(C_1-C_4)$-alkylaminocarbonyl, or $R^3$ and $R^5$ are joined and, taken together with the nitrogen and the carbon atom to which they are attached, form a fused ring of the formula

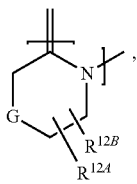

wherein

G is —$CH_2$—, —$C(CH_3)_2$—, —$CH(CF_3)$—, —O— or —$NR^{11}$-, wherein
$R^{11}$ is hydrogen or $(C_1-C_4)$-alkyl,
and
$R^{12A}$ and $R^{12B}$ are independently hydrogen or fluoro, or $R^4$ and $R^5$ are joined and, taken together with the carbon atoms to which they are attached, form a fused lactone or lactame ring of the formula

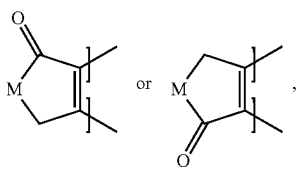

wherein
M is —O— or —$NR^{13}$—, wherein
$R^{13}$ is hydrogen or $(C_1-C_4)$-alkyl,
or a pharmaceutically acceptable salt thereof.

2. The compound of formula (I) according to claim 1, wherein
A is —C(=O)—,
D is —$CH_2$—, —O—, —NH— or —$N(CH_3)$—,
E is —$CR^{8A}R^{8B}$— or *—$CR^{8A}R^{8B}$—$CH_2$—**, wherein
* denotes the link to the dihydropyridine ring,
** denotes the link to the D group,
and
$R^{8A}$ and $R^{8B}$ are independently hydrogen or methyl,
or
$R^{8A}$ and $R^{8B}$ are joined and, taken together with the carbon atom to which they are attached, form a cyclopropyl ring,
$R^1$ is selected from the group consisting of hydrogen, $(C_1-C_6)$-alkyl, $(C_3-C_6)$-cycloalkyl, phenyl, 4- to 6-membered heterocycloalkyl and 5- or 6-membered heteroaryl, wherein
(i) said $(C_3-C_6)$-cycloalkyl, phenyl, 4- to 6-membered heterocycloalkyl and 5- or 6-membered heteroaryl are optionally substituted with one or two substituents independently selected from the group consisting of fluoro, chloro, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino, di-$(C_1-C_4)$-alkylamino and 4- to 6-membered heterocycloalkyl,
wherein the alkyl groups of said $(C_1-C_4)$-alkoxy, mono-$(C_1-C_4)$-alkylamino and di-$(C_1-C_4)$-alkylamino substituents in turn are optionally substituted with hydroxy, methoxy or ethoxy, and (ii) said $(C_1-C_6)$-alkyl is optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, $(C_3-C_6)$-cycloalkyl, 4- to 6-membered heterocycloalkyl and 5- or 6-membered heteroaryl,
wherein said $(C_3-C_6)$-cycloalkyl, 4- to 6-membered heterocycloalkyl and 5- or 6-membered heteroaryl substituents in turn are optionally substituted with one or two residues independently selected from the group consisting of fluoro, chloro, difluoromethyl, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino, or $R^1$ is a group of the formula —$NR^{9A}R^{9B}$ or —$OR^{10}$, wherein
$R^{9A}$ is hydrogen or $(C_1-C_4)$-alkyl optionally substituted with one or two substituents independently selected from the group consisting of hydroxy, $(C_1-C_4)$-alkoxy, amino, mono-$(C_1-C_4)$-alkylamino and di-$(C_1-C_4)$-alkylamino,
$R^{9B}$ is selected from the group consisting of hydrogen, $(C_1-C_6)$-alkyl, $(C_3-C_6)$-cycloalkyl and 4- to 6-membered heterocycloalkyl, wherein
(i) said $(C_3-C_6)$-cycloalkyl and 4- to 6-membered heterocycloalkyl are optionally substituted with one or two substituents independently selected from the group consisting of fluoro, difluoromethyl, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino, and (ii) said $(C_1-C_6)$-alkyl is optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, $(C_3-C_6)$-cycloalkyl, 4- to 6-membered heterocycloalkyl and 5- or 6-membered heteroaryl,
wherein said $(C_3-C_6)$-cycloalkyl, 4- to 6-membered heterocycloalkyl and 5- or 6-membered heteroaryl substituents in turn are optionally substituted with one or two residues independently selected from the group consisting of fluoro, chloro, difluoromethyl, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino, or $R^{9A}$ and $R^{9B}$ are joined and, taken together with the nitrogen atom to which they are attached, form a 4- to 6-membered heterocycloalkyl ring, which may contain a second ring heteroatom selected from N and O, and which is optionally substituted with one or two substituents independently selected from the group consisting of fluoro, ($C_1$-$C_4$)-alkyl, oxo, hydroxy, ($C_1$-$C_4$)-alkoxy, amino, mono-($C_1$-$C_4$)-alkylamino and di-($C_1$-$C_4$)-alkylamino, $R^{10}$ is selected from the group consisting of ($C_1$-$C_6$)-alkyl, ($C_3$-$C_6$)-cycloalkyl and 4- to 6-membered heterocycloalkyl, wherein
  (i) said ($C_3$-$C_6$)-cycloalkyl and 4- to 6-membered heterocycloalkyl are optionally substituted with one or two substituents independently selected from the group consisting of fluoro, difluoromethyl, trifluoromethyl, ($C_1$-$C_4$)-alkyl, oxo, hydroxy, ($C_1$-$C_4$)-alkoxy, amino, mono-($C_1$-$C_4$)-alkylamino and di-($C_1$-$C_4$)-alkylamino,
  and
  (ii) said ($C_1$-$C_6$)-alkyl is optionally substituted with one, two or three substituents independently selected from the group consisting of fluoro, trifluoromethyl, hydroxy, ($C_1$-$C_4$)-alkoxy, amino, mono-($C_1$-$C_4$)-alkylamino, di-($C_1$-$C_4$)-alkylamino, ($C_3$-$C_6$)-cycloalkyl, 4- to 6-membered heterocycloalkyl and 5- or 6-membered heteroaryl,
    wherein said ($C_3$-$C_6$)-cycloalkyl, 4- to 6-membered heterocycloalkyl and 5- or 6-membered heteroaryl substituents in turn are optionally substituted with one or two residues independently selected from the group consisting of fluoro, chloro, difluoromethyl, trifluoromethyl, ($C_1$-$C_4$)-alkyl, oxo, hydroxy, ($C_1$-$C_4$)-alkoxy, amino, mono-($C_1$-$C_4$)-alkylamino and di-($C_1$-$C_4$)-alkylamino, $R^2$ is hydrogen or fluoro,
$R^3$ is hydrogen or ($C_1$-$C_4$)-alkyl,
$R^4$ is cyano,
$R^5$ is selected from the group consisting of ($C_1$-$C_4$)-alkyl, cyclopropyl, phenyl and 5- or 6-membered heteroaryl, wherein
  (i) said cyclopropyl is optionally substituted with one or two substituents independently selected from the group consisting of fluoro, trifluoromethyl and methyl,
  (ii) said phenyl and 5- or 6-membered heteroaryl are optionally substituted with one or two substituents independently selected from the group consisting of fluoro, chloro, cyano, difluoromethyl, trifluoromethyl, ($C_1$-$C_4$)-alkyl and ($C_1$-$C_4$)-alkoxy,
  and
  (iii) said ($C_1$-$C_4$)-alkyl is optionally substituted with up to three fluoro atoms or with one or two substituents independently selected from the group consisting of ($C_1$-$C_4$)-alkoxy, amino, mono-($C_1$-$C_4$)-alkylamino, di-($C_1$-$C_4$)-alkylamino, ($C_3$-$C_6$)-cycloalkyl, phenyl, 4- to 6-membered heterocycloalkyl and 5-membered heteroaryl,
    wherein the alkyl groups of said ($C_1$-$C_4$)-alkoxy, mono-($C_1$-$C_4$)-alkylamino and di-($C_1$-$C_4$)-alkylamino substituents in turn are optionally substituted with up to three fluoro atoms or with one or two residues independently selected from the group consisting of ($C_1$-$C_4$)-alkoxy, amino, mono-($C_1$-$C_4$)-alkylamino, di-($C_1$-$C_4$)-alkylamino and 4- to 6-membered heterocycloalkyl,
    and wherein said ($C_3$-$C_6$)-cycloalkyl, phenyl, 4- to 6-membered heterocycloalkyl and 5-membered heteroaryl groups in turn are optionally substituted with one or two residues independently selected from the group consisting of fluoro, chloro, cyano, trifluoromethyl, ($C_1$-$C_4$)-alkyl, oxo, ($C_1$-$C_4$)-alkoxy, amino, mono-($C_1$-$C_4$)-alkylamino and di-($C_1$-$C_4$)-alkylamino, or $R^3$ and $R^5$ are joined and, taken together with the nitrogen and the carbon atom to which they are attached, form a fused ring of the formula

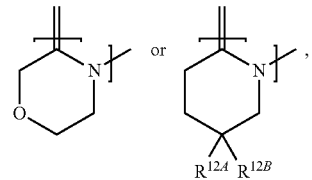

wherein
$R^{12A}$ and $R^{12B}$ are independently hydrogen or fluoro, or $R^4$ and $R^5$ are joined and, taken together with the carbon atoms to which they are attached, form a fused lactone ring of the formula

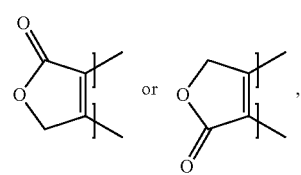

or a pharmaceutically acceptable salt thereof.

3. The compound of formula (I) according to claim 1, wherein
A is —C(=O)—,
D is —O—,
E is —$CH_2$—, —CH($CH_3$)— or —C($CH_3$)$_2$—,
$R^1$ is selected from the group consisting of hydrogen, ($C_1$-$C_4$)-alkyl, phenyl and 5- or 6-membered heteroaryl, wherein
  (i) said phenyl and 5- or 6-membered heteroaryl are optionally substituted with one or two substituents independently selected from the group consisting of fluoro, chloro, difluoromethyl, trifluoromethyl, ($C_1$-$C_3$)-alkyl, ($C_1$-$C_3$)-alkoxy, amino, mono-($C_1$-$C_3$)-alkylamino, di-($C_1$-$C_3$)-alkylamino and 4- to 6-membered heterocycloalkyl,
    wherein the alkyl groups of said ($C_1$-$C_3$)-alkoxy, mono-($C_1$-$C_3$)-alkylamino and di-($C_1$-$C_3$)-alkylamino substituents in turn are optionally substituted with methoxy or ethoxy,
  and
  (ii) said ($C_1$-$C_4$)-alkyl is optionally substituted with up to three fluoro atoms or with one or two substituents independently selected from the group consisting of ($C_1$-$C_3$)-alkoxy, amino, mono-($C_1$-$C_3$)-alkylamino, di-($C_1$-$C_3$)-alkylamino and 4- to 6-membered heterocycloalkyl,
    wherein said 4- to 6-membered heterocycloalkyl substituent in turn is optionally substituted with one or two residues independently selected from the group consisting of fluoro, trifluoromethyl, methyl, ethyl, oxo, methoxy, ethoxy, amino, methylamino, ethylamino, dimethylamino and diethylamino, or $R^1$ is a group of the formula —$NR^{9A}R^{9B}$ or —$OR^{10}$, wherein $R^{9A}$ is hydrogen or ($C_1$-$C_4$)-alkyl optionally substituted with hydroxy, methoxy, ethoxy, amino, methylamino, ethylamino, dimethylamino or diethylamino, $R^{9B}$ is hydrogen or ($C_1$-$C_4$)-alkyl optionally substituted with up to three fluoro atoms or with one or two substituents independently selected from the group consisting of hydroxy, ($C_1$-$C_3$)-alkoxy, amino, mono-($C_1$-$C_3$)-alkylamino, di-($C_1$-$C_3$)-alkylamino and 4- to 6-membered heterocycloalkyl, wherein said 4- to 6-membered heterocycloalkyl substituent in turn is optionally substituted with one or two residues independently selected from the group consisting of fluoro, trifluoromethyl, methyl, ethyl, oxo, methoxy, ethoxy, amino, methylamino, ethylamino, dimethylamino and diethylamino, or $R^{9A}$ and $R^{9B}$ are joined and, taken together with the nitrogen atom to which they are attached, form a 4- to 6-membered heterocycloalkyl ring, which may contain a second ring heteroatom selected from N and O, and which is optionally substituted with one or two substituents independently selected from the group consisting of fluoro, methyl, ethyl, oxo, methoxy, ethoxy, amino, methylamino, ethylamino, dimethylamino and diethylamino, $R^{10}$ is ($C_1$-$C_4$)-alkyl optionally substituted with up to three fluoro atoms or with one or two substituents independently selected from the group consisting of hydroxy, ($C_1$-$C_3$)-alkoxy, amino, mono-($C_1$-$C_3$)-alkylamino, di-($C_1$-$C_3$)-alkylamino and 4- to 6-membered heterocycloalkyl, wherein said 4- to 6-membered heterocycloalkyl substituent in turn is optionally substituted with one or two residues independently selected from the group consisting of fluoro, trifluoromethyl, methyl, ethyl, oxo, methoxy, ethoxy, amino, methylamino, ethylamino, dimethylamino and diethylamino, $R^2$ is hydrogen or fluoro, $R^3$ is hydrogen or methyl, $R^4$ is cyano, and $R^5$ is selected from the group consisting of ($C_1$-$C_4$)-alkyl, phenyl, pyridyl, pyrimidinyl, oxazolyl and isoxazolyl, wherein (i) said phenyl, pyridyl, pyrimidinyl, oxazolyl and isoxazolyl are optionally substituted with one or two substituents independently selected from the group consisting of fluoro, chloro, difluoromethyl, trifluoromethyl, methyl, ethyl, methoxy and ethoxy, and (ii) said ($C_1$-$C_4$)-alkyl is optionally substituted with up to three fluoro atoms or with a substituent selected from the group consisting of ($C_1$-$C_3$)-alkoxy, amino, mono-($C_1$-$C_3$)-alkylamino, di-($C_1$-$C_3$)-alkylamino, phenyl, 4- to 6-membered heterocycloalkyl and 5-membered heteroaryl, wherein said phenyl and 5-membered heteroaryl substituents in turn are optionally substituted with one or two residues independently selected from the group consisting of fluoro, chloro, trifluoromethyl, methyl, ethyl and amino, and wherein the alkyl groups of said ($C_1$-$C_3$)-alkoxy, mono-($C_1$-$C_3$)-alkylamino and di-($C_1$-$C_3$)-alkylamino substituents in turn are optionally substituted with up to three fluoro atoms or with a residue selected from the group consisting of methoxy, ethoxy, amino, methylamino, ethylamino, dimethylamino, diethylamino, azetidino, pyrrolidino, piperidino, piperazino and morpholino, and wherein said 4- to 6-membered heterocycloalkyl substituent as well as said azetidino, pyrrolidino, piperidino, piperazino and morpholino groups in turn are optionally substituted with one or two residues independently selected from the group consisting of fluoro, methyl, ethyl and oxo, or a pharmaceutically acceptable salt thereof.

4. The compound of formula (I) according to claim 1, wherein

A is —C(═O)—,

D is —O—,

E is —$CH_2$—, $R^1$ is hydrogen, methyl or ethyl, $R^2$ is hydrogen or fluoro, $R^3$ is hydrogen or methyl, $R^4$ is cyano, and $R^5$ is ($C_1$-$C_4$)-alkyl optionally substituted with methoxy, ethoxy or up to three fluoro atoms, or is phenyl optionally substituted with one or two substituents independently selected from the group consisting of fluoro, chloro, methyl and trifluoromethyl, or a pharmaceutically acceptable salt thereof.

5. A process for preparing a compound of formula (I) as defined in claim 1, wherein $R^3$ is hydrogen, characterized in that an indazolyl aldehyde of formula (II)

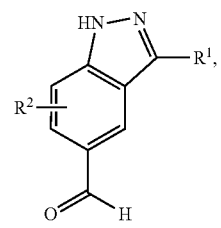

(II)

wherein $R^1$ and $R^2$ have the meanings indicated in claim 1, is reacted either

[A] with a compound of formula (III)

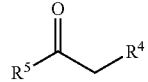

(III)

or sodium enolate thereof, wherein $R^4$ and $R^5$ have the meanings indicated in claim 1, in the presence of an acid, an acid/base combination and/or a dehydrating agent to give a compound of formula (IV)

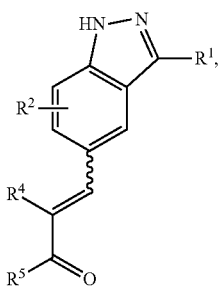
(IV)

wherein $R^1$, $R^2$, $R^4$ and $R^5$ have the meanings described above,
and the latter is then condensed with a compound of formula (V)

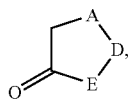
(V)

wherein A, D and E have the meanings indicated in claim 1,
in the presence of an ammonia source such as ammonium acetate to give the compound of formula (I-A)

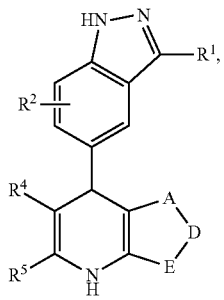
(I-A)

wherein A, D, E, $R^1$, $R^2$, $R^4$ and $R^5$ have the meanings described above,
or
[B] with a compound of formula (V)

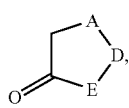
(V)

wherein A, D and E have the meanings indicated in claim 1,
optionally in the presence of a base and/or a dehydrating agent to yield a compound of formula (VI)

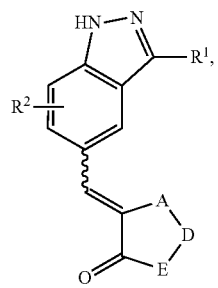
(VI)

wherein A, D, E, $R^1$ and $R^2$ have the meanings described above,
and the latter is then condensed with a compound of formula (VII)

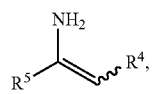
(VII)

wherein $R^4$ and $R^5$ have the meanings indicated in claim 1,
in the presence of an acid to give the compound of formula (I-A)

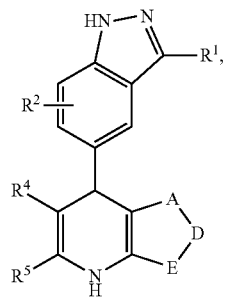
(I-A)

wherein A, D, E, $R^1$, $R^2$, $R^4$ and $R^5$ have the meanings described above,
optionally followed, where appropriate, by (i) separating the compounds (I-A) into their respective enantiomers and/or diastereomers, and/or (ii) converting the compounds (I-A) into their respective salts by treatment with the corresponding solvents and/or acids or bases.

6. A pharmaceutical composition comprising a compound as defined in claim 1 and a pharmaceutically acceptable excipient.

7. The pharmaceutical composition of claim 6 further comprising one or more additional therapeutic agents.

8. The pharmaceutical composition of claim 7, wherein the additional therapeutic agent is an anti-tumor agent.

9. A method of treating a cell proliferative disorder selected from a cancer of the breast, respiratory tract, brain, reproductive organs, digestive tract, urinary tract, eye, liver, skin, head or neck, thyroid, parathyroid, or a distant metastasis of a solid tumor, comprising administering to a mammal in need thereof a therapeutically effective amount of one or more compounds as defined in claim 1.

10. The method of claim 9, wherein the compound as defined in claim 1 is administered in conjunction with surgery or radiation therapy.

11. A method of treating a cell proliferative disorder selected from a cancer of the breast, respiratory tract, brain, reproductive organs, digestive tract, urinary tract, eye, liver, skin, head or neck, thyroid, parathyroid, or a distant metastasis of a solid tumor, comprising administering to a mammal in need thereof a therapeutically effective amount of a pharmaceutical composition as defined in claim 6.

12. The method of claim 11, wherein the pharmaceutical composition as defined in claim 6 is administered in conjunction with surgery or radiation therapy.

\* \* \* \* \*